US011286499B2

(12) United States Patent
Akbar et al.

(10) Patent No.: US 11,286,499 B2
(45) Date of Patent: *Mar. 29, 2022

(54) COTTON TRANSGENIC EVENT MON 88702 AND METHODS FOR DETECTION AND USES THEREOF

(71) Applicant: Monsanto Technology LLC, St. Louis, MO (US)

(72) Inventors: Waseem Akbar, Ballwin, MO (US); Robert S. Brown, Lake Saint Louis, MO (US); Wen C. Burns, Chesterfield, MO (US); Thomas L. Clark, Williamsburg, MO (US); Stanislaw Flasinski, Ballwin, MO (US); Anilkumar Gowda, Chesterfield, MO (US); Aihong Pan, St. Louis, MO (US); Xiaohong Shi, Ballwin, MO (US); Jason W. Stelzer, Wildwood, MO (US); Kunsheng Wu, Ballwin, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/808,202

(22) Filed: Mar. 3, 2020

(65) Prior Publication Data

US 2020/0270629 A1  Aug. 27, 2020

Related U.S. Application Data

(62) Division of application No. 15/341,968, filed on Nov. 2, 2016, now Pat. No. 10,604,769.

(60) Provisional application No. 62/249,758, filed on Nov. 2, 2015.

(51) Int. Cl.
  *C12N 15/82* (2006.01)
  *A01H 1/02* (2006.01)
  *A01N 65/08* (2009.01)
  *C12Q 1/6895* (2018.01)
  *A01H 1/04* (2006.01)

(52) U.S. Cl.
  CPC .......... *C12N 15/8286* (2013.01); *A01H 1/02* (2013.01); *A01H 1/04* (2013.01); *A01N 65/08* (2013.01); *C12Q 1/6895* (2013.01); *C12Q 2600/13* (2013.01); *C12Q 2600/156* (2013.01); *C12Q 2600/16* (2013.01); *Y02A 40/146* (2018.01)

(58) Field of Classification Search
  None
  See application file for complete search history.

(56) References Cited

U.S. PATENT DOCUMENTS

| 8,609,936 | B2 * | 12/2013 | Baum | C07K 14/325 |
| | | | | 800/302 |
| 8,940,962 | B2 | 1/2015 | Flasinski | |
| 9,322,033 | B2 | 4/2016 | Baum et al. | |
| 10,604,769 | B2 * | 3/2020 | Akbar | A01N 65/08 |
| 2005/0216969 | A1 | 9/2005 | Song | |
| 2013/0269060 | A1 | 10/2013 | Baum et al. | |

FOREIGN PATENT DOCUMENTS

| CN | 101300353 | 11/2008 |
| CN | 103597079 | 2/2014 |
| WO | 2001/077384 | 10/2001 |
| WO | 2007027776 | 3/2007 |
| WO | 2012048124 | 4/2012 |
| WO | 2012134808 | 10/2012 |
| WO | 2012139004 | 10/2012 |
| WO | 2014062544 | 4/2014 |
| WO | 2015021354 | 2/2015 |
| WO | 2015105993 | 7/2015 |
| WO | 2015120276 | 8/2015 |

OTHER PUBLICATIONS

Gowda et al., "A transgenic approach for controlling Lygus in cotton," Nature Communications 7:1-7, 2016.
Jerga et al., "Mechanistic insights into the first Lygus-active β-pore forming protein," Archives of Biochemistry and Biophysics 600:1-11, 2016.
Moar et al., "The sequence, structural, and functional diversity within a protein family and implications for specificity and safety: The Case for ETX_MTX2 insecticidal proteins," Journal of Invertebrate Pathology pp. 1-10, 2016.
International Search Report and Written Opinion regarding International Application No. PCT/US2016/060081, dated Mar. 23, 2017.
Baum et al, "Cotton Plants Expressing a Hemipteran-Active Bacillus thuringiensis Crystal Protein Impact the Development and Survival of Lygus hesperus (Hemiptera:Miridau) Nymphs", J. Econ, Entomol. 105(2):616-624, 2012.
Shera et al., "Comparative susceptibility of transgenic Bt cotton hybrids to *Earias* spp. and other non-target insects", Corp Protection 71, pp. 51-59, 2015.
Rusch et al., PLoS Biol. 5(3), e77 (2007).
Akbar et al., "Frirst transgenic trait for control of plant bugs and thrips in cotton," Pest Management Science 75(3):867-877, 2019.

(Continued)

*Primary Examiner* — Juliet C Switzer
(74) *Attorney, Agent, or Firm* — Dentons US LLP; Timothy K. Ball

(57) ABSTRACT

The invention provides a transgenic *Gossypium hirsutum* event MON 88702, plants, plant cells, seeds, plant parts, progeny plants, and commodity products comprising event MON 88702. The invention also provides polynucleotides specific for event MON 88702, plants, plant cells, seeds, plant parts, progeny plants, and commodity products comprising polynucleotides for event MON 88702. The invention also provides methods related to event MON 88702.

8 Claims, 1 Drawing Sheet

Specification includes a Sequence Listing.

(56) References Cited

OTHER PUBLICATIONS

Bachman et al., "Characterization of the activity spectrum of MON 88702 and the plantincorporated protectant Cry51Aa2.834_16," PLoS ONE 12(1):e0169409, 2017.

Jensen et al., Insecticide resistance in western flower thrips, Frankliniella occidentalis, Integrated Pest Management Reviews 5:131:146, 2000.

Snodgrass et al., "Acephate resistance in populations of the tarnished plant bug (Heteroptera: Miraidae) from the Mississippi River Delta," J. Econ. Entomol. 102(2): 699-707, 2009.

\* cited by examiner

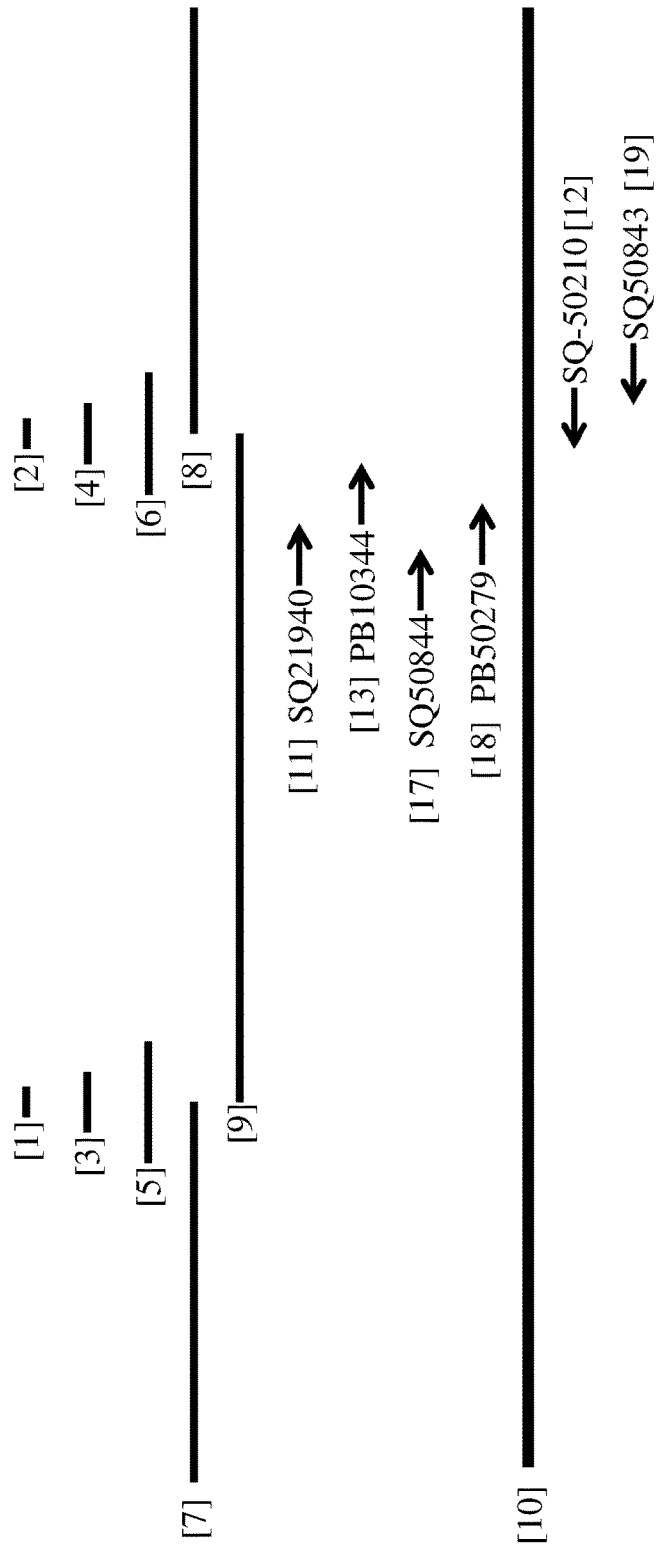
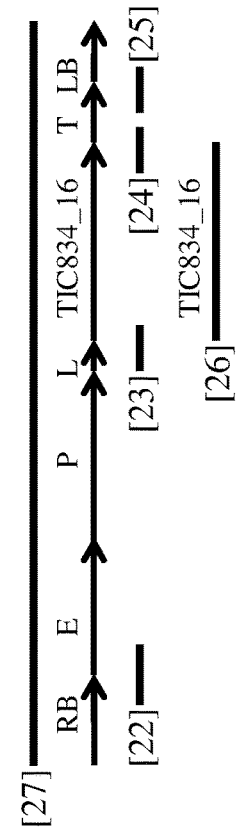
FIG. 1a
FIG. 1b

SEQUENCE LISTING

```
<160> NUMBER OF SEQ ID NOS: 27

<210> SEQ ID NO 1
<211> LENGTH: 20
<212> TYPE: DNA
<213> ORGANISM: Artificial
<220> FEATURE:
<223> OTHER INFORMATION: A twenty nucleotide sequence representing the
      5' junction regions of cotton genomic DNA and the integrated
      transgenic expression cassette.

<400> SEQUENCE: 1
aaaaaaatat agtcagcatc                                                    20

<210> SEQ ID NO 2
<211> LENGTH: 20
<212> TYPE: DNA
<213> ORGANISM: Artificial
<220> FEATURE:
<223> OTHER INFORMATION: A twenty nucleotide sequence representing the
      3' junction regions of cotton genomic DNA and the integrated
      transgenic expression cassette.

<400> SEQUENCE: 2
ctttcttttt tcaatataaa                                                    20

<210> SEQ ID NO 3
<211> LENGTH: 60
<212> TYPE: DNA
<213> ORGANISM: Artificial
<220> FEATURE:
<223> OTHER INFORMATION: A sixty nucleotide sequence representing the 5'
      junction regions of cotton genomic DNA and the integrated
      transgenic expression cassette.

<400> SEQUENCE: 3
tatgaaagat aaaataatag aaaaaaatat agtcagcatc atcacaccaa aagttaggcc        60

<210> SEQ ID NO 4
<211> LENGTH: 60
<212> TYPE: DNA
<213> ORGANISM: Artificial
<220> FEATURE:
<223> OTHER INFORMATION: A sixty nucleotide sequence representing the 3'
      junction regions of cotton genomic DNA and the integrated
      trasngenic expression cassette.

<400> SEQUENCE: 4
aaaaaaaatt ggtaattact ctttcttttt tcaatataaa catgggaaat ttgaaacttc        60

<210> SEQ ID NO 5
<211> LENGTH: 100
```

```
<212> TYPE: DNA
<213> ORGANISM: Artificial
<220> FEATURE:
<223> OTHER INFORMATION: A one hundred nucleotide sequence representing
      the 5' junction regions of cotton genomic DNA and the integrated
      trasngenic expression cassette.

<400> SEQUENCE: 5
gaaatttcct cttttttcaa tatgaaagat aaaataatag aaaaaaatat agtcagcatc    60
atcacaccaa aagttaggcc cgaatagttt gaaattagaa                         100

<210> SEQ ID NO 6
<211> LENGTH: 100
<212> TYPE: DNA
<213> ORGANISM: Artificial
<220> FEATURE:
<223> OTHER INFORMATION: A one hundred nucleotide sequence representing
      the 3' junction regions of cotton genomic DNA and the integrated
      trasngenic expression cassette.

<400> SEQUENCE: 6
acatctacat ttttgaattg aaaaaaaatt ggtaattact ctttcttttt tcaatataaa    60
catgggaaat ttgaaacttc cttttttatta ttctaagaag                        100

<210> SEQ ID NO 7
<211> LENGTH: 1651
<212> TYPE: DNA
<213> ORGANISM: Gossypium hirsutum
<220> FEATURE:
<221> NAME/KEY: misc_feature
<222> LOCATION: (1)..(1651)
<223> OTHER INFORMATION: Nucleotide sequence representing the 5'
      flanking cotton genomic sequence up to the inserted T-DNA.

<400> SEQUENCE: 7
gttatatata taatttaaaa cttttttcctt tggttggaat aacaactaac attaaatttg    60
aacctctttt attttcctct atagtttttc tttttatggaa aagtgattgt acccttcttc   120
aattgtaaaa aggtgaaggg ggaatcaatg gtcatctttt gcttgattgg tgcttctccc   180
aaagtcatct aatcaaataa agatagagaa aaaaaggggg ggagggactt gaaaaaagta   240
tacttgcttt gagtgcaaga agctaccaaa acttttttaga tggaccaaaa ataaaaaagg   300
tggtagccct aaaatctccc cccccccaa gctgtgagtg acttgttatt tttatgtttg    360
cttaaagttt gacctttcat gacatgatta tcacatactt gattgtatac atgtgtgtgt   420
aaaaaagtta aatgtggggt ttggcttgca ctagtgaaaa gaattatggg acccttttgtc  480 tcatgatata ccatcaatta tcccttggaa gaggctcttt tttaaattat tgttattatt   540
tacatcaact atatgatcat ggatggatca attgtgattt tgaactttgg gggtgccttt   600
tttgatgttc taataactca aataaaaacg agactctagc aattagatga tgagaagaca   660
attaagggtg ttttttttctt tctgaagatc cctttaaatg gggtcattgg ttgatatcta   720
gcaatccttg aagcaaatat atatttatat attatatgga gagagaaagc atttttaaatg   780 atggttctta tatcattgag gtatatagtg ggagaatcat attttttcctt gtgaaggaac   840 caacaacaaa gcaagcaaac accttttgat aattatggta agataaaaata ataataaggc   900 ataatgacta actaagctct taacatttat atattctgtc gatttaatcc ttattctttt   960
ttgagctaaa tttgactatc aacctttcaa aaataattga atgttgcctt tttttttaatg  1020 gaaatacaaa ctaaaacgtt aaattttttaa acataacaac ccaaatggca atccatttgt  1080
atttcatact aattttttaa aatttttaaga acttttttata tatatatttt ttagattttg  1140
```

| aattcgcttt | tatttttaa | tcatttgtta | acataacgta | tacaacaaaa | tagtgctatg | 1200 |
| tcagcatgaa | gtatatatgg | actgccatgt | gggttgtcat | gtcaacatag | ataaaaaatt | 1260 |
| aattttttag | tcagtatttc | catttaaaag | aaaaacaatt | tgactctttt | taaaagacta | 1320 |
| atgatttaat | ttaactaaaa | aaaataaggg | tcaaattgat | caaatatata | aatattgagg | 1380 |
| gctgaattta | tcatcatacc | taatactaat | cttaagagag | agagagagtg | gagatagata | 1440 |
| gaatgatgaa | aagagatcta | acaaggtttc | aagtgtgggg | aaaaaaagtt | taggctaatg | 1500 |
| agaccacctt | ttcttttta | attaattaaa | aggaattagt | atggtatcat | atgcttaagg | 1560 |
| agtgggtatg | caaagacaa | aaacccaagg | agcttccacc | agaaatttcc | tcttttttca | 1620 |
| atatgaaaga | taaataata | gaaaaaaata | t | | | 1651 |

<210> SEQ ID NO 8
<211> LENGTH: 2010
<212> TYPE: DNA
<213> ORGANISM: Gossypium hirsutum
<220> FEATURE:
<221> NAME/KEY: misc_feature
<222> LOCATION: (1)..(2010)
<223> OTHER INFORMATION: Nucleotide sequence representing the 3'
    flanking cotton genomic sequence after the inserted T-DNA.
<220> FEATURE:
<221> NAME/KEY: misc_feature
<222> LOCATION: (1)..(4)
<223> OTHER INFORMATION: The first four nucleotides of this sequence are
    derived from an unknown origin and are not present in the non-
    transgenic DP393 variety and were likely introduced during the
    integration of the MON 88702 T-DNA.

<400> SEQUENCE: 8

| tcaatataaa | catgggaaat | ttgaaacttc | cttttatta | ttctaagaag | tattaattcc | 60 |
| ataatgaatg | catgaaggag | ttgttcaaca | aattaatgac | caaaggtgaa | attaaaagat | 120 |
| ttgtactcag | aaattaattt | ttaatttaag | tcgtgagaca | cgcttttgaa | atgcattgaa | 180 |
| gtttttttt | tttaattaaa | tacaaatttc | cagataatgt | tagggacaag | gcaaactaga | 240 |
| tggaaagaca | gtcattgaac | taataagtaa | cagtaagaat | atgtgtcttt | cttttatta | 300 |
| taacatacaa | acacttagac | attattaaaa | cagcccaagt | ttgtcgttta | caagattgc | 360 |
| aatctccata | tcatgacaat | acaatatact | ccatattgat | tgcattcata | aaatatcatt | 420 |
| ttacctcct | taccttaaat | cccattcatt | cattagcatg | agatttcaag | taaaattatg | 480 |
| aactgaaaat | tagccaaatt | tattcaaatt | ttgaagaaaa | aaaccatttt | tttctaataa | 540 |
| tttagtggct | taaattaaat | ctttcgaata | attgaatgac | caaaatgtaa | ttttattaat | 600 |
| aatttaatga | cattggatgt | aatatactca | atctaatata | tcgagttaaa | aaaaaattc | 660 |
| tttggtacaa | ccagtgagtt | gtgtgaaatg | cttcttaatt | aactatatgt | tcaattatat | 720 |
| acattcaaaa | acatacaaaa | tagccctgaa | atatccaact | ttaatgggac | caatattatt | 780 |
| tttcatctat | cgtaacatac | tacaacagtt | ctatcaaaac | atacaaaaat | tattgttttt | 840 |
| ttctttttt | tttactcagg | acccgcttag | ttcgactcat | gaactagttt | attttggatg | 900 |
| tatattttt | tatataattt | cagtaaaata | tatttcaaac | attattgaag | caaagcaaga | 960 |
| atgtaagtgg | tagagcagac | agtatgttca | ctgatactga | tgtcatatat | atatatgttg | 1020 |
| ggatgcaagg | tttatagtga | taaacaagag | gttgaagatg | ttgtgtaagc | atggtgccaa | 1080 |
| gggaaaacat | gaagaattgg | accaccttct | ttacatgaat | ttggctgcat | ccttattcta | 1140 |
| acccattaat | atttaaatta | taaatattg | tcattaagat | aacatgtcat | ttccttctct | 1200 |

```
cattttctct gccaaatttg ttcttttttct ccttctttttt ttttttcctt tccatgtctt      1260
ttaaagttct gattttgaga gctgtctcct ctatctttta tcttatttac ataaaataaa      1320
taaatttcat cataaattta agtcccccaa aaaataaaac cataaaataa aataaaatct      1380
cagaaaaacc tcccgttcga aagcctcttt cttttcttcc acgggagctt aaagcttcgt      1440
cttgcaaaag tgggatagca cgaacttttg tgtgctttgt attgttatta attcttatat      1500
atttgccgtc aatccttata ttttgaaaaa aaatttatga tttaatctct gtatttaaaa      1560
ggttaaattt taagttttttc tttttttttt aatttaaaaa tctcagtcta accattaaca      1620
ttattaatat ttttctatca aaatttatga atttagcatt ttaattagat tgtcctcata      1680
tgtcatgata tattaagttg acaaattttg attaaaatta ctagcaacga taatgattgg      1740
attaggattg ttaaattaaa aaataagaat tgcatttttta aaaatatttt ttaaactgaa      1800
ccggtgatca aattggtcag atcatcggtt cacaggccta atcgtctaat cgattcgatt      1860
aaaaattaat aaaaattcaa aaaaaaatta aaatctcaat tcaaccagtt ctcaatctaa      1920
tcagttcaaa gccactttcc ggactaattc ccccaatcga ttcttggtcc ggtccaattc      1980
aaataatact aatttttttac ttttaaagca                                      2010

<210> SEQ ID NO 9
<211> LENGTH: 3143
<212> TYPE: DNA
<213> ORGANISM: Artificial
<220> FEATURE:
<223> OTHER INFORMATION: Nucleotide sequence corresponding to the
      inserted T-DNA in cotton event MON 88702.

<400> SEQUENCE: 9
agtcagcatc atcacaccaa aagttaggcc cgaatagttt gaaattagaa agctcgcaat        60
tgaggtctgt cgaccctgca ctaactataa cggtcctaag gtagcgatac actggcgcgc       120
caattctcag tccaaagcct caacaaggtc agggtacaga gtctccaaac cattagccaa       180
aagctacagg agatcaatga agaatcttca atcaaagtaa actactgttc cagcacatgc       240
atcatggtca gtaagtttca gaaaaagaca tccaccgaag acttaaagtt agtgggcatc       300
tttgaaagta atcttgtcaa catcgagcag ctggcttgtg gggaccagac aaaaaaggaa       360
tggtgcagaa ttgttaggcg cacctaccaa aagcatcttt gcctttattg caaagataaa       420
gcagattcct ctagtacaag tggggaacaa ataacgtgg aaaagagctg tcctgacagc       480
ccactcacta atgcgtatga cgaacgcagt gacgaccaca aaagaattag cttgcctgca       540
ggattagctt agatcgggct taattaaggc gcgccggcca gtcggccgc ggccgcaagc       600 ttacttgcga cagaaacagc tttgatatat tattactcac ccgttatcga tatggaatat       660
atactttaag aactcactaa atcatatcct tcatgtcggt ttaaagatta gtcacgtatc       720
tgcacattct gtaagtatag taatctcata aaaaacctgg tctctgttct ctgtgaatcc       780
ataggttatt gcactggcgt actactgtat atcatatttc cctggtggat catcgggaat       840
gaagttcctc agttctactc ttacctcctc tgtcttccga atgtttggga gatgagcttt       900
cgctttgacc tatgcaaaga aaataacttg attctctcgt gtataaagaa agatgaaaga       960
tcttcaacag tggttaaatg acaaatctgg taaaatatgt tggtccaatg gctcaaagac      1020
agttttgtta taaatttcct atattgatac tttctgctaa attggttcaa aacttcaaat      1080
cactagccac tggatgaggt atggaacttg aagagttgct tggtggatac attctctaat      1140
ctagggtaag tcgttagctt caatgtctta ctgtgaatta ttacatcaga attaagaaag      1200
```

```
ttattacacg tatgttttca ctgagtttac tacactggca atgtggcata catctcttac    1260
tgcaaattgc agacaagtgg tcaatcaaat cttttttagt tgggcccaaa atgtctgtta    1320
ttggatacgt tgggccttaa aatggccccc atcagtcaaa aacatcactg cttggagaag    1380
gatctagaaa aacttgcaag ttagttcaaa caaaataaag gaaaaagaac gatctagaag    1440
aaagaaaaaa aaaggaaaag aaaccctttat ggaggttccc acaccactct atatataata   1500
acatccttct cctaaatccc gcatcagtac ttctctctgc tctcaagata attttgttct    1560
ctcaatttca ttcttaaacc ctagttcttc gattttttcc gatctacgac acctgcaggc    1620
ctcagcgctg tgcctgttgc gatcgcccat ggctatccta gacctttaagt ccctcgtgct   1680 gaacgccatt aactactggg gccctaagaa caacaacggc atccagggcg gtgacttcgg   1740
ctaccccatc tctgagaagc agatcgacac tagcatcatt acctccaccc accctcgctt    1800 gatccccac gatcttacta tcccgcagaa ccttgagacc atcttcacca caacgcaggt     1860
gctcaccaat aacactgacc tccagcaatc ccagaccgtg agctttgcga agaagaccac    1920
taccacgacc gcaactagca cgaccaacgg ttggacagaa ggaggcaaga tcagcgacac    1980
gctggaggag aaagtttcgg ttagcattcc gttcatcggt gagggtggcg ggaagaactc    2040
gactaccata gaggccaact tcgcacacaa ctctagcacc actacctccc aggaagcaag    2100
cactgacatt gagtggaaca ttagccaacc ggtccttgtg cctccccgca aacaggttgt    2160
tgccactctc gttatcatgg gtggcaactt cactattcct atggatctta tgactaccat    2220
tgactctact gagcactact ctggctaccc cattctcact tggatctctt ctcctgacaa    2280
tagctacagc ggtcgattca tgtcatggta cttcgctaac tggccgaatc tcccttctgg    2340
ctttggtcct cttaactctg ataacactgt gacctacact ggctctgtcg tcagtcaggt    2400
ctctgccggt gtgtacgcaa ctgttcgctt cgatcagtat gacatccata atctctggac    2460
tattgagaag acctggtacg ctcgtcatgc gacgcttcac aacggcaaga agatcagcat    2520
caataacgtg acagaaatgg cccctaccag cccgatcaag actaactgag cgatcgccag    2580
cagaacacgc gctgagggcc caaatcacca gtctctctct acaaatctat ctctctctat    2640
ttttctccag aataatgtgt gagtagttcc cagataaggg aattagggtt cttataggt     2700 ttcgctcatg tgttgagcat ataagaaacc cttagtatgt atttgtattt gtaaaatact    2760
tctatcaata aaatttctaa ttcctaaaac caaaatccag tcaaatccta ccacctcatt    2820
taaatagagt gaggttgatt tgcggccgca cgtcctgctt ggcctactag gccaacgcag    2880
gcgctggccg tgacggccac gagcgaacta ggccttgggc cgcatcgatc gtgaagtttc    2940
tcatctaagc ccccatttgg acgtgaatgt agacacgtcg aaataaagat ttccgaatta    3000
gaataatttg tttattgctt tcgcctataa atacgacgga tcgtaatttg tcgttttatc    3060
aaaatgtact ttcattttat aataacgctg cggacatcta cattttttgaa ttgaaaaaaa   3120 attggtaatt actctttctt ttt                                            3143
```

<210> SEQ ID NO 10
<211> LENGTH: 6804
<212> TYPE: DNA
<213> ORGANISM: Artificial
<220> FEATURE:
<223> OTHER INFORMATION: Nucleotide sequence corresponding to the contig
      nucleotide sequence of the 5' genomic flanking DNA nucleotide
      sequence, the inserted T-DNA nucleotide sequence in event MON
      88702, and the 3' genomic flanking DNA nucleotide sequence.
<220> FEATURE:
<221> NAME/KEY: misc_feature
<222> LOCATION: (1)..(1651)

<223> OTHER INFORMATION: The 5' genomic flanking sequence represented by
      SEQ ID NO: 7.
<220> FEATURE:
<221> NAME/KEY: misc_feature
<222> LOCATION: (1652)..(4794)
<223> OTHER INFORMATION: The inserted T-DNA nucleotide sequence in event
      MON 88702 represented as SEQ ID NO: 9.
<220> FEATURE:
<221> NAME/KEY: misc_feature
<222> LOCATION: (4795)..(6804)
<223> OTHER INFORMATION: The 3' genomic flanking DNA nucleotide sequence
      represented as SEQ ID NO: 8.

<400> SEQUENCE: 10

```
gttatatata taatttaaaa cttttccctt tggttggaat aacaactaac attaaatttg      60
aacctctttt attttcctct atagtttttc ttttatggaa aagtgattgt accctccttc     120
aattgtaaaa aggtgaaggg ggaatcaatg gtcatctttt gcttgattgg tgcttctccc     180
aaagtcatct aatcaaataa agatagagaa aaaaaagggg ggagggactt gaaaaaagta     240
tacttgcttt gagtgcaaga agctaccaaa acttttttaga tggaccaaaa ataaaaaagg     300
tggtagccct aaaatctccc cccccccaa gctgtgagtg acttgttatt tttatgtttg     360
cttaaagttt gacctttcat gacatgatta tcacatactt gattgtatac atgtgtgtgt     420
aaaaaagtta aatgtggggt ttggcttgca ctagtgaaaa gaattatggg acccttttgtc     480
tcatgatata ccatcaatta tcccttggaa gaggctcttt tttaaattat tgttattatt     540
tacatcaact atatgatcat ggatggatca attgtgatt tgaactttgg gggtgccttt     600
tttgatgttc taataactca aataaaaacg agactctagc aattagatga tgagaagaca     660
attaagggtg tttttttctt tctgaagatc cctttaaatg gggtcattgg ttgatatcta     720
gcaatccttg aagcaaatat atatttatat attatatgga gagagaaagc attttaaatg     780
atggttctta tatcattgag gtatatagtg ggagaatcat attttttcctt gtgaaggaac     840
caacaacaaa gcaagcaaac accttttgat aattatggta agataaaata ataataaggc     900
ataatgacta actaagctct taacatttat atattctgtc gatttaatcc ttattctttt     960
ttgagctaaa tttgactatc aaccttttcaa aaataattga atgttgcctt tttttttaatg    1020
gaaatacaaa ctaaaacgtt aaattttttaa acataacaac ccaaatggca atccatttgt    1080
atttcatact aatttttaa aattttaaga acttttttata tatatatttt ttagattttg    1140
aattcgcttt tatttttaa tcatttgtta acataacgta tacaacaaaa tagtgctatg    1200
tcagcatgaa gtatatatgg actgccatgt gggttgtcat gtcaacatag ataaaaaatt    1260
aattttttag tcagtatttc catttaaaag aaaaacaatt tgactcttttt taaaagacta    1320
atgatttaat ttaactaaaa aaaataaggg tcaaattgat caaatatata aatattgagg    1380
gctgaattta tcatcatacc taatactaat cttaagagag agagagagtg gagatagata    1440
gaatgatgaa aagagatcta acaaggtttc aagtgtgggg aaaaaaagtt taggctaatg    1500
agaccacctt ttcttttta attaattaaa aggaattagt atggtatcat atgcttaagg    1560
agtgggtatg caaaagacaa aaacccaagg agcttccacc agaaatttcc tctttttttca    1620
atatgaaaga taaataata gaaaaaaata tagtcagcat catcacacca aaagttaggc    1680
ccgaatagtt tgaaattaga aagctcgcaa ttgaggtctg tcgaccctgc actaactata    1740
acggtcctaa ggtagcgata cactggcgcg ccaattctca gtccaaagcc tcaacaaggt    1800
cagggtacag agtctccaaa ccattagcca aaagctacag gagatcaatg aagaatcttc    1860
aatcaaagta aactactgtt ccagcacatg catcatggtc agtaagtttc agaaaaagac    1920
```

```
atccaccgaa gacttaaagt tagtgggcat ctttgaaagt aatcttgtca acatcgagca    1980
gctggcttgt ggggaccaga caaaaaagga atggtgcaga attgttaggc gcacctacca    2040
aaagcatctt tgcctttatt gcaaagataa agcagattcc tctagtacaa gtggggaaca    2100
aaataacgtg gaaagagct gtcctgacag cccactcact aatgcgtatg acgaacgcag     2160
tgacgaccac aaaagaatta gcttgcctgc aggattagct tagatcgggc ttaattaagg    2220
cgcgccggcc aagtcggccg cggccgcaag cttacttgcg acagaaacag ctttgatata    2280
ttattactca cccgttatcg atatggaata tatactttaa gaactcacta aatcatatcc    2340
ttcatgtcgg tttaaagatt agtcacgtat ctgcacattc tgtaagtata gtaatctcat    2400
aaaaaacctg gtctctgttc tctgtgaatc cataggttat tgcactggcg tactactgta    2460
tatcatattt ccctggtgga tcatcgggaa tgaagttcct cagttctact cttacctcct    2520
ctgtcttccg aatgtttggg agatgagctt tcgctttgac ctatgcaaag aaaataactt    2580
gattctctcg tgtataaaga aagatgaaag atcttcaaca gtggttaaat gacaaatctg    2640
gtaaaatatg ttggtccaat ggctcaaaga cagttttgtt ataaatttcc tatattgata    2700 cttctctgcta aattggttca aaacttcaaa tcactagcca ctggatgagg tatgaacct     2760 gaagagttgc ttggtggata cattctctaa tctagggtaa gtcgttagct tcaatgtctt    2820
actgtgaatt attacatcag aattaagaaa gttattacac gtatgttttc actgagttta    2880
ctacactggc aatgtggcat acatctctta ctgcaaattg cagacaagtg gtcaatcaaa    2940
tcttttttag ttgggcccaa aatgtctgtt attggatacg ttgggcctta aaatggcccc    3000
catcagtcaa aaacatcact gcttggagaa ggatctagaa aaacttgcaa gttagttcaa    3060
acaaaataaa ggaaaagaa cgatctagaa gaaagaaaaa aaaggaaaa gaaacccta      3120 tggaggttcc cacaccactc tatatataat aacatccttc tcctaaatcc cgcatcagta    3180
cttctctctg ctctcaagat aattttgttc tctcaatttc attcttaaac cctagttctt    3240 cgatttttc cgatctacga cacctgcagg cctcagcgct gtgcctgttg cgatcgccca     3300
tggctatcct agaccttaag tccctcgtgc tgaacgccat taactactgg ggccctaaga    3360
acaacaacgg catccagggc ggtgacttcg gctaccccat ctctgagaag cagatcgaca    3420
ctagcatcat tacctccacc cacccctcgct tgatccccca cgatcttact atcccgcaga    3480
accttgagac catcttcacc acaacgcagg tgctcaccaa taacactgac ctccagcaat    3540
cccagaccgt gagctttgcg aagaagacca ctaccacgac cgcaactagc acgaccaacg    3600
gttggacaga aggaggcaag atcagcgaca cgctggagga aaagtttcg gttagcattc      3660 cgttcatcgg tgagggtggc gggaagaact cgactaccat agaggccaac ttcgcacaca    3720
actctagcac cactacctcc caggaagcaa gcactgacat tgagtggaac attagccaac    3780
cggtccttgt gcctccccgc aaacaggttg ttgccactct cgttatcatg ggtggcaact    3840
tcactattcc tatggatctt atgactacca ttgactctac tgagcactac tctggctacc    3900
ccattctcac ttggatctct tctcctgaca atagctacag cggtcgattc atgtcatggt    3960
acttcgctaa ctggccgaat ctcccttctg gctttggtcc tcttaactct gataacactg    4020
tgacctacac tggctctgtc gtcagtcagg tctctgccgg tgtgtacgca actgttcgct    4080
tcgatcagta tgacatccat aatctctgga ctattgagaa gacctggtac gctcgtcatg    4140
cgacgcttca caacggcaag aagatcagca tcaataacgt gacagaaatg gcccctacca    4200
gcccgatcaa gactaactga gcgatcgcca gcagaacacg cgctgagggc ccaaatcacc    4260
agtctctctc tacaaatcta tctctctcta ttttttctcca gaataatgtg tgagtagttc    4320
```

```
ccagataagg gaattagggt tcttataggg tttcgctcat gtgttgagca tataagaaac    4380
ccttagtatg tatttgtatt tgtaaaatac ttctatcaat aaaatttcta attcctaaaa    4440
ccaaaatcca gtcaaatcct accacctcat ttaaatagag tgaggttgat ttgcggccgc    4500
acgtcctgct tggcctacta ggccaacgca ggcgctggcc gtgacggcca cgagcgaact    4560
aggccttggg ccgcatcgat cgtgaagttt ctcatctaag cccccatttg acgtgaatg    4620 tagacacgtc gaaataaaga tttccgaatt agaataattt gtttattgct ttcgcctata    4680
aatacgacgg atcgtaattt gtcgttttat caaaatgtac tttcatttta taataacgct    4740
gcggacatct acattttga attgaaaaaa aattggtaat tactctttct tttttcaata    4800
taaacatggg aaatttgaaa cttccttttt attattctaa aagtattaa ttccataatg    4860 aatgcatgaa ggagttgttc aacaaattaa tgaccaaagg tgaaattaaa agatttgtac    4920
tcagaaatta attttttaatt taagtcgtga dacacgcttt tgaaatgcat tgaagttttt    4980
tttttttaat taaatacaaa tttccagata atgttaggga caaggcaaac tagatggaaa    5040
gacagtcatt gaactaataa gtaacagtaa gaatatgtgt ctttcttttt attataacat    5100
acaaacactt agacattatt aaaacagccc aagtttgtcg tttacaaaga ttgcaatctc    5160
catatcatga caatacaata tactccatat tgattgcatt cataaaatat cattttaccct    5220 cccttacctt aaatcccatt cattcattag catgagattt caagtaaaat tatgaactga    5280
aaattagcca aatttattca aaatttgaag aaaaaaaacc attttttcta ataatttagt    5340
ggcttaaatt aaatctttcg aataattgaa tgaccaaaat gtaattttat taataattta    5400
atgacattgg atgtaatata ctcaatctaa tatatcgagt taaaaaaaaa attctttggt    5460
acaaccagtg agttgtgtga aatgcttctt aattaactat atgttcaatt atatacattc    5520
aaaaacatac aaaatagccc tgaaatatcc aactttaatg ggaccaatat tattttcat    5580 ctatcgtaac atactacaac agttctatca aaacatacaa aaattattgt tttttcttt    5640 tttttttact caggacccgc ttagttcgac tcatgaacta gtttattttg gatgtatatt    5700
tttttatata atttcagtaa aatatatttc aaacattatt gaagcaaagc aagaatgtaa    5760
gtggtagagc agacagtatg ttcactgata ctgatgtcat atatatatat gttgggatgc    5820
aaggtttata gtgataaaca agaggttgaa gatgttgtgt aagcatggtg ccaagggaaa    5880
acatgaagaa ttggaccacc ttcttacat gaatttggct gcatccttat tctaacccat    5940
taatatttaa attataaaat attgtcatta agataacatg tcatttcctt ctctcatttt    6000
ctctgccaaa tttgttcttt ttctccttct tttttttttt cctttccatg tcttttaaag    6060
ttctgatttt gagagctgtc tcctctatct tttatcttat ttacataaaa taaataaatt    6120
tcatcataaa tttaagtccc ccaaaaaata aaaccataaa ataaataaa atctcagaaa    6180 aacctcccgt tcgaaagcct ctttcttttc ttccacggga gcttaaagct tcgtcttgca    6240
aaagtgggat agcacgaact tttgtgtgct ttgtattgtt attaattctt atatatttgc    6300
cgtcaatcct tatatttga aaaaaaattt atgatttaat ctctgtattt aaaaggttaa    6360
attttaagtt tttctttttt ttttaattta aaaatctcag tctaaccatt aacattatta    6420 atattttct atcaaaattt atgaatttag catttttaatt agattgtcct catatgtcat    6480
gatatattaa gttgacaaat tttgattaaa attactagca acgataatga ttggattagg    6540
attgttaaat taaaaaataa gaattgcatt tttaaaaata ttttttaaac tgaaccggtg    6600
atcaaattgg tcagatcatc ggttcacagg cctaatcgtc taatcgattc gattaaaaat    6660
```

```
taataaaaat tcaaaaaaaa attaaaatct caattcaacc agttctcaat ctaatcagtt    6720
caaagccact ttccggacta attccccaa tcgattcttg gtccggtcca attcaaataa    6780
tactaatttt ttacttttaa agca                                          6804
```

<210> SEQ ID NO 11
<211> LENGTH: 25
<212> TYPE: DNA
<213> ORGANISM: Artificial
<220> FEATURE:
<223> OTHER INFORMATION: Nucleotide sequence corresponding to a thermal
      amplification primer, SQ21940 used to identify cotton event MON
      88702 DNA in a sample.

<400> SEQUENCE: 11

```
ctttcatttt ataataacgc tgcgg                                           25
```

<210> SEQ ID NO 12
<211> LENGTH: 24
<212> TYPE: DNA
<213> ORGANISM: Artificial
<220> FEATURE:
<223> OTHER INFORMATION: Nucleotide sequence corresponding to a thermal
      amplification primer, SQ-50210 used to identify cotton event MON
      88702 DNA in a sample.

<400> SEQUENCE: 12

```
aggaagtttc aaatttccca tgtt                                            24
```

<210> SEQ ID NO 13
<211> LENGTH: 22
<212> TYPE: DNA
<213> ORGANISM: Artificial
<220> FEATURE:
<223> OTHER INFORMATION: Nucleotide sequence corresponding to a probe,
      PB10344 used to identify cotton event MON 88702 DNA in a sample.

<400> SEQUENCE: 13

```
acatctacat ttttgaattg aa                                              22
```

<210> SEQ ID NO 14
<211> LENGTH: 23
<212> TYPE: DNA
<213> ORGANISM: Artificial
<220> FEATURE:
<223> OTHER INFORMATION: Nucleotide sequence corresponding to a thermal
      amplification primer, SQ22496 used as an internal control in the
      event assay for MON 88702.

<400> SEQUENCE: 14

```
gaagaagcac cctctcattt acg                                             23
```

<210> SEQ ID NO 15
<211> LENGTH: 19
<212> TYPE: DNA
<213> ORGANISM: Artificial
<220> FEATURE:
<223> OTHER INFORMATION: Nucleotide sequence corresponding to a thermal
      amplification primer, SQ22497 used as an internal control in the
      event assay for MON 88702.

<400> SEQUENCE: 15

```
tggcagcaca gcagatctg                                                  19
```

<210> SEQ ID NO 16
<211> LENGTH: 20
<212> TYPE: DNA

```
<213> ORGANISM: Artificial
<220> FEATURE:
<223> OTHER INFORMATION: Nucleotide sequence corresponding to a probe,
      PB13032 used as an internal control in the event assay for MON
      88702.

<400> SEQUENCE: 16
tgcgtccaat gcctgctcgc                                                    20

<210> SEQ ID NO 17
<211> LENGTH: 24
<212> TYPE: DNA
<213> ORGANISM: Artificial
<220> FEATURE:
<223> OTHER INFORMATION: Nucleotide sequence corresponding to a thermal
      amplification primer, SQ50844 used in the zygosity assay for event
      MON 88702 DNA in a sample.

<400> SEQUENCE: 17
tcgcctataa atacgacgga tcgt                                               24

<210> SEQ ID NO 18
<211> LENGTH: 20
<212> TYPE: DNA
<213> ORGANISM: Artificial
<220> FEATURE:
<223> OTHER INFORMATION: Nucleotide sequence corresponding to a probe,
      PB50279 used to identify cotton event MON 88702 allele in a sample
      for the zygosity assay.

<400> SEQUENCE: 18
aacgctgcgg acatctacat                                                    20

<210> SEQ ID NO 19
<211> LENGTH: 26
<212> TYPE: DNA
<213> ORGANISM: Artificial
<220> FEATURE:
<223> OTHER INFORMATION: Nucleotide sequence corresponding to a thermal
      amplifcation primer, SQ50843 used in the zygosity assay for event
      MON 88702 DNA in a sample which hybridizes to both the wild-type
      and MON 88702 alleles.

<400> SEQUENCE: 19
caactccttc atgcattcat tatgga                                             26

<210> SEQ ID NO 20
<211> LENGTH: 25
<212> TYPE: DNA
<213> ORGANISM: Artificial
<220> FEATURE:
<223> OTHER INFORMATION: Nucleotide sequence corresponding to a thermal
      amplifcation primer, SQ50842 used int he zygosity assay for event
      MON 88702 DNA in a sample which hybridizes to only the wild-type
      DNA allele that does not contain the inserted MON 88702 transgene
      cassette.

<400> SEQUENCE: 20
ggtccctcca cagtccacaa actat                                              25

<210> SEQ ID NO 21
<211> LENGTH: 21
<212> TYPE: DNA
<213> ORGANISM: Artificial
<220> FEATURE:
<223> OTHER INFORMATION: Nucleotide sequence corresponding to a probe,
      PB50278 used to identify the wild-type allel in the zygosity assay
      for event MON 88702 DNA in a sample.
```

<400> SEQUENCE: 21
ttctacatgt acttgctacc a                                              21

<210> SEQ ID NO 22
<211> LENGTH: 101
<212> TYPE: DNA
<213> ORGANISM: Artificial
<220> FEATURE:
<223> OTHER INFORMATION: Nucleotide sequence representing the junction
      between the right T-DNA border sequence and the FMV 35S enhancer
      sequence within the transgene cassette used to transform DP393
      cotton to produce cotton event MON 88702.

<400> SEQUENCE: 22
tcgcaattga ggtctgtcga ccctgcacta actataacgg tcctaaggta gcgatacact     60
ggcgcgccaa ttctcagtcc aaagcctcaa caaggtcagg g                        101

<210> SEQ ID NO 23
<211> LENGTH: 77
<212> TYPE: DNA
<213> ORGANISM: Artificial
<220> FEATURE:
<223> OTHER INFORMATION: Nucleotide sequence representing the junction
      between the Arabidopsis thaliana HSP81.2 5' UTR and the TIC834_16
      coding sequence within the transgene cassette used to transform
      DP393 cotton to produce cotton event MON 88702.

<400> SEQUENCE: 23
ttttttccga tctacgacac ctgcaggcct cagcgctgtg cctgttgcga tcgcccatgg     60
ctatcctaga ccttaag                                                   77

<210> SEQ ID NO 24
<211> LENGTH: 97
<212> TYPE: DNA
<213> ORGANISM: Artificial
<220> FEATURE:
<223> OTHER INFORMATION: Nucleotide sequence representing the junction
      between the TIC834_16 coding sequence and the 3' UTR within the
      transgene cassette used to transform DP393 cotton to produce
      cotton event MON 88702.

<400> SEQUENCE: 24
ccctaccagc ccgatcaaga ctaactgagc gatcgccagc agaacacgcg ctgagggccc     60
aaatcaccag tctctctcta caaatctatc tctctct                             97

<210> SEQ ID NO 25
<211> LENGTH: 200
<212> TYPE: DNA
<213> ORGANISM: Artificial
<220> FEATURE:
<223> OTHER INFORMATION: Nucleotide sequence representing the junction
      between the 3' UTR and the left T-DNA border sequence within the
      transgene cassette used to transform DP393 cotton to produce
      cotton event MON 88702.

<400> SEQUENCE: 25
atttctaatt cctaaaacca aaatccagtc aaatcctacc acctcattta aatagagtga     60
ggttgatttg cggccgcacg tcctgcttgg cctactaggc caacgcaggc gctggccgtg    120
acggccacga gcgaactagg ccttgggccg catcgatcgt gaagtttctc atctaagccc    180
ccatttggac gtgaatgtag                                                200

<210> SEQ ID NO 26
<211> LENGTH: 921

```
<212> TYPE: DNA
<213> ORGANISM: Artificial
<220> FEATURE:
<223> OTHER INFORMATION: Nucleotide sequence representing the TIC834_16
      coding sequence within the transgene cassette used to transform
      DP393 cotton to produce cotton event MON 88702.

<400> SEQUENCE: 26
atggctatcc tagaccttaa gtccctcgtg ctgaacgcca ttaactactg gggccctaag      60
aacaacaacg gcatccaggg cggtgacttc ggctaccca tctctgagaa gcagatcgac     120
actagcatca ttacctccac ccaccctcgc ttgatccccc acgatcttac tatcccgcag     180
aaccttgaga ccatcttcac cacaacgcag gtgctcacca ataacactga cctccagcaa     240
tcccagaccg tgagctttgc gaagaagacc actaccacga ccgcaactag cacgaccaac     300
ggttggacaa aaggaggcaa gatcagcgac acgctggagg agaaagtttc ggttagcatt     360
ccgttcatcg gtgagggtgg cggaagaac tcgactacca tagaggccaa cttcgcacac     420
aactctagca ccactacctc ccaggaagca agcactgaca ttgagtggaa cattagccaa     480
ccggtccttg tgcctccccg caaacaggtt gttgccactc tcgttatcat gggtggcaac     540
ttcactattc ctatggatct tatgactacc attgactcta ctgagcacta ctctggctac     600
cccattctca cttggatctc ttctcctgac aatagctaca gcggtcgatt catgtcatgg     660
tacttcgcta actggccgaa tctcccttct ggctttggtc ctcttaactc tgataacact     720
gtgacctaca ctggctctgt cgtcagtcag gtctctgccg gtgtgtacgc aactgttcgc     780
ttcgatcagt atgacatcca taatctctgg actattgaga agacctggta cgctcgtcat     840
gcgacgcttc acaacggcaa gaagatcagc atcaataacg tgacagaaat ggcccctacc     900
agcccgatca agactaactg a                                               921

<210> SEQ ID NO 27
<211> LENGTH: 3598
<212> TYPE: DNA
<213> ORGANISM: Artificial
<220> FEATURE:
<223> OTHER INFORMATION: Nucleotide sequence representing the transgene
      cassette comprised within the binary plasmid transformation vector
      used to transform DP393 cotton to produce cotton event MON 88702.

<400> SEQUENCE: 27
cgaagctcgg tcccgtgggt gttctgtcgt ctcgttgtac aacgaaatcc attcccattc      60
cgcgctcaag atggcttccc ctcggcagtt catcagggct aaatcaatct agccgacttg     120
tccggtgaaa tgggctgcac tccaacagaa acaatcaaac aaacatacac agcgacttat     180
tcacacgagc tcaaattaca acggtatata tcctgccagt cagcatcatc acaccaaaag     240
ttaggcccga atagtttgaa attagaaagc tcgcaattga ggtctgtcga ccctgcacta     300
actataacgg tcctaaggta gcgatacact ggcgcgccaa ttctcagtcc aaagcctcaa     360
caaggtcagg gtacagagtc tccaaaccat tagccaaaag ctacaggaga tcaatgaaga     420
atcttcaatc aaagtaaact actgttccag cacatgcatc atggtcagta agtttcagaa     480
aaagacatcc accgaagact aaagttagt gggcatcttt gaaagtaatc ttgtcaacat     540
cgagcagctg gcttgtgggg accagacaaa aaaggaatgg tgcagaattg ttaggcgcac     600
ctaccaaaag catctttgcc tttattgcaa agataaagca gattcctcta gtacaagtgg     660
ggaacaaaat aacgtggaaa agagctgtcc tgacagccca ctcactaatg cgtatgacga     720
acgcagtgac gaccacaaaa gaattagctt gcctgcagga ttagcttaga tcgggcttaa     780
```

| | |
|---|---:|
| ttaaggcgcg ccggccaagt cggccgcggc cgcaagctta cttgcgacag aaacagcttt | 840 |
| gatatattat tactcacccg ttatcgatat ggaatatata ctttaagaac tcactaaatc | 900 |
| atatccttca tgtcggttta agattagtc acgtatctgc acattctgta agtatagtaa | 960 |
| tctcataaaa aacctggtct ctgttctctg tgaatccata ggttattgca ctggcgtact | 1020 |
| actgtatatc atatttccct ggtggatcat cgggaatgaa gttcctcagt tctactctta | 1080 |
| cctcctctgt cttccgaatg tttgggagat gagctttcgc tttgacctat gcaaagaaaa | 1140 |
| taacttgatt ctctcgtgta taagaaaga tgaaagatct tcaacagtgg ttaaatgaca | 1200 |
| aatctggtaa atatgttgg tccaatggct caaagacagt tttgttataa atttcctata | 1260 |
| ttgatacttt ctgctaaatt ggttcaaaac ttcaaatcac tagccactgg atgaggtatg | 1320 |
| gaacttgaag agttgcttgg tggatacatt ctctaatcta gggtaagtcg ttagcttcaa | 1380 |
| tgtcttactg tgaattatta catcagaatt aagaaagtta ttacacgtat gttttcactg | 1440 |
| agtttactac actggcaatg tggcatacat ctcttactgc aaattgcaga caagtggtca | 1500 |
| atcaaatctt ttttagttgg gcccaaaatg tctgttattg gatacgttgg gccttaaaat | 1560 |
| ggcccccatc agtcaaaaac atcactgctt ggagaaggat ctagaaaaac ttgcaagtta | 1620 |
| gttcaaacaa aataaaggaa aaagaacgat ctagaagaaa gaaaaaaaaa ggaaaagaaa | 1680 |
| cccttatgga ggttcccaca ccactctata tataataaca tccttctcct aaatcccgca | 1740 |
| tcagtacttc tctctgctct caagataatt ttgttctctc aatttcattc ttaaaccta | 1800 |
| gttcttcgat tttttccgat ctacgacacc tgcaggcctc agcgctgtgc ctgttgcgat | 1860 |
| cgcccatggc tatcctagac cttaagtccc tcgtgctgaa cgccattaac tactggggcc | 1920 |
| ctaagaacaa caacggcatc cagggcggtg acttcggcta ccccatctct gagaagcaga | 1980 |
| tcgacactag catcattacc tccacccacc ctcgcttgat cccccacgat cttactatcc | 2040 |
| cgcagaacct tgagaccatc ttcaccacaa cgcaggtgct caccaataac actgacctcc | 2100 |
| agcaatccca daccgtgagc tttgcgaaga agaccactac cacgaccgca actagcacga | 2160 |
| ccaacggttg dacagaagga ggcaagatca gcgacacgct ggaggagaaa gtttcggtta | 2220 |
| gcattccgtt catcggtgag ggtggcggga agaactcgac taccatagag gccaacttcg | 2280 |
| cacacaactc tagcaccact acctcccagg aagcaagcac tgacattgag tggaacatta | 2340 |
| gccaaccggt cctttgtgcct ccccgcaaac aggttgttgc cactctcgtt atcatgggtg | 2400 |
| gcaacttcac tattcctatg gatcttatga ctaccattga ctctactgag cactactctg | 2460 |
| gctacccat tctcacttgg atctcttctc ctgacaatag ctacagcggt cgattcatgt | 2520 |
| catggtactt cgctaactgg ccgaatctcc cttctggctt tggtcctctt aactctgata | 2580 |
| acactgtgac ctacactggc tctgtcgtca gtcaggtctc tgccggtgtg tacgcaactg | 2640 |
| ttcgcttcga tcagtatgac atccataatc tctggactat tgagaagacc tggtacgctc | 2700 |
| gtcatgcgac gcttcacaac ggcaagaaga tcagcatcaa taacgtgaca gaaatggccc | 2760 |
| ctaccagccc gatcaagact aactgagcga tcgccagcag aacacgcgct gagggcccaa | 2820 |
| atcaccagtc tctctctaca aatctatctc tctctatttt tctccagaat aatgtgtgag | 2880 |
| tagttcccag ataagggaat tagggttctt atagggtttc gctcatgtgt tgagcatata | 2940 |
| agaaacccctt agtatgtatt tgtatttgta aaatacttct atcaataaaa tttctaattc | 3000 |
| ctaaaaccaa aatccagtca aatcctacca cctcatttaa atagagtgag gttgatttgc | 3060 |
| ggccgcacgt cctgcttggc ctactaggcc aacgcaggcg ctggccgtga cggccacgag | 3120 |
| cgaactaggc cttgggccgc atcgatcgtg aagtttctca tctaagcccc catttggacg | 3180 |

```
tgaatgtaga cacgtcgaaa taaagatttc cgaattagaa taatttgttt attgctttcg    3240
cctataaata cgacggatcg taatttgtcg ttttatcaaa atgtactttc attttataat    3300
aacgctgcgg acatctacat ttttgaattg aaaaaaaatt ggtaattact ctttcttttt    3360
ctccatattg accatcatac tcattgctga tccatgtaga tttcccggac atgaagccat    3420
ttacaattga atatatcctg ccgccgctgc cgctttgcac ccggtggagc ttgcatgttg    3480
gtttctacgc agaactgagc cggttaggca gataatttcc attgagaact gagccatgtg    3540
caccttcccc ccaacacggt gagcgacggg gcaacggagt gatccacatg ggactttt     3598
```

COTTON TRANSGENIC EVENT MON 88702 AND METHODS FOR DETECTION AND USES THEREOF

REFERENCE TO RELATED APPLICATION

This application is a divisional of U.S. application Ser. No. 15/341,968, filed Nov. 2, 2016 (pending) which application claims the benefit of U.S. Provisional Application No. 62/249,758, filed Nov. 2, 2015, each of which is herein incorporated by reference in its entirety.

INCORPORATION OF SEQUENCE LISTING

The sequence listing contained in the file named MONS405US-sequence_listing.txt is 33.3 kilobytes (size as measured in Microsoft Windows®), was created on Oct. 25, 2016, is filed herewith by electronic submission, and is incorporated by reference.

FIELD OF THE INVENTION

The invention relates to a transgenic cotton event referred to as MON 88702. The event provides resistance from *Hemipteran* and *Thysanopteran* infestations of cotton by providing a unique insecticidal toxin protein not previously available in cotton plants. This insecticidal toxin protein is highly efficacious for controlling *Hemipteran* and *Thysanopteran* species infestations characteristic to cotton plants. The invention also relates to cotton plants, plant parts, plant seeds, plant cells, progeny plants, agricultural products, and methods related to event MON 88702, and provides nucleotide molecules that are unique to the event, created in connection with the insertion of transgenic DNA into the genome of a *Gossypium hirsutum* (cotton) cell, and useful for detecting the presence of this event in biological samples containing cotton nucleic acids.

BACKGROUND OF THE INVENTION

Cotton is an important crop in many areas of the world, and biotechnology methods have been applied to produce cotton varieties with desirable traits. One such desirable trait is insect resistance. The expression of an insect resistance transgene in a cotton plant can confer the desirable trait of insect resistance. Many different factors influence the expression of a transgene, including the orientation and composition of the cassettes driving expression of the individual genes transferred to the plant chromosome, the chromosomal location of the transgene insert, and the genomic result of the transgene insertion. For example, there can be variation in the level and pattern of transgene expression among individual events that differ in the chromosomal insertion site of the transgene, but are otherwise identical. There can also be phenotypic and agronomic differences between events.

To make a transgenic cotton plant containing a single transformation event, a portion of a recombinant DNA construct is transferred into the genome of a cotton cell, and the cotton cell is subsequently grown into a plant. A cotton cell into which the event is initially transferred is regenerated to produce the R0 generation. The R0 plant and progeny plants from the R0 plant can be tested for any desired trait(s), but the effectiveness of the event can be impacted by cis and/or trans factors relative to the integration site in the transformation event. The phenotype conferred by the event can also be impacted by the size and design of the DNA construct, which can vary by the combination of genetic elements in an expression cassette, number of transgenes, number of expression cassettes, and configuration of such elements and such cassettes. Identifying an event with desirable traits can be further complicated by factors such as plant developmental, diurnal, temporal, or spatial patterns of transgene expression, or by extrinsic factors such as environmental plant growth conditions, water availability, nitrogen availability, heat, or stress. Thus, the ability to obtain an event conferring a desirable level of transgene expression and a desirable set of phenotypic and agronomic traits is not readily predictable.

Due to these numerous factors that have an effect on the efficacy of an event, it is necessary to produce and analyze a large number of individual plant cell transformation events in order to create an event having proper expression of the desirable trait and optimal phenotypic and agricultural characteristics suitable for commercial success. Creating a commercially valuable transgenic event requires extensive molecular characterization, as well as greenhouse and field trials with numerous experimental events over multiple years, in multiple locations, and under a variety of conditions. A significant amount of efficacy, phenotypic, and molecular data is collected, and the resulting data and observations are then analyzed by teams of scientists and agronomists with the goal of selecting one or more commercially suitable events. Such an event, once selected, is then used for introgression of the desirable transgenic trait into other genetic backgrounds using plant breeding methods, thus producing a number of different cotton crop varieties that contain the desirable trait and are suitably adapted to specific local agronomic conditions.

Transgenic cotton plants are known in the art, but only plants expressing *Lepidopteran* toxins or herbicide tolerance genes have been produced. There are no commercial transgenic cotton plants for the control of *Hemipteran* (such as *lygus*, cotton fleahopper and verde plant bug) and *Thysanopteran* (such as *thrips*) pests of cotton crops.

*Lygus* species can threaten a cotton crop from earliest squaring through cutout and final boll set. The insects pierce squares and damage anthers and other tissues. When squares are less than 5 millimeters long, they shrivel, turn brown, and drop from the plant. Damage to larger squares may be to anthers, styles, and stigma, and may interfere with fertilization. If many squares drop, the plant may put its energy resources into vegetative growth, resulting in tall, spindly plants with reduced yields. *Lygus* species also feed on and destroy terminal meristems, causing bushy plants. If *lygus* pierce the wall of young bolls (typically less than ten days old) and feed on young seeds, these seeds may fail to develop. Lint around the injured seeds is stained yellow, and may not mature normally.

Cotton fleahopper can cause excessive loss of cotton squares, resulting in reduced yield and harvest delays. Cotton fleahopper is a key insect pest of cotton in Texas and Oklahoma, and an occasional pest in New Mexico, Arkansas, Louisiana, and other mid-South states of the United States of America. When heavy populations of the insect pest are left uncontrolled, the yield loss can become extremely high. Cotton fleahopper nymphs and adults feed on the juices of tender plant parts, especially the terminal buds and small squares. Deformed or ragged leaves are often seen as a result of this feeding. The greatest damage is to small squares that are no larger than a pinhead. The small squares turn brown or black and shed after being fed upon. Heavily infested plants grow tall and whip-like, have restricted growth of fruiting branches, and usually produce only a few bolls near the top. The insect and its damage is thus hard to detect until economic losses have been sustained.

Verde plant bug, a native species, emerged as an important boll-feeder along the Gulf Coast of the United States of America during the past ten to fifteen years. During this time, cotton yields have suffered losses from cotton boll rot in areas of South Texas. Piercing-sucking insects feeding on cotton bolls have been implicated in introducing the bacterial disease that causes boll rot. Verde plant bug was the dominant boll-feeding sucking bug species (>98% of insects collected using a beat bucket) from peak to late bloom in cotton fields near the coast along the Coastal Bend of South Texas, from Port Lavaca to the Lower Rio Grande Valley in 2010 and 2011. It was common in fields within 8 km of coastal waters (average of 0.42 bugs per plant during peak to late bloom), while it was not detected in inland fields. Cotton boll rot was found on up to 25% of the open bolls inspected, the disease was concentrated in coastal fields where verde plant bug was found, and it was the major contributor to boll damage. Results from field surveys and verde plant bug feeding on caged plants supported the positive association of verde plant bug presence and subsequent harvest-relevant cotton boll rot in open bolls at harvest (Armstrong, J., Brewer, M., Parker, R., and Adamzyk, J. (2013) *Verde Plant Bug (Hemiptera: Miridae) Feeding Injury to Cotton Bolls Characterized by Boll Age, Size, and Damage Ratings, J. Econ. Entomol.* 106(1): 189 Ð 195). Verde plant bug feeding on cotton bolls also results in lint and seed staining.

*Thrips* have "punch and suck" mouthparts that allow them to punch a hole in a leaf cell, insert their maxillary stylets, and suck up the cellular fluids. When *thrips* feed on terminal buds, on tiny developing leaves and on fruiting structures, the injury can be severe. When *thrips* feed on young undeveloped leaves within the terminal bud, the resulting damage is magnified as those leaves develop and expand. This is because the damaged tissue fails to develop properly, while undamaged tissue continues to grow. After prolonged feeding or feeding by high numbers of *thrips*, seedlings have a ragged appearance, with visible silvery feeding sites on cotyledons and terminal leaf tissue. Over time, these silver areas will turn brown in color. Heavily injured leaves usually have a crinkled, tattered appearance and often curl upwards at the margins. Seedlings with this type of injury are often described as "possum-eared cotton." Heavy *thrips* populations can stunt growth, cause death of the terminal bud (resulting in "crazy cotton"), delay fruiting, and reduce stand. Severe *thrips* injury can result in substantial cotton yield reductions. Both larvae and adults show a preference to feed on and in flowers, making them particularly difficult to control with chemical pesticides. In addition, *Frankliniella occidentalis* (Western flower *thrips*) is a very efficient vector of different plant topoviruses (e.g., tomato spotted wilt virus and Cotton leaf roll virus) that cause damage to cotton plants. In sum, *thrips* can severely impact early season stand and plant vigor and can be very costly to cotton farmer.

Chemical pesticides are the current insect control methods used against *Lygus hesperus* (Western tarnished plant bug), *Lygus lineolaris* (Tarnished plant bug), *Pseudatomoscelis seriatus* (Cotton fleahopper), *Creontiades signatus* Distant (Verde plant bug), and the *thysanopteran* pests *Frankliniella* spp and *Sericothrips variabilis* (*Thrips*). These chemical insecticide methodologies often require multiple applications and different types of chemical pesticides. For example, to control *lygus* as many as five to ten treatments per season may be required. To control *thrips*, two to three treatments per season may be required. At least one treatment is required to control cotton fleahopper.

The use of chemical pesticides to control insect pests increases the cost to the farmer growing cotton, particularly in regions experiencing high insect infestation, thus reducing any potential profit derived from cotton production. In addition, the use of different chemical pesticides with multiple applications can have a negative impact on the environment and beneficial insects. Further, the development of resistance to chemical pesticides has been observed in these cotton pests. For example, the western flower *thrips, Frankliniella occidentalis* Pergande, has shown resistance to a number of different chemical pesticides (Sten Jensen (2006) *Insecticide resistance in the western flower thrips, Frankliniella occidentalis*, Integrated Pest Management Reviews, 5: 131-146). Resistance to multiple classes of chemical pesticides (carbamate, organophosphate, and pyrethroid insecticides) used to control Tarnished plant bug (*Lygus lineolaris*) has also been observed (G L Snodgrass et al., (2009) *Acephate resistance in populations of the tarnished plant bug (Heteroptera: Miridae) from the Mississippi River Delta. J Econ Entomol,* 102(2): 699-707).

Because of the economic and environmental cost associated with the use of chemical pesticides to control insect pests of cotton, and the development of resistance to chemical pesticides, there is a need for a cotton plant that expresses an insecticidal toxin active against *Lygus hesperus* (Western tarnished plant bug), *Lygus lineolaris* (Tarnished plant bug), *Pseudatomoscelis seriatus* (Cotton fleahopper), *Creontiades signatus* (Distant) (Verde plant bug), and the *thysanopteran* pests *Frankliniella* spp and *Sericothrips variabilis* (*Thrips*).

SUMMARY OF THE INVENTION

In one aspect, the invention provides transgenic cotton plants comprising event MON 88702 exhibiting superior properties and performance compared to existing transgenic cotton plants and to new events constructed in parallel. The cotton event MON 88702 contains, at a single locus of insertion in the cotton genome, an expression cassette which confers the trait of resistance to *Hemipteran* and *Thysanopteran* insect pests.

In one embodiment, event MON 88702 is characterized by specific unique DNA segments that are useful in detecting the presence of the event in a sample. A sample is intended to refer to a composition that is either substantially pure cotton DNA or a composition that contains cotton DNA. In either case, the sample is a biological sample, i.e., it contains biological materials, including but not limited to DNA obtained or derived from, either directly or indirectly, the genome of cotton comprising event MON 88702. "Directly" refers to the ability of the skilled artisan to directly obtain DNA from the cotton genome by fracturing cotton cells (or by obtaining samples of cotton that contain fractured cotton cells) and exposing the genomic DNA for the purposes of detection. "Indirectly" refers to the ability of the skilled artisan to obtain the target or specific reference DNA, i.e. a novel and unique junction segment described herein as being diagnostic for the presence of the event MON 88702 in a particular sample, by means other than by direct via fracturing of cotton cells or obtaining a sample of cotton that contains fractured cotton cells. Such indirect means include, but are not limited to, amplification of a DNA segment that contains the DNA sequence targeted by a particular probe designed to bind with specificity to the target sequence, or amplification of a DNA segment that can be measured and characterized, i.e. measured by separation from other segments of DNA through some efficient matrix such as an agarose or acrylamide gel or the like, or characterized by direct sequence analysis of the amplicons, or cloning of the amplicon into a vector and direct sequencing of the inserted amplicon present within such vector. Alternatively, a segment of DNA corresponding to the position within the cotton chromosome at which the transgenic DNA was inserted into the cotton chromosome and which can be used to define the event MON 88702, can be cloned by various means and then identified and characterized for its presence in a particular sample or in a particular cotton genome. Such DNA segments are referred to as junction segments or sequences, and can be any length of inserted DNA and adjacent (flanking) cotton chromosome DNA so long as the point of joining between the inserted DNA and the cotton genome is included in the segment. In certain embodiments, SEQ ID NO:1, SEQ ID NO:2, SEQ ID NO:3, SEQ ID NO:4, SEQ ID NO:5, SEQ ID NO:6, and SEQ ID NO:10 and the reverse complement of each of these, are representative of such segments.

The specific sequences identified herein may be present uniquely in event MON 88702, or the construct comprised therein, and the identification of these sequences, whether by direct sequence analysis, by detecting probes bound to such sequences, or by observing the size and perhaps the composition of particular amplicons described herein, when present in a particular cotton germplasm or genome and/or present in a particular biological sample containing cotton DNA, are diagnostic for the presence of the event MON 88702, or the construct comprised therein, in such sample. It is known that the flanking genomic segments (i.e., the cotton genome segments of DNA sequence adjacent to the inserted transgenic DNA) are subject to slight variability and as such, the limitation of at least 99% or greater identity is with reference to such anomalies or polymorphisms from cotton genome to cotton genome. In one embodiment, nucleotide segments that are completely complementary across their length in comparison to the particular diagnostic sequences referenced herein are intended to be within the scope of the present invention.

The position of the nucleotide segments of the present invention relative to each other and within the cotton genome are illustrated in FIG. 1 and the nucleotide sequence of each is illustrated as set forth in SEQ ID NO:10. Nucleotide segments that characterize the event MON 88702 and which are diagnostic for the presence of event MON 88702, or the construct comprised therein, in a sample include SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, or SEQ ID NO:26. The presence of one, or two, or more of these nucleotide sequences in a sample, when such sample contains cotton tissue and thus cotton DNA, is diagnostic for the presence of the event MON 88702, or the construct comprised therein.

It is intended by use of the word "derived" that a particular DNA molecule is in the cotton plant genome, or is capable of being detected in cotton plant DNA. "Capable of being detected" refers to the ability of a particular DNA segment to be amplified and its size and or sequence characterized or elucidated by DNA sequence analysis, and can also refer to the ability of a probe to bind specifically to the particular DNA segment, i.e. the target DNA segment, and the subsequent ability to detect the binding of the probe to the target. In certain embodiments, the particular DNA segment or target DNA segment of the present invention is present within cotton that contains the insertion event MON 88702.

By reference to cotton it is intended that cotton cells, cotton seed, cotton plant parts and cotton plants are within the scope of the present invention so long as each embodiment contains a detectable amount of DNA corresponding to any one, two, or more of the segments that are described herein as being diagnostic for the presence of the cotton event MON 88702 DNA. In certain embodiments, cotton plant parts include cells; pollen; ovules; flowers; lint; seed; root tissue; stem tissue; and leaf tissue. Commodity products that are made from cotton in which a detectable amount of the segments of DNA described herein as being diagnostic for the presence of the event MON 88702 are within the scope of the invention. In some embodiments, such commodity products may include whole or process cotton seeds, cotton fiber, cotton oil and derivatives of cotton oil, cotton protein, cotton meal, animal feed comprising cotton, paper comprising cotton, cotton biomass, candle wicks, cotton string, cotton rope, cotton balls, cotton batting, cotton fuel products such as fuel derived from cotton oil or pellets derived from cotton gin waste, and cotton cellulose products such as rayon, plastics, photographic film, cellophane, fatty acids used for various industrial uses such as insulation materials, linoleum, oilcloth, waterproofing, and as a paint base.

In one embodiment, the DNA of cotton event MON 88702 may be present in each cell and in each genome on one chromosome of the cotton plant, cotton seed, and cotton tissues containing the event. As the cotton genome is transmitted to progeny in Mendelian fashion, if a cotton plant were homozygous for the event MON 88702 insertion, each progeny cotton plant and cell would contain the event DNA on each allele of the parental chromosome containing the event MON 88702 insertion and inherited by the progeny from the parent(s). However, if the cotton genome containing the event MON 88702 DNA is a heterozygous or hybrid parent, then about fifty percent of the pollen and about fifty percent of the ovules engaged in mating from hybrid parents will contain the cotton event MON 88702 DNA, resulting in a mixed population of progeny that contain the event MON 88702 DNA, and the percentage of such progeny arising from such crosses with hybrids can range anywhere from about fifty to about seventy five percent having the event MON 88702 DNA transmitted to such progeny.

In another embodiment, the DNA molecules of the present invention may be unique to the two separate junctions on either end of the inserted transgenic event MON 88702 DNA and the cotton genome DNA that is adjacent to, i.e. flanking, each end of the MON 88702 inserted DNA, or unique to the cotton event MON 88702 inserted DNA. DNA molecules having the sequence of these junction sequences, when present in a particular sample of cotton analyzed by the methods described herein using the probes, primers and in some cases using DNA sequence analysis, may be diagnostic for the presence of an amount of event MON 88702 cotton in that sample. Such DNA molecules unique to the cotton event MON 88702 DNA can be identified and characterized in a number of ways, including by use of probe nucleic acid molecules designed to bind specifically to the unique DNA molecules followed by detection of the binding of such probes to the unique DNA, and by thermal amplification methods that use at least two different DNA molecules that act as probes but the sequence of such molecules may be somewhat less specific than the probes described above. The skilled artisan understands that contacting a particular target DNA with a probe or primer under appropriate hybridization conditions will result in the binding of the probe or primer to the targeted DNA segment.

In one embodiment, the DNA molecules of the present invention may be target segments of DNA that may be capable of amplification and, when detected as one or more amplicons of the represented length obtained by amplification methods of a particular sample, may be diagnostic for the presence of event MON 88702, or the construct comprised therein, in such sample. In another embodiment, such DNA molecules or polynucleotide segments may have the nucleotide sequences as set forth in each of SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26, and are further defined herein and in the examples below. Primer molecules and/or probes may be provided in kit form along with the necessary reagents, including controls, and packaged together with instructions for use.

In one aspect, recombinant DNA molecules of the present invention are deemed to be within the scope of the present invention when present within or derived from a microorganism. In one embodiment, a microorganism is intended to include any microscopic cell, whether prokaryote or eukaryote or otherwise that contains DNA within a genome or chromosome or an extra-chromosomal DNA structure more commonly referred to as a plasmid or vector. In other embodiments, microscopic organisms include bacteria (prokaryotes) and cells corresponding to higher life forms (eukaryotes) which are beneath the visual range of the average human, typically beneath fifty cubic microns and more generally beneath ten cubic microns. Bacteria are common microscopic microorganisms that more likely than not could contain a vector or plasmid that contains one or more or all of the novel DNA segments of the present invention, including the expression cassette present as set forth in SEQ ID NO:27. In other aspects, plant cells and particularly cotton plant cells are within the scope of the invention when these contain any one, two, or more or all of the novel DNA segments of the present invention.

In another aspect, probes for use herein may comprise DNA molecules or polynucleotide segments of sufficient length to function under stringent hybridization conditions as defined herein to bind with a particular target DNA segment, i.e., a unique segment of DNA present within and diagnostic for the presence of, event MON 88702 DNA in a sample. Such a probe can be designed to bind only to a single junction or other novel sequence present only in the cotton event MON 88702 DNA, or to two or more such single junction segments. In one embodiment, the detection of the binding of such a probe to a DNA molecule in a particular sample suspected of containing cotton DNA is diagnostic for the presence of cotton event MON 88702 in the sample.

In yet another aspect, primers may comprise pairs of different oligonucleotides or polynucleotide segments for use in a thermal amplification reaction which amplifies a particular DNA target segment. Each primer in the pair is designed to bind to a rather specific segment of DNA within or near to a segment of DNA of interest for amplification. The primers bind in such way that these then act as localized regions of nucleic acid sequence polymerization resulting in the production of one or more amplicons (amplified target segments of DNA). In one embodiment of the present invention, use of primers designed to bind to unique segments of cotton event MON 88702 DNA in a particular biological sample and that amplify particular amplicons containing one or more of the junction segments described herein, and the detection and/or characterization of such amplicons upon completion or termination of the polymerase reaction, is diagnostic for the presence of the cotton event MON 88702 in the particular sample. The skilled artisan is well familiar with this amplification method and no recitation of the specifics of amplification is necessary here.

In a further aspect, the present invention provides cotton plants, cotton plant cells, cotton plant tissues and cotton seed resistant to infestation by *Hemipteran* and *Thysanopteran* insect pests, including but not limited to *Lygus hesperus, Lygus lineolaris, Pseudatomoscelis seriatus, Creontiades signatus, Frankliniella* spp, and *Sericothrips variabilis*. In a particular embodiment, the resistance to infestation by *Hemipteran* and *Thysanopteran* species arises in connection with the expression of a DNA segment, encoding an insecticidal protein, that is operably and covalently linked within the inserted transgenic DNA: a TIC834_16 protein (United States Patent Application, US20130269060, SEQ ID NO:34) expressed from the expression cassette within the inserted transgenic DNA as set forth in SEQ ID NO:10 and illustrated in FIG. 1b.

The TIC834_16 protein which provides resistance to *Hemipteran* and *Thysanopteran* insect pests in cotton event MON 88702 is expressed by a chimeric FMV/Hsp81.2 chimeric promoter (U.S. Pat. No. 8,940,962). FIG. 1b shows the relative position of each expression element (enhancer (E), promoter (P), 5' UTR (L), 3' UTR (T)) and the TIC834_16 coding sequence within the transgene cassette comprised within SEQ ID NO:10. Other constructs were evaluated and varied in the use expression elements. The transgene cassette used to create cotton event MON 88702 provided superior performance to other transgene cassettes when evaluated for resistance to *Hemipteran* and *Thysanopteran* insect pest infestation.

The event MON 88702 was selected based on comparisons to thousands of different independent transgenic events, each transformed with a construct comprising the transgene cassette presented as SEQ ID NO:27 or other constructs comprising the TIC834_16 coding sequence or related variant toxin proteins expressed using different expression elements. The events generated expressing TIC834_16 and variants related to TIC834_16 were compared to the non-transgenic control cotton variety DP393 for resistance to *Hemipteran* and *Thysanopteran* insect pests. The results as illustrated in the Examples below show that the event MON 88702 yields superior properties due to expression of the TIC834_16 protein. The plurality of transgenic events produced using the construct used for generating the event MON 88702 were each more likely than other events produced with other constructs to exhibit efficacious control of *Hemipteran* and *Thysanopteran* insect pests.

In one aspect, cotton plants and parts thereof including seed, each containing the DNA corresponding to event MON 88702, are within the scope of the present invention. In one embodiment, such plants and parts thereof including seed are resistant to *Hemipteran* and *Thysanopteran* infestation. In certain embodiments, such plants and seed include hybrids and inbreds, and plants and seed that contain only one event MON 88702 allele, i.e., a genome characterized as heterozygous with reference to the locus corresponding to the event MON 88702 DNA. Such hybrids may be produced by breeding plants comprising event MON 88702 with desirable germplasm as part of the commercial variety development process and other agriculturally desirable properties of cotton. Hybrids may be produced by any number of methods but a preferred method takes advantage of a first inbred (homozygous) parent that contains the event MON 88702 specific allele on both chromosomes at the locus at which the event MON 88702 DNA is inserted, and breeding the first inbred together with a second inbred which does not contain the MON 87702 DNA. Both parental inbred varieties will have one or more advantageous properties desirable in the progeny seed, i.e. the hybrid seed, and these hybrid seed are heterozygous for the event MON 88702 allele.

In one embodiment, a transgenic property or allele conferring some additional trait to a plant containing the event MON 88702 DNA may be desirable. In another embodiment, other such transgenic alleles conferring desirable traits may include herbicide tolerance: 19-51A (DD-04951A-7), BXN, MON 1445 (MON-01445-2), MON 88701 (MON-88701-3), MON 88913 (MON-88913-8), GHB614 (BCS-GH002-5), DAS-81910-7 (DAS-81910-7), GHB119 (BCS-GH005-8), LLCotton25 (ACS-GH0013), EE-GH1, EE-GH3, pDAB4468.18.07.1, and pDAB4468.19.10.3; insect resistance: 281-24-236 (DAS-24236-5), 3006-210-23 (DAS-21023-5), COT102 (SYN-IR102-7), COT67B (SYN-IR67B-1), Event-1, MON 531 (MON-00531-6), MON15985 (MON-15985-7), EE-GHS, EE-GH6, COT202, COT203, and A26-5; and insect resistance and herbicide tolerance: 31807, 31808, T303-3 (BCS-GH003-6) and T304-40 (BCS-GH004-7). A non-transgenic property (e.g., QTL or maturity group) may also confer a desirable trait and one with skill in the art would know how to breed cotton to contain such non-transgenic trait and event MON 88702 DNA. Certain varieties of cotton have properties that may be desirable to further reduce damage from insect pests and may be suitable as a parent line in breeding cotton that also comprises event MON 88702 DNA. Early maturing, short season varieties are more likely to escape attack and damage from late-season infestations of budworms, bollworms and lygus. Smooth leaf varieties tend to have reduced populations of aphid and whitefly populations while budworms and bollworms deposit fewer eggs when compared to hairy varieties. Okra leaf varieties with okra leaf trait allow improved canopy penetration of foliar insecticide treatments and the trait also has been associated with resistance to whiteflies. Nectariless varieties tend to have lower plant bug populations and reduced egg production capacity of most moth species because of reduced nectar availability. High glanding varieties with high glanding trait have additional gossypol glands which increases the resistant to budworms and bollworms.

The forgoing and other aspects of the invention will become more apparent from the following detailed description.

BRIEF DESCRIPTION OF THE DRAWINGS

FIG. 1a is a diagrammatic representation of the relative positions illustrated by each horizontal line, of the segments of the heterologous transgenic DNA, the flanking genomic DNA, the arbitrarily designated 5' and 3' genomic/inserted DNA junctions, and relative positions of sequence unique to event MON 88702 within the heterologous transgenomic DNA which may be used to identify cotton event MON 88702; the horizontal lines labeled [1], [2], [3], [4], [5], [6], [7], [8], [9], and [10] correspond to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, respectively; the horizontal bar labeled [10] (SEQ ID NO:10) represents the contig of the 5' genomic flanking DNA sequence ([7], SEQ ID NO:7), the inserted T-DNA cassette ([9], SEQ ID NO:9), and the 3' flanking DNA sequence ([8], SEQ ID NO:8); the small horizontal lines labeled [1] (SEQ ID NO:1), [2] (SEQ ID NO:2), [3] (SEQ ID NO 3), [4] (SEQ ID NO:4), [5] (SEQ ID NO:5), and [6] (SEQ ID NO:6) represent unique sequences of the genomic/insert DNA junctions that can be used to identify the presence of event MON 88702 in a biological sample; the thick arrows labeled [11] SQ21940 (SEQ ID NO:11), [12] SQ-50210 (SEQ ID NO:12), [17] SQ50844 (SEQ ID NO:17), [19] SQ50843 represent a subset of primers used in the event specific assay and the zygosity assay, and are positioned relative to where they hybridize to SEQ ID NO:10; the thick arrows labeled [13] PB10344 and [18] PB50279 are a subset of probes used in the event specific assay and the zygosity assay, and are positioned relative to where they hybridize to SEQ ID NO:10.

FIG. 1b is a diagrammatic representation of the T-DNA cassette in the plasmid vector used to transform event MON 88702, presented as SEQ ID NO:27 ([27]); the horizontal arrows below [27] represents the elements comprised within the T-DNA cassette (SEQ ID NO: 27); RB represents a T-DNA right border element, E represents an enhancer element, P represents a promoter element, L represents a 5' UTR, TIC834_6 represents the TIC834_6 coding sequence element, T represents a 3' UTR, and LB represents a T-DNA left border element; the horizontal lines labeled [22], [23], [24], [25], and [26] correspond to SEQ ID NO:22, SEQ ID NO:23, SEQ ID NO:24, SEQ ID NO:25, and SEQ ID NO:26, respectively and represent unique sequences of the junctions between elements or the coding sequence which can be used to identify the presence of event MON 88702 in a biological sample.

BRIEF DESCRIPTION OF THE SEQUENCES

SEQ ID NO:1 is a twenty nucleotide sequence representing the 5' junction regions of cotton genomic DNA and the integrated transgenic expression cassette. SEQ ID NO:1 is found within SEQ ID NO:10 at nucleotide position 1642-1661.

SEQ ID NO:2 is a twenty nucleotide sequence representing the 3' junction regions of cotton genomic DNA and the integrated transgenic expression cassette. SEQ ID NO:2 is found within SEQ ID NO:10 at nucleotide position 4785-4804.

SEQ ID NO:3 is a sixty nucleotide sequence representing the 5' junction regions of cotton genomic DNA and the integrated transgenic expression cassette. SEQ ID NO:3 is found within SEQ ID NO:10 at nucleotide position 1622-1681.

SEQ ID NO:4 is a sixty nucleotide sequence representing the 3' junction regions of cotton genomic DNA and the integrated transgenic expression cassette. SEQ ID NO:4 is found within SEQ ID NO:10 at nucleotide position 4765-4824.

SEQ ID NO:5 is a one hundred nucleotide sequence representing the 5' junction regions of cotton genomic DNA and the integrated transgenic expression cassette. SEQ ID NO:5 is found within SEQ ID NO:10 at nucleotide position 1602-1701.

SEQ ID NO:6 is a one hundred nucleotide sequence representing the 3' junction regions of cotton genomic DNA and the integrated transgenic expression cassette. SEQ ID NO:6 is found within SEQ ID NO:10 at nucleotide position 1602-1701.

SEQ ID NO:7 is a 1,651 nucleotide sequence representing the 5' flanking cotton genomic sequence up to the inserted T-DNA.

SEQ ID NO:8 is a 2,010 nucleotide sequence representing the 3' flanking cotton genomic sequence after the inserted T-DNA. The first four nucleotides of SEQ ID NO:8 are derived from an unknown origin and are not present in the non-transgenic DP393 variety which was used to transform cotton event MON 88702; and were likely introduced during the integration of the MON 88702 T-DNA.

SEQ ID NO:9 is a 3,143 nucleotide sequence corresponding to the transgenic inserted T-DNA of cotton event MON 88702.

SEQ ID NO:10 is a 6,804 nucleotide sequence corresponding to the contig nucleotide sequence of the 5' genomic flanking DNA nucleotide sequence, the inserted T-DNA nucleotide sequence in event MON 88702, and the 3' genomic flanking DNA nucleotide sequence; and includes SEQ ID NO:7 (nucleotides 1-1651), SEQ ID NO:9 (nucleotides 1652-4794), and SEQ ID NO:8 (nucleotides 4795-6804).

SEQ ID NO:11 is a 25 nucleotide sequence corresponding to a thermal amplification primer referred to as SQ21940 used to identify cotton event MON 88702 DNA in a sample, and is identical to the nucleotide sequence corresponding to positions 4720 to 4744 of SEQ ID NO:10.

SEQ ID NO:12 is a 24 nucleotide sequence corresponding to a thermal amplification primer referred to as SQ-50210 used to identify cotton event MON 88702 DNA in a sample, and is identical to the reverse compliment of the nucleotide sequence corresponding to positions 4803 to 4826 of SEQ ID NO:10.

SEQ ID NO:13 is a 22 nucleotide sequence corresponding to a probe referred to as PB10344 used to identify cotton event MON 88702 DNA in a sample, and is identical to the nucleotide sequence corresponding to positions 4745 to 4766 of SEQ ID NO:10.

SEQ ID NO:14 is a 23 nucleotide sequence corresponding to a thermal amplification primer referred to as SQ22496 used as an internal control in the event assay for MON 88702 and hybridizes to the *Gossypium hirsutum* fiber-specific acyl carrier protein (ACP1) gene (GenBank Accession U48777).

SEQ ID NO:15 is a 19 nucleotide sequence corresponding to a thermal amplification primer referred to as SQ22497 used as an internal control in the event assay for MON 88702 and hybridizes to the complimentary strand of the *Gossypium hirsutum* fiber-specific acyl carrier protein (ACP1) gene (GenBank Accession U48777).

SEQ ID NO:16 is a 20 nucleotide sequence corresponding to a probe referred to as PB13032 used as an internal control in the event assay for MON 88702 and hybridizes to the *Gossypium hirsutum* fiber-specific acyl carrier protein (ACP1) gene (GenBank Accession U48777).

SEQ ID NO:17 is a 24 nucleotide sequence corresponding to a thermal amplification primer referred to as SQ50844 used in the zygosity assay for event MON 88702 DNA in a sample, and is identical to the nucleotide sequence corresponding to positions 4672 to 4695 of SEQ ID NO:10.

SEQ ID NO:18 is a 20 nucleotide sequence corresponding to a probe referred to as PB50279 used to identify the cotton event MON 88702 allele in a sample for the zygosity assay, and is identical to the nucleotide sequence corresponding to positions 4735 to 4754 of SEQ ID NO:10.

SEQ ID NO:19 is a 26 nucleotide sequence corresponding to a thermal amplification primer referred to as SQ50843 used in the zygosity assay for event MON 88702 DNA in a sample which hybridizes to both the wild-type and MON 88702 alleles, and is identical to the reverse compliment of the nucleotide sequence corresponding to positions 4852 to 4877 of SEQ ID NO:10.

SEQ ID NO:20 is a 25 nucleotide sequence corresponding to a thermal amplification primer referred to as SQ50842 used in the zygosity assay for event MON 88702 DNA in a sample which hybridizes to only the wild-type DNA allele that does not contain the inserted MON 88702 transgene cassette in a region of wild-type DNA that was lost during transgene insertion and therefore does not correspond to a region along SEQ ID NO:10.

SEQ ID NO:21 is a 21 nucleotide sequence corresponding to a probe referred to as PB50278 used to identify the wild-type allele in the zygosity assay for event MON 88702 DNA in a sample, and hybridizes to only the wild-type DNA allele that does not contain the inserted MON 88702 transgene cassette in a region of wild-type DNA that was lost during transgene insertion and therefore does not correspond to a region along SEQ ID NO:10.

SEQ ID NO:22 is a 101 nucleotide sequence representing the junction between the right T-DNA border sequence and the FMV 35S enhancer sequence within the transgene cassette used to transform DP393 cotton to produce cotton event MON 88702 which includes 15 nucleotides of the right T-DNA border sequence, 53 nucleotides of intervening sequence, and 33 nucleotides of the enhancer sequence. SEQ ID NO:22 is positioned in SEQ ID NO:10 at nucleotide position 1705-1805.

SEQ ID NO:23 is a 77 nucleotide sequence representing the junction between the *Arabidopsis thaliana* HSP81.2 5' UTR and the TIC834_16 coding sequence within the transgene cassette used to transform DP393 cotton to produce cotton event MON 88702 which includes 19 nucleotides of the 5' UTR, 37 nucleotides of intervening sequence, and 21 nucleotides of the TIC834_16 coding sequence. SEQ ID NO:23 is positioned in SEQ ID NO:10 at nucleotide position 3244-3320.

SEQ ID NO:24 is a 97 nucleotide sequence representing the junction between the TIC834_16 coding sequence and the 3' UTR within the transgene cassette used to transform DP393 cotton to produce cotton event MON 88702 which includes 28 nucleotides of the TIC834_16 coding sequence, 32 nucleotides of intervening sequence, and 37 nucleotides of 3' UTR sequence. SEQ ID NO:24 is positioned in SEQ ID NO:10 at nucleotide position 4193-4289.

SEQ ID NO:25 is a 200 nucleotide sequence representing the junction between the 3' UTR and the left T-DNA border sequence within the transgene cassette used to transform DP393 cotton to produce cotton event MON 88702 which includes 29 nucleotides of the 3' UTR sequence, 138 nucleotides of intervening sequence, and 33 nucleotides of the left T-DNA border sequence. SEQ ID NO:25 is positioned in SEQ ID NO:10 at nucleotide position 4424-4623.

SEQ ID NO:26 is a 921 nucleotide sequence representing the TIC834_16 coding sequence within the transgene cassette used to transform DP393 cotton to produce cotton event MON 88702. SEQ ID NO:26 is positioned within SEQ ID NO:10 at nucleotide position 3300-4220.

SEQ ID NO:27 is a 3,598 nucleotide sequence representing the transgene cassette comprised within the binary plasmid transformation vector used to transform DP393 cotton to produce cotton event MON 88702. SEQ ID NO:9 the 3143 nucleotide sequence corresponding to the transgenic inserted DNA of cotton event MON 88702 is positioned in SEQ ID NO:27 at nucleotide position 254-3360.

DETAILED DESCRIPTION

The present invention provides a transgenic cotton plant that achieves insecticidal control over *Hemipteran* and *Thysanopteran* pests of cotton by expression of TIC834_16, i.e., MON 88702. Specifically, expression of the TIC834_16 insect inhibitory protein in cotton event MON 88702 provides resistance to the *Hemipteran* pests *Lygus hesperus* (Western tarnished plant bug), *Lygus lineolaris* (Tarnished plant bug), *Pseudatomoscelis seriatus* (Cotton fleahopper), *Creontiades signatus* Distant (Verde plant bug), and *Thysanoptera* such as *Frankliniella* spp and *Sericothrips variabilis* (Thrips). The event MON 88702 will meet a great need for control of these insects in the cotton market, as chemical insecticides often do not provide adequate control of these insects, or require multiple applications over the growing season, increasing the input of chemical pesticides in the environment and adding cost to the production of cotton.

Cotton event MON 88702 was produced by an *Agrobacterium*-mediated transformation process of cotton meristem tissue with a two T-DNA binary system. In this system, an *Agrobacterium* strain employing one binary plasmid vector with two T-DNA transgene cassettes was utilized. The first T-DNA transgene cassette was used for the selection of transformed cotton plant cells using a selectable marker which confers tolerance to the antibiotic spectinomycin. The second transgene cassette was the TIC834_16 expression cassette—presented as SEQ ID NO: 27 herein—which confers resistance to *Hemipteran* and *Thysanopteran* insect pests. The selection T-DNA cassette inserted randomly into the cotton genome at a site separate from the site of integration of the T-DNA containing the TIC834_16 expression cassette, thus allowing for segregation of the two T-DNA segments within the genome of the transformed cotton plants during the process of selfing or backcrossing, e.g. screening $R_1$ and higher generation transgenic plants.

The cotton cells transformed through this two T-DNA binary system were regenerated into intact cotton plants. Individual plants that showed integrity of the T-DNA cassette encoding the TIC834_16 protein, the absence (i.e., segregation) of the T-DNA selectable marker cassette, and the absence of plasmid backbone sequence were selected for further testing.

Specifically, over 200 transgenic events were produced using the transformation construct used to produce the transgenic cotton event MON 88702, and thirty eight additional constructs comprising TIC834_16 or related variants of TIC834_16 were generated and used to produce over two thousand one hundred eighty (2,180) other transgenic cotton events which were compared to the cotton event MON 88702 and similar cotton events. Many of these events were tested by ELISA assay for expression in the leaf tissue of the insecticidal protein, TIC834_16 or related variants. Many of these same events were examined for the presence of protein crystals which were the result of over-expression of the toxins and interfered with efficacy. A subset of the events produced from each transformation, and most of the constructs, were tested for efficacy for controlling *Hemipteran* insect pests in cage and field trials. It was determined that the plant expression elements in the construct used to produce cotton event MON 88702 provided the events with the best efficacy against the *Hemipteran* pests tested. Of the events created and tested, event MON 88702 was ultimately selected as the superior event in view of the beneficial and superior properties yielded thereby.

The plasmid DNA inserted into the genome of cotton event MON 88702 was characterized by detailed molecular analysis. This analysis included: the insert number (number of integration sites within the cotton genome), the genomic insert location (the specific site in the cotton genome where the insertion occurred), the copy number (the number of copies of the T-DNA within one locus), and the integrity of the transgenic inserted DNA. The detailed molecular analysis demonstrated that the plasmid construct containing the TIC834_16 expression cassette contains multiple segments (junction sequences between elements used to build or construct the expression cassette). These segments (e.g., sequences as set forth in SEQ ID NO:22, SEQ ID NO:23, SEQ ID NO:24, SEQ ID NO:25, and SEQ ID NO:26) are not known to appear naturally in the cotton genome or in other vectors or transgenic cotton events; they are unique to the event MON 88702. Further, cotton event MON 88702 is characterized as an insertion into a single locus in the cotton genome, resulting in two new loci or junction sequences (e.g., sequences as set forth in SEQ ID NO: 1, SEQ ID NO: 2, SEQ ID NO: 3, SEQ ID NO: 4, SEQ ID NO: 5, and SEQ ID NO: 6) between the inserted DNA and the cotton genome DNA that are not known to appear naturally in the cotton genome or in other transgenic cotton events; they are unique to the event MON 88702. These junction sequences are useful in detecting the presence of the event MON 88702 in cotton cells, cotton tissue, cotton seed, and cotton plants or cotton plant products, such as cotton commodity products. DNA molecular probes and primer pairs are described herein that have been developed for use in identifying the presence of these various junction segments in biological samples containing or suspected of containing cotton cells, cotton seed, cotton plant parts or cotton plant tissue that contain the event MON 88702.

The detailed molecular analysis also demonstrated that event MON 88702 contains a single T-DNA insertion with one copy of the TIC834_16 expression cassette. No additional elements from the transformation construct other than portions of the *Agrobacterium tumefaciens* right and left border regions used for transgenic DNA transfer from the plant transformation plasmid to the cotton genome were identified in event MON 88702. Finally, thermal amplification producing specific amplicons diagnostic for the presence of event MON 88702 in a sample and DNA sequence analyses were performed to determine the arbitrarily assigned 5' and 3' insert-to-plant genome junctions, confirm the organization of the elements within the insert, and determine the complete DNA sequence of the inserted transgenic DNA (SEQ ID NO:9) in cotton event MON 88702. SEQ ID NO:7 is a sequence representing the 5' DP393 cotton genomic DNA sequence flanking the inserted T-DNA sequence presented as SEQ ID NO:9. SEQ ID NO:8 is a sequence representing the 5' DP393 cotton genomic DNA sequence flanking the inserted T-DNA sequence presented as SEQ ID NO:9. SEQ ID NO:10 represents a contiguous sequence (contig) comprising the 5' DP393 flanking sequence, the inserted MON 88702 T-DNA and the 3' DP393 flanking sequence, and thus contains the insert-to-plant genome junction sequences.

Unless otherwise noted herein, terms are to be understood according to conventional usage by those of ordinary skill in the relevant art. Definitions of common terms in molecular biology may also be found in Rieger et al., Glossary of Genetics: Classical and Molecular, 5$^{th}$ edition, Springer-Verlag: New York, 1991; and Lewin, Genes V, Oxford University Press: New York, 1994. As used herein, the term "cotton" means species belong to the genus *Gossypium*, preferably *Gossypium hirsutum* L. and *Gossypium barbadense* L. and includes all plant varieties that can be bred with cotton plants containing event MON 88702, including wild cotton species as well as those plants belonging to the genus *Gossypium* that permit breeding between species.

The present invention provides for transgenic plants which have been transformed with a DNA construct that contains an expression cassette expressing toxic amounts of insecticidal protein TIC8334_16. What is meant by toxic amount is an efficacious amount, an insecticidal amount, an insecticidally effective amount, a target insect suppressive amount, an efficacious pesticidal amount, an amount in the diet of insects in the order of *Hemiptera* or *Thysanoptera* that is insecticidal, and other similar terms to be understood according to conventional usage by those of ordinary skill in the relevant art. Cotton plants transformed according to the methods and with the DNA constructs disclosed herein are resistant to *Hemipteran* and *Thysanopteran* insect pests.

A transgenic "plant" is produced by transformation of a plant cell with heterologous DNA, i.e., a polynucleic acid construct that includes a number of efficacious features of interest; regeneration of a plant resulting from the insertion of the transgene into the genome of the plant cell, and selection of a particular plant characterized by insertion into a particular genome location and the number of efficacious features of the regenerated transgenic plant. The term "event" refers to the unique molecular sequence resulting from inserting transgenic DNA into the gonome of a cotton plant at a specific location. This sequence is present in the original transformant, and comprises the inserted DNA, and flanking genomic sequence immediately adjacent to the inserted DNA. Such sequence is unique and would be expected to be transferred to a progeny that receives the inserted DNA including the transgene of interest as the result of a sexual cross of parental line that includes the inserted DNA (e.g., the original transformant and progeny resulting from selfing) and a parental line that does not contain the inserted DNA. The present invention also provides the original transformant plant and progeny of the transformant that include the heterologous DNA. Such progeny may be produced by a sexual outcross between plants comprising the event and another plant wherein the progeny includes the heterologous DNA. Even after repeated back-crossing to a recurrent parent, the event is present in the progeny of the cross at the same chromosomal location. The present invention is related to the transgenic event, cotton plants comprising MON 88702, progeny thereof, and DNA compositions contained therein.

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

A "probe" is an nucleic acid to which may be attached a conventional detectable label or reporter molecule, e.g., a radioactive isotope, ligand, chemiluminescent agent, or enzyme. Such a probe is complementary to a strand of a target nucleic acid, in the case of the present invention, to a strand of DNA from MON 88702 whether from a MON 88702 containing plant or from a sample that includes MON 88702 DNA. Probes according to the present invention include not only deoxyribonucleic or ribonucleic acids, but also polyamides and other probe materials that bind specifically to a target DNA sequence and can be used to detect the presence of that target DNA sequence.

DNA primers are polynucleic acids that are annealed to a complementary target DNA strand by nucleic acid hybridization to form a hybrid between the primer and the target DNA strand, then extended along the target DNA strand by a polymerase, e.g., a DNA polymerase. A DNA primer pair or a DNA primer set of the present invention refer to two DNA primers useful for amplification of a target nucleic acid sequence, e.g., by the polymerase chain reaction (PCR) or other conventional polynucleic acid amplification methods.

DNA probes and DNA primers are generally eleven (11) polynucleotides or more in length, often eighteen (18) polynucleotides or more, twenty-four (24) polynucleotides or more, or thirty (30) polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

Primers and probes based on the flanking genomic DNA and insert sequences disclosed herein can be used to confirm (and, if necessary, to correct) the disclosed DNA sequences by conventional methods, e.g., by re-cloning and sequencing such DNA molecules.

The nucleic acid probes and primers of the present invention hybridize under stringent conditions to a target DNA molecule. Any conventional nucleic acid hybridization or amplification method can be used to identify the presence of DNA from a transgenic plant in a sample. Polynucleic acid molecules also referred to as nucleic acid segments or fragments thereof are capable of specifically hybridizing to other nucleic acid molecules under certain circumstances. As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a polynucleic acid of the present invention will specifically hybridize to one or more of the nucleic acid molecules set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:22, SEQ ID NO:23, SEQ ID NO:24, SEQ ID NO:25, or SEQ ID NO:26, or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:22, SEQ ID NO:23, SEQ ID NO:24, SEQ ID NO:25, or SEQ ID NO:26, or complements or fragments of either under high stringency conditions. In one aspect of the present invention, a preferred marker nucleic acid molecule of the present invention has the nucleic acid sequence set forth in SEQ ID NO:1, or SEQ ID NO:2, or SEQ ID NO:3, or SEQ ID NO:4, or SEQ ID NO:5, or SEQ ID NO:6, or SEQ ID NO:7, or SEQ ID NO:8, or SEQ ID NO:9, or SEQ ID NO:10, or SEQ ID NO:22, or SEQ ID NO:23, or SEQ ID NO:24, or SEQ ID NO:25, or SEQ ID NO:26 or complements thereof or fragments of either. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of polynucleic acid amplification method directed to a target polynucleic acid molecule that is part of a polynucleic acid template. For example, to determine whether a cotton plant resulting from a sexual cross contains transgenic plant genomic DNA from a cotton plant comprising event MON 88702 of the present invention, DNA that is extracted from a cotton plant tissue sample may be subjected to a polynucleic acid amplification method using a primer pair that includes a first primer derived from a genomic DNA sequence in the region flanking the heterologous inserted DNA of event MON 88702 and is elongated by polymerase 5' to 3' in the direction of the inserted DNA. The second primer is derived from the heterologous inserted DNA molecule is elongated by the polymerase 5' to 3' in the direction of the flanking genomic DNA from which the first primer is derived. The amplicon may range in length from the combined length of the primer pair plus one nucleotide base pair, or plus about fifty nucleotide base pairs, or plus about two hundred-fifty nucleotide base pairs, or plus about four hundred-fifty nucleotide base pairs or more. Alternatively, a primer pair can be derived from genomic sequence on both sides of the inserted heterologous DNA so as to produce an amplicon that includes the entire insert polynucleotide sequence (e.g., a forward primer isolated from the genomic portion on the 5' end of SEQ ID NO:10 and a reverse primer isolated from the genomic portion on the 3' end of SEQ ID NO:10 that amplifies a DNA molecule comprising the inserted DNA sequence (SEQ ID NO:9) identified herein in the event MON 88702 genome). A member of a primer pair derived from the plant genomic sequence adjacent to the inserted transgenic DNA is located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

For practical purposes, one should design primers which produce amplicons of a limited size range, for example, between 20 to 1000 bases. Smaller (shorter polynucleotide length) sized amplicons in general are more reliably produced in thermal amplification reactions, allow for shorter cycle times, and can be easily separated and visualized on agarose gels or adapted for use in endpoint TAQMAN®-like assays. Smaller amplicons can be produced and detected by methods known in the art of DNA amplicon detection. In addition, amplicons produced using the primer pairs can be cloned into vectors, propagated, isolated, and sequenced or can be sequenced directly with methods well established in the art. Any primer pair derived from the combination of SEQ ID NO:7 and SEQ ID NO:9 or the combination of SEQ ID NO:8 and SEQ ID NO:9 that are useful in a DNA amplification method to produce an amplicon diagnostic for MON 88702 or progeny thereof is an aspect of the invention. Any single isolated DNA polynucleotide primer molecule comprising at least 15 contiguous nucleotides of SEQ ID NO:7, or its complement that is useful in a DNA amplification method to produce an amplicon diagnostic for MON 88702 or progeny thereof is an aspect of the invention. Any single isolated DNA polynucleotide primer molecule comprising at least 15 contiguous nucleotides of SEQ ID NO:8, or its complement that is useful in a DNA amplification method to produce an amplicon diagnostic for plants comprising MON 88702 or progeny thereof is an aspect of the invention. Any single isolated DNA polynucleotide primer molecule comprising at least 15 contiguous nucleotides of SEQ ID NO:9, or its complement that is useful in a DNA amplification method to produce an amplicon diagnostic for MON 88702 or progeny thereof is an aspect of the invention.

Polynucleic acid amplification can be accomplished by any of the various polynucleic acid amplification methods known in the art, including the polymerase chain reaction (PCR). Amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb (kilobase) of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking genomic DNA sequence from cotton event MON 88702 can be verified (and corrected if necessary) by amplifying such DNA molecules from cotton seed containing event MON 88702 DNA or cotton plants grown from the cotton seed containing event MON 88702 DNA deposited with the ATCC having accession No. PTA-122520, using primers derived from the sequences provided herein, followed by standard DNA sequencing of the PCR amplicon or cloned DNA fragments thereof.

The diagnostic amplicon produced by these methods may be detected by a plurality of techniques. One such method is Genetic Bit Analysis (Nikiforov, et al. Nucleic Acid Res. 22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled dideoxynucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (Innov. Pharma. Tech. 00:18-24, 2000). In this method, an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene/genomic sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermalstable polymerase and dNTPs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular Beacons have been described for use in sequence detection as described in Tyangi, et al. (Nature Biotech. 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermalstable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

DNA detection kits that are based on DNA amplification methods contain DNA primer molecules that hybridize specifically to a target DNA and amplify a diagnostic amplicon under the appropriate reaction conditions. The kit may provide an agarose gel based detection method or any number of methods of detecting the diagnostic amplicon that are known in the art. DNA detection kits can be developed using the compositions disclosed herein and are useful for identification of cotton event MON 88702 DNA in a sample and can be applied to methods for breeding cotton plants containing event MON 88702 DNA. A kit that contains DNA primers that are homologous or complementary to any portion of the cotton genomic region as set forth in SEQ ID NO:10 and to any portion of the inserted transgenic DNA as set forth in SEQ ID NO:10 is an object of the invention. The DNA molecules can be used in DNA amplification methods (PCR) or as probes in polynucleic acid hybridization methods, i.e., southern analysis, northern analysis.

Junction sequences may be represented by a sequence from the group consisting of SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, and SEQ ID NO:25. For example, the junction sequences may be arbitrarily represented by the nucleotide sequences provided as SEQ ID NO:1 and SEQ ID NO:2. Alternatively, the junction sequences may be arbitrarily represented by the nucleotide sequences provided as SEQ ID NO:3 and SEQ ID NO:4. Alternatively, the junction sequences may be arbitrarily represented by the nucleotide sequences provided as SEQ ID NO:5 and SEQ ID NO:6. These nucleotides are connected by phosphodiester linkage and in cotton event MON 88702 are present as part of the recombinant plant cell genome. The identification of one or more of SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, and SEQ ID NO:25 in a sample derived from a cotton plant, cotton seed, or cotton plant part is determinative that the DNA was obtained from cotton event MON 88702 and is diagnostic for the presence in a sample containing DNA from cotton event MON 88702. The invention thus provides a DNA molecule that contains at least one of the nucleotide sequences provided as SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26. Any segment of DNA derived from transgenic cotton event MON 88702 that is sufficient to include at least one of the sequences provided as SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26 is within the scope of the invention. In addition, any polynucleotide comprising a sequence complementary to any of the sequences described within this paragraph is within the scope of the invention.

The invention provides exemplary DNA molecules that can be used either as primers or probes for detecting the presence of DNA derived from a cotton plant comprising event MON 88702 DNA in a sample. Such primers or probes are specific for a target nucleic acid sequence and as such are useful for the identification of cotton event MON 88702 nucleic acid sequence by the methods of the invention described herein.

A "primer" is typically a highly purified, isolated polynucleotide that is designed for use in specific annealing or hybridization methods that involve thermal amplification. A pair of primers may be used with template DNA, such as a sample of cotton genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a replication of a piece or fragment of DNA that has been synthesized using amplification techniques. In some embodiments, an amplicon of the invention may comprise at least one of the sequences provided as SEQ ID NO:11, SEQ ID NO:12, SEQ ID NO:17, SEQ ID NO:19. In another embodiment, an amplicon may comprise at least one of the junction sequences of the present event, such as SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening nucleotide molecule) using as a template the target DNA strand. Primer pairs, as used in the invention, are intended to refer to use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. Exemplary DNA molecules useful as primers are provided as SEQ ID NO:11, SEQ ID NO:12, SEQ ID NO:17, SEQ ID NO:19. The primer pair provided as SEQ ID NO:11 and SEQ ID NO:12 are useful as a first DNA molecule and a second DNA molecule that is different from the first DNA molecule, and both are each of sufficient length of contiguous nucleotides of SEQ ID NO:10 to function as DNA primers that, when used together in a thermal amplification reaction with template DNA derived from cotton event MON 88702, to produce an amplicon diagnostic for cotton event MON 88702 DNA in a sample.

A "probe" is a nucleic acid that is complementary to a strand of a target nucleic acid. Probes according to the invention include not only deoxyribonucleic or ribonucleic acids but also polyamides and other probe materials that bind specifically to a target DNA sequence and the detection of such binding can be useful in diagnosing, discriminating, determining, or confirming the presence of that target DNA sequence in a particular sample. A probe may be attached to a conventional detectable label or reporter molecule, e.g., a radioactive isotope, ligand, chemiluminescent agent, or enzyme. Exemplary DNA molecules useful as a probes are provided as SEQ ID NO:13 and SEQ ID NO:18.

Probes and primers according to the invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from cotton event MON 88702 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: *Nucleic Acid Hybridization, A Practical Approach*, IRL Press, Washington, D.C. (1985).

Any number of methods well known to those skilled in the art can be used to isolate and manipulate a DNA molecule, or fragment thereof, disclosed in the invention, including thermal amplification methods. DNA molecules, or fragments thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying cotton event MON 88702, selecting plant varieties or hybrids comprising cotton event MON 88702, detecting the presence of DNA derived from the transgenic cotton event MON 88702 in a sample, and monitoring samples for the presence and/or absence of cotton event MON 88702 or plant parts derived from cotton plants comprising event MON 88702.

The invention provides cotton plants, cotton plant cells, cotton seeds, cotton plant parts (such as pollen, ovule, pod, flower tissue, root tissue, stem tissue, and leaf tissue), cotton progeny plants, cotton lint, and cotton commodity products. These cotton plants, cotton plant cells, cotton seeds, cotton plant parts, cotton progeny plants, cotton lint, and cotton commodity products contain a detectable amount of a polynucleotide of the invention, i.e., such as a polynucleotide having at least one of the sequences provided as SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, or SEQ ID NO:26. Cotton plants, plant cells, seeds, plant parts, and progeny plants of the invention may also contain one or more additional transgenes. Such additional transgene may be any nucleotide sequence encoding a protein or RNA molecule conferring a desirable trait including but not limited to increased insect resistance, increased water use efficiency, increased yield performance, increased drought resistance, increased seed quality, and/or increased herbicide tolerance, in which the desirable trait is measured with respect to a cotton plant lacking such additional transgene.

The invention provides cotton plants, cotton plant cells, cotton seeds, cotton plant parts (such as pollen, ovule, pod, flower tissue, root tissue, stem tissue, and leaf tissue), cotton progeny plants derived from a transgenic cotton plant containing event MON 88702 DNA. A representative sample of cotton seed containing event MON 88702 DNA has been deposited according to the Budapest Treaty with the American Type Culture Collection (ATCC®). The ATCC repository has assigned the Patent Deposit Designation PTA-122520 to the seed containing event MON 88702 DNA.

The invention provides a microorganism comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26 present in its genome. An example of such a microorganism is a transgenic plant cell. Microorganisms, such as a plant cell of the invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state.

The transgenic plant cell's new genetic composition and phenotype is a technical effect created by the integration of the heterologous DNA into the genome of the cell. Another aspect of the invention is a method of using a microorganism of the invention. Methods of using microorganisms of the invention, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event MON 88702 DNA, including the transgene inserted in cotton event MON 88702, to progeny. As used herein, "progeny" includes any plant, plant cell, seed, and/or regenerable plant part containing the event MON 88702 DNA derived from an ancestor plant and/or comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26. Plants, progeny, and seeds may be homozygous or heterozygous for the transgene of event MON 88702. Progeny may be grown from seeds produced by a cotton event MON 88702 containing plant and/or from seeds produced by a plant fertilized with pollen from a cotton event MON 88702 containing plant.

Progeny plants may be self-pollinated (also known as "selfing") to generate a true breeding line of plants, i.e., plants homozygous for the transgene. Selfing of appropriate progeny can produce plants that are homozygous for both added, exogenous genes.

Alternatively, progeny plants may be out-crossed, e.g., bred with another unrelated plant, to produce a varietal or a hybrid seed or plant. The other unrelated plant may be transgenic or non-transgenic. A varietal or hybrid seed or plant of the invention may thus be derived by sexually crossing a first parent that lacks the specific and unique DNA of the cotton event MON 88702 with a second parent comprising cotton event MON 88702, resulting in a hybrid comprising the specific and unique DNA of the cotton event MON 88702. Each parent can be a hybrid or an inbred/varietal, so long as the cross or breeding results in a plant or seed of the invention, i.e., a seed having at least one allele containing the DNA of cotton event MON 88702 and/or a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26. Two different transgenic plants may thus be crossed to produce hybrid offspring that contain two independently segregating, added, exogenous genes. For example, the MON 88702 containing TIC834_16 conferring insect resistance to cotton can be crossed with other transgenic cotton plants to produce a plant having the characteristics of both transgenic parents. One example of this would be a cross of MON 88702 containing TIC834_16 conferring *Hemipteran* and *Thysanopteran* insect resistance to cotton with a plant having one or more additional traits such as herbicide tolerance (e.g., cotton event MON 88913 (MON-88913-8) or cotton event LLCotton25 (ACS-GHØØ1-3)) and/or insect control (e.g., cotton event MON 15985 (MON-15985-7)), resulting in a progeny plant or seed that has resistance to *Hemipteran* and *Thysanopteran* insect pests and has at least one or more additional traits. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

The invention provides a plant part that is derived from cotton plants comprising event MON 88702. As used herein, a "plant part" refers to any part of a plant which is comprised of material derived from a cotton plant comprising event MON 88702. Plant parts include but are not limited to pollen, ovule, pod, flower, root or stem tissue, fibers, and leaves. Plant parts may be viable, nonviable, regenerable, and/or nonregenerable.

The invention provides a commodity product that is derived from cotton plants comprising event MON 88702 and that contains a detectable amount of a nucleic acid specific for event MON 88702. As used herein, a "commodity product" refers to any composition or product which is comprised of material derived from a cotton plant, whole or processed cotton seed, one or more plant cells and/or plant parts containing the cotton event MON 88702 DNA. Commodity products may be sold to consumers and may be viable or nonviable. Nonviable commodity products include but are not limited to nonviable seeds; whole or processed seeds, seed parts, and plant parts; cotton fiber, cotton lint, cotton oil and derivatives of cotton oil such as shortening, soaps, and cosmetics, cotton protein, cotton meal, animal feed comprising cotton, paper comprising cotton, cotton biomass, candle wicks, string and rope, cotton balls, cotton batting, cellulose products such as rayon, plastics, photographic film, cellophane, fatty acids used for various industrial uses such as insulation materials, linoleum, oilcloth, waterproofing, and as a paint base, and fuel products produced using cotton plants and cotton plant parts. Viable commodity products include but are not limited to seeds, plants, and plant cells. The cotton plants comprising event MON 88702 can thus be used to manufacture any commodity product typically acquired from cotton. Any such commodity product that is derived from cotton plants comprising event MON 88702 may contain at least a detectable amount of the specific and unique DNA corresponding to cotton event MON 88702, and specifically may contain a detectable amount of a polynucleotide comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26. Any standard method of detection for nucleotide molecules may be used, including methods of detection disclosed herein. A commodity product is within the scope of the invention if there is any detectable amount of a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26 in the commodity product.

The plants, progeny, seeds, plant cells, plant parts (such as pollen, ovule, pod, flower, root or stem tissue, and leaves), and commodity products of the invention are therefore useful for, among other things, growing plants for the purpose of producing seed and/or plant parts comprising cotton event MON 88702 for agricultural purposes, producing progeny comprising cotton event MON 88702 for plant breeding and research purposes, use with microbiological techniques for industrial and research applications, and sale to consumers.

Methods for producing an insect resistant cotton plant comprising the DNA sequences specific and unique to event MON 88702 of the invention are provided. Transgenic plants used in these methods may be homozygous or heterozygous for the transgene. Progeny plants produced by these methods may be varietal or hybrid plants; may be grown from seeds produced by a cotton event MON 88702 containing plant and/or from seeds produced by a plant fertilized with pollen from a cotton event MON 88702 containing plant; and may be homozygous or heterozygous for the transgene. Progeny plants may be subsequently self-pollinated to generate a true breeding line of plants, i.e., plants homozygous for the transgene, or alternatively may be out-crossed, e.g., bred with another unrelated plant, to produce a varietal or a hybrid seed or plant.

Methods of detecting the presence of DNA derived from a cotton cell, cotton tissue, cotton seed, or cotton plant comprising cotton event MON 88702 in a sample are provided. One method consists of (i) extracting a DNA sample from at least one cotton cell, cotton tissue, cotton seed, or cotton plant, (ii) contacting the DNA sample with at least one primer that is capable of producing DNA sequence specific to event MON 88702 DNA under conditions appropriate for DNA sequencing, (iii) performing a DNA sequencing reaction, and then (iv) confirming that the nucleotide sequence comprises a nucleotide sequence specific for event MON 88702, or the construct comprised therein, such as one selected from the group consisting of SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26. Another method consists of (i) extracting a DNA sample from at least one cotton cell, cotton tissue, cotton seed, or cotton plant, (ii) contacting the DNA sample with a primer pair that is capable of producing an amplicon from event MON 88702 DNA under conditions appropriate for DNA amplification, (iii) performing a DNA amplification reaction, and then (iv) detecting the amplicon molecule and/or confirming that the nucleotide sequence of the amplicon comprises a nucleotide sequence specific for event MON 88702, such as one selected from the group consisting of SEQ ID NO:1, SEQ ID NO:2, SEQ ID NO:3, SEQ ID NO:4, SEQ ID NO:5, and SEQ ID NO:6. The amplicon should be one that is specific for event MON 88702, such as an amplicon that comprises SEQ ID NO:1, or SEQ ID NO:2, or SEQ ID NO:3, or SEQ ID NO:4, or SEQ ID NO:5, or SEQ ID NO:6. The detection of a nucleotide sequence specific for event MON 88702 in the amplicon is determinative and/or diagnostic for the presence of the cotton event MON 88702 specific DNA in the sample. An example of a primer pair that is capable of producing an amplicon from event MON 88702 DNA under conditions appropriate for DNA amplification is provided as SEQ ID NO:11, and SEQ ID NO:12. Other primer pairs may be readily designed by one of skill in the art and would produce an amplicon comprising SEQ ID NO:1, or SEQ ID NO:2, or SEQ ID NO:3, or SEQ ID NO:4, or SEQ ID NO:5, or SEQ ID NO:6, wherein such a primer pair comprises at least one primer within the genomic region flanking the insert and a second primer within the insert. Another method of detecting the presence of DNA derived from a cotton cell, cotton tissue, cotton seed, or cotton plant comprising cotton event MON 88702 in a sample consists of (i) extracting a DNA sample from at least one cotton cell, cotton tissue, cotton seed, or cotton plant, (ii) contacting the DNA sample with a DNA probe specific for event MON 88702 DNA, (iii) allowing the probe and the DNA sample to hybridize under stringent hybridization conditions, and then (iv) detecting hybridization between the probe and the target DNA sample. An example of the sequence of a DNA probe that is specific for event MON 88702 DNA is provided as SEQ ID NO:13 or SEQ ID NO:18. Other probes may be readily designed by one of skill in the art and would comprise at least one fragment of genomic DNA flanking the insert and at least one fragment of insert DNA, such as sequences provided in, but not limited to, SEQ ID NO:1, SEQ ID NO:2, SEQ ID NO:3, SEQ ID NO:4, SEQ ID NO:5, SEQ ID NO:6, and SEQ ID NO:10. Detection of probe hybridization to the DNA sample is diagnostic for the presence of cotton event MON 88702 specific DNA in the sample. Absence of hybridization is alternatively diagnostic of the absence of cotton event MON 88702 specific DNA in the sample.

DNA detection kits are provided that are useful for the identification of cotton event MON 88702 DNA in a sample and can also be applied to methods for breeding cotton plants containing the appropriate event DNA. Such kits contain DNA primers and/or probes comprising fragments of SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26. One example of such a kit comprises at least one DNA molecule of sufficient length of contiguous nucleotides of SEQ ID NO:10 to function as a DNA probe useful for detecting the presence and/or absence of DNA derived from transgenic cotton plants comprising event MON 88702 in a sample. The DNA derived from transgenic cotton plants comprising event MON 88702 would comprise a DNA molecule having at least one sequence selected from SEQ ID NO:1, SEQ ID NO 2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26. A DNA molecule sufficient for use as a DNA probe is provided that is useful for determining, detecting, or diagnosing the presence and/or absence of cotton event MON 88702 DNA in a sample is provided as SEQ ID NO:13. Other probes may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides of SEQ ID NO:10 and be sufficiently unique to cotton event MON 88702 DNA in order to identify DNA derived from the event. Another type of kit comprises a primer pair useful for producing an amplicon useful for detecting the presence and/or absence of DNA derived from transgenic cotton event MON 88702 in a sample. Such a kit would employ a method comprising contacting a target DNA sample with a primer pair as described herein, then performing a nucleic acid amplification reaction sufficient to produce an amplicon comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26, and then detecting the presence and/or absence of the amplicon. Such a method may also include sequencing the amplicon or a fragment thereof, which would be determinative of, i.e. diagnostic for, the presence of the cotton event MON 88702 specific DNA in the target DNA sample. Other primer pairs may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of sequences provided in, but not limited to SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:22, SEQ ID NO:23, SEQ ID NO:24, SEQ ID NO:25, and SEQ ID NO:26 and be sufficiently unique to cotton event MON 88702 DNA in order to identify DNA derived from the event.

The kits and detection methods of the invention are useful for, among other things, identifying cotton event MON 88702, selecting plant varieties or hybrids comprising cotton event MON 88702, detecting the presence of DNA derived from the transgenic cotton plants comprising event MON 88702 in a sample, and monitoring samples for the presence and/or absence of cotton plants comprising event MON 88702 or plant parts derived from cotton plants comprising event MON 88702.

The sequence of the heterologous DNA insert, junction sequences, or flanking sequences from cotton event MON 88702 can be verified (and corrected if necessary) by amplifying such sequences from the event using primers derived from the sequences provided herein followed by standard DNA sequencing of the amplicon or of the cloned DNA.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

Deposit Information

A deposit of a representative sample of cotton seed containing event MON 88702 was made on Sep. 11, 2015 according to the Budapest Treaty with the American Type Culture Collection (ATCC) having an address at 10801 University Boulevard, Manassas, Va. USA, Zip Code 20110, and assigned ATCC Accession No. PTA-122520. Access to the deposits will be available during the pendency of the application to the Commissioner of Patents and Trademarks and persons determined by the Commissioner to be entitled thereto upon request. Upon issuance of the patent, all restrictions upon availability to the public will be irrevocably removed. The deposit has been accepted under the Budapest Treaty and will be maintained in the depository for a period of 30 years, or 5 years after the last request, or for the effective life of the patent, whichever is longer, and will be replaced as necessary during that period.

EXAMPLES

Example 1

Selection and Molecular Characterization of Cotton Event MON 88702

This example describes the transformation and selection of cotton event MON 88702. The expression of transgenes in plants is known to be influenced by chromosomal insertion position, perhaps due to chromatin structure (e.g., heterochromatin) or the proximity of transcriptional regulation elements (e.g., enhancers) close to the integration site (Kurt Weising et al., (1988) *Foreign genes in plants: transfer, structure, expression and applications. Annu. Rev. Genet.* 22: 421-77). For this reason, it is often necessary to screen a large number of transformation events in order to identify an event which demonstrates optimal expression of the introduced gene of interest. For example, it has been observed in plants and in other organisms that there may be wide variation in the levels of expression of an introduced gene among events. There may also be differences in spatial or temporal patters of expression, for example, differences in the relative expression of a transgene in various plant tissues, that may not correspond to the patterns expected from transcriptional regulatory elements present in the introduced gene construct.

For these reasons, the development of a transgenic cotton plant comprising a insecticidal protein that was active against *Hemipterans* and *Thysanopterans* without any negative effects on agronomics, yield or stacking viability required extensive analyses over several years of approximately two thousand four hundred (2,400) events derived from thirty nine (39) different plasmid vector constructs. The individual expression cassettes in the (39) thirty nine plasmid constructs varied with respect to the coding sequences for the insecticidal toxin protein by either utilizing the TIC834_16 coding sequence, the TIC807 (U.S. Pat. No. 8,609,936) coding sequence, or coding sequences of variant insecticidal toxin proteins closely related to TIC834_16, referred to as "engineered *Hemipteran* toxin proteins" and referenced as variants of TIC807 in United States Patent Application US20130269060. The individual expression cassettes in the thirty nine (39) plasmid constructs also varied with respect to the use of different transcriptional regulation elements and whether or not the insecticidal toxin protein was targeted to the chloroplast.

The transgene cassette presented as SEQ ID NO:27 is the construct used to produce cotton event MON 88702. Numerous rounds of testing and comparison of various plasmid vector constructs revealed that this transgenic cassette produced the events with the best efficacy against the two *Lygus* species *Lygus hesperus* (Western tarnished plant bug) and *Lygus lineolaris* (Tarnished plant bug), when compared to the events produced by other transgene cassettes from the thirty eight (38) other constructs.

The transgenic *Hemipteran* and *Thysanopteran* insect resistant cotton event MON 88702 was created through an *Agrobacterium*-mediated transformation of cotton meristem tissue (U.S. Pat. No. 8,044,260) with a two T-DNA system. In this system, an *Agrobacterium* strain employing one binary plasmid vector with two T-DNA transgene cassettes was utilized. The first T-DNA transgene cassette was used for the selection of transformed cotton plant cells using a selectable marker which confers tolerance to the antibiotic spectinomycin. The second T-DNA transgene cassette—which is presented as SEQ ID NO:27 and demonstrated in FIG. 1*b*—was inserted into the cotton genome to confer insecticidal resistance to *Hemipteran* and *Thysanopteran* insect pests.

The second T-DNA transgene cassette presented as SEQ ID NO:27 and shown in FIG. 1*b* is comprised of a right T-DNA border (RB), an enhancer (E) derived from the FMV 35S promoter, operably linked 5' to a promoter (P) derived from the *Arabidopsis thaliana* heat shock protein 81.2 forming a chimeric FMV/Hsp81.2 promoter (U.S. Pat. No. 8,940,962), which is operably linked 5' to a 5' UTR (L) derived from the *Arabidopsis thaliana* heat shock protein 81.2, which is operably linked 5' to the TIC834_16 coding sequence (United States Patent Application, US20130269060), which is operably linked 5' to a 3' UTR (T) derived from the 35S Cauliflower mosaic virus gene VI, followed by a left T-DNA border (LB). The first T-DNA transgene selection cassette inserted randomly into the cotton genome and at a site separate from the site of integration of the second T-DNA transgene cassette containing the TIC834_16 expression cassette, thus allowing for segregation of the two T-DNA segments within the genome of the transformed cotton plants during the process of selfing and/or backcrossing, e.g. screening $R_1$ and higher generation transgenic plants.

To produce MON 88702, cotton variety DP393 (Deltapine, St. Louis, Mo.) was transformed using the two T-DNA binary system described above. Transformed cotton cells were selected using spectinomycin and regenerated into intact cotton plants. Rooted plants with normal phenotypic characteristics were selected and transferred to soil for growth and further assessment. Initially, two hundred fifteen (215) events were created from the two T-DNA transformation system with a first T-DNA transgene selection cassette and a second T-DNA transgene cassette containing the TIC834_16 expression cassette of SEQ ID NO:27.

After preliminary molecular characterization, one hundred thirty three (133) events were identified as sufficient quality for further assessment and testing. The events were analyzed using a combination of analytical techniques such as TaqMan and/or PCR analysis to determine the presence of the second T-DNA transgene cassette containing the TIC834_16 expression cassette and the cassette copy number. From this analysis, thirty five (35) single-copy, $R_1$ events were selected and were grown in the growth chamber and assayed for efficacy against *Lygus lineolaris* (Tarnished plant bug). The assay was conducted in three (3) separate experiments due to the size limitation of the growth chambers.

The thirty five (35) events were further characterized in more detail both molecularly and phenotypically. Plants demonstrating efficacy were then allowed to self-pollinate and set seed for further characterization and analysis of the $R_2$ and subsequent generations. From the further efficacy screening, twenty four (24) events were selected for further analysis and characterization. Each event was analyzed by Southern blot to determine copy number of the transgene cassette containing the TIC834_16 expression cassette of SEQ ID NO:27, the insertion point within the cotton genome and the presence of backbone. If the presence of a backbone was detected, the event was further analyzed using DNA amplification techniques to determine if the backbone was linked to the transgene cassette containing the TIC834_16 expression cassette of SEQ ID NO:27 and if one kilobase of sequence flanking the left and right borders were in a native gene. From this analysis twelve (12) events remained.

Of the twelve (12) events, one event demonstrated insertion of the left border into a native gene (Event 12), four events demonstrated insertion of the right border into a native gene (Events 3, 7, 9, and 10), and five events were unable to be characterized for flanking sequence (Events 5, 6, 8, and 9). All twelve (12) events were used in subsequent efficacy testing in order to provide comparators for performance. Specifically, the twelve (12) events were tested and analyzed for insect resistance efficacy in growth chamber whole plant cage studies, cotton yield from transformed cotton plants, and protein expression.

Insect Resistance Efficacy

To assay for efficacy against *Lygus lineolaris* (Tarnished plant bug), five $R_1$ seeds were sown in 10 inch pots for each of the twelve (12) transgenic cotton events. An untransformed DP393 cotton variety was used as a negative control. Plants were maintained in an environment chamber with a photoperiod of sixteen (16) hours of light at thirty two (32) degrees Celsius and eight (8) hours of dark at twenty three (23) degrees Celsius, and a light intensity between eight hundred (800) and nine hundred (900) micro-Einsteins. At forty (40) to forty five (45) days after planting, the individual plants were enclosed in a cage made from breathable plastic "pollination" sheets (Vilutis and Company Inc, Frankfort, Ill.). The sheet sleeves were secured to the main stem just above the soil surface using a Velcro® tie. Two pairs of sexually mature male and female *Lygus lineolaris* adults (six days old) from a laboratory culture were collected into a fourteen milliliter round-bottom plastic tube (Bacton Dickson Labware, Franklin Lakes, N.J.) and used for each plant. The adults were released into each individual cage through a small slit on the cage side and then the cage was securely closed ensuring the insects would not escape. The insects were allowed to mate and the plants were kept in the cage for twenty one (21) days.

After twenty one (21) days, the plants were then cut below the cages and moved to a laboratory where the insects were collected for each plant and counted. Before opening the cage, the plants were vigorously shaken to ensure all of the insects fell off from their feeding sites to the base of the cage. Then the cage base was opened and all plant material removed and placed on a black sheet. The insects were collected using an aspirator. The plant was then thoroughly inspected to recover any remaining insects. The number of insects collected and their developmental stage were recorded for each plant. The insect counts were divided into several groups based upon maturity of the *Lygus*: nymphs up to $3^{rd}$ instar, $4^{th}$ instar, $5^{th}$ instar and adults. Table 1 shows the average number of *Lygus* for each of the twelve events wherein "SEM" is the standard error of the mean.

As demonstrated in Table 1, all of the events expressing TIC834_16 demonstrated resistance to *Lygus lineolaris*. Event 2/MON 88702 provided superior control of *Lygus* in this assay.

Cotton Yield from Transformed Cotton Plants

To assess yield, the twelve (12) events were grown in the field to full maturity. Four (4) rows of cotton plants were grown for each event. Cotton was harvested at two different time points during the growth cycle for each row. Events were assessed for the presence of the TIC834_16. If a row had plants lacking TIC834_16, the entire row was excluded from the yield assay. The yield for each event is provided in Table 2 and is expressed as pounds of seed cotton (lb S.C.). As demonstrated in Table 2, cotton event MON 88702 provided superior yield.

TABLE 2

Yield from cotton plants transformed with the transgene cassette containing the TIC834_16 expression cassette of SEQ ID NO: 27.

| Event | Number of Rows | Nursery yield (lb S.C.) | | |
|---|---|---|---|---|
| | | 1st harvest | 2nd harvest | Total |
| Event 1 | 4 | 24.5 | 0.0 | 24.5 |
| Event 2 MON 88702 | 3 | 18.1 | 9.0 | 27.1 |
| Event 3 | 1 | 8.5 | 0.0 | 8.5 |
| Event 4 | 4 | 19.5 | 6.5 | 26 |
| Event 5 | 4 | 26.6 | 0.0 | 26.6 |
| Event 6 | 4 | 22.8 | 6.4 | 29.2 |
| Event 7 | 4 | 19.7 | 13.3 | 27.8 |
| Event 8 | 3 | 18 | 6.0 | 24 |
| Event 9 | 4 | 15.4 | 5.7 | 21.1 |
| Event 10 | 4 | 20.4 | 9.1 | 29.5 |
| Event 11 | 4 | 24.4 | 4.8 | 29.2 |
| Event 12 | 4 | 29.8 | 0.0 | 29.8 |

Protein Expression

Protein expression was determined using plants derived from $R_2$ seed. Plants were grown in the greenhouse for each

TABLE 1

Average number of *Lygus lineolaris* (Tarnished plant bug) recovered from caged cotton plants transformed with the transgene cassette containing the TIC834_16 expression cassette of SEQ ID NO: 27.

| | Number of Plants | ≤3 | SEM | 4th | SEM | 5th | SEM | Adults | SEM | Total TPB/Plant | SEM |
|---|---|---|---|---|---|---|---|---|---|---|---|
| | | | | Nymphal Instars | | | | | | | |
| Event 1 | 5 | 4.20 | 2.62 | 3.00 | 1.52 | 2.20 | 1.02 | 0.00 | 0.00 | 9.40 | 4.82 |
| Event 2 MON 88702 | 5 | 1.00 | 0.77 | 0.00 | 0.00 | 0.80 | 0.37 | 0.20 | 0.20 | 2.00 | 1.30 |
| Event 3 | 5 | 6.60 | 4.60 | 2.80 | 1.07 | 1.40 | 0.51 | 0.00 | 0.00 | 10.80 | 5.15 |
| Event 4 | 5 | 6.60 | 4.89 | 3.20 | 1.59 | 0.00 | 0.00 | 0.40 | 0.24 | 10.20 | 5.40 |
| Event 5 | 5 | 2.00 | 2.00 | 0.00 | 0.00 | 0.00 | 0.00 | 0.00 | 0.00 | 2.00 | 2.00 |
| Event 6 | 5 | 3.00 | 0.95 | 2.40 | 0.60 | 1.60 | 0.51 | 0.00 | 0.00 | 7.00 | 1.58 |
| Event 7 | 5 | 0.00 | 0.00 | 0.40 | 0.24 | 0.00 | 0.00 | 0.00 | 0.00 | 0.40 | 0.24 |
| Event 8 | 5 | 1.00 | 0.77 | 0.00 | 0.00 | 0.00 | 0.00 | 0.00 | 0.00 | 1.00 | 0.77 |
| Event 9 | 5 | 3.80 | 2.65 | 2.00 | 1.05 | 2.20 | 0.66 | 0.40 | 0.24 | 8.40 | 4.12 |
| Event 10 | 5 | 1.60 | 1.12 | 0.60 | 0.60 | 0.60 | 0.60 | 0.00 | 0.00 | 2.80 | 1.71 |
| Event 11 | 5 | 1.80 | 1.36 | 2.00 | 1.30 | 2.00 | 1.14 | 0.20 | 0.20 | 6.00 | 3.82 |
| Event 12 | 5 | 0.40 | 0.40 | 0.60 | 0.40 | 1.60 | 1.36 | 1.40 | 0.87 | 4.00 | 2.79 |
| DP393 | 10 | 7.90 | 2.10 | 5.40 | 0.91 | 7.25 | 1.28 | 5.20 | 1.36 | 25.75 | 3.50 | of the twelve (12) events being assessed. Tissues were sampled at two different time points. Leaf and squares were harvested at forty five (45) days after planting (45L and 45S, respectively), and leaf was harvested at seventy (70) days after planting (70L). Protein expression was measured using ELISA on lyophilized tissue and was expressed as parts per million (ppm).

The average expression of each event is provided in Table 3. As demonstrated in Table 3, the expression of TIC834_16 varies with each event and within each tissue. The level of expression did not necessarily correlate with the plants' level of resistance to *lygus*.

TABLE 3

Average protein expression in selected tissues of $R_2$ cotton plants transformed with the transgene cassette containing the TIC834_16 expression cassette of SEQ ID NO: 27.

| Event | Protein Expression (dry weight ppm) | | |
|---|---|---|---|
|  | 45L | 45S | 70L |
| Event 1 | 918 | 746 | 872 |
| Event 2 MON 88702 | 965 | 994 | 765 |
| Event 3 | 1183 | 1096 | 789 |
| Event 4 | 1269 | 1088 | 958 |
| Event 5 | 900 | 689 | 748 |
| Event 6 | 798 | 958 | 631 |
| Event 7 | 1588 | 1574 | 1118 |
| Event 8 | 1748 | 1468 | 1142 |
| Event 9 | 688 | 1072 | 580 |
| Event 10 | 1074 | 1030 | 791 |
| Event 11 | 868 | 1195 | 938 |
| Event 12 | 976 | 769 | 748 |

After several years of extensive characterization, two events stood out from the rest as providing high resistance to *lygus*, beneficial phenotypic characteristics, and superior yield relative to untransformed DP393; Event 2 (MON 88702) and Event 10. The left and right flanking sequences of both events were used to BLAST against the proprietary assemblies of both the upland cotton TM1 (*Gossypium hirsutum*) tetraploid genome and the Cotton D (*Gossypium raimondii*) diploid genome to identify any potential issues with insertion into identified cotton genes, thus potentially disrupting a native gene.

Insertion of a transgenic cassette into a native gene can be problematic with respect to approval by regulatory agencies. Such observations can cause a product to not be approved or for extensive experimentation and characterization be performed to demonstrate the insertion within the native gene does not cause deleterious effects in the plant. Event 2/MON 88702 did not appear to be inserted within a gene based upon the upland cotton TM1 assembly and the Cotton D diploid genome. In contrast, while Event 10 did not appear to insert within a gene based upon the upland cotton TM1 assembly, based upon the Cotton D assembly it appeared the insertion of the transgenic cassette occurred within the second intron of an endogenous gene. Thus, Event 10 had a transgenic cassette insertion into an endogenous cotton gene.

Because Event 2/MON 88702 did not have an insertion issue, provided superior yield as compared to Event 10 in field studies, had preferred molecular characterization, and demonstrated excellent performance over several years in cage and field trails (as presented above and in the Examples below), it was identified as the superior event and thus the event selected for commercialization.

Example 2

Cotton Event MON 88702 Demonstrates Resistance to Artificial Infestations of *Lygus hesperus* (Western Tarnished Plant Bug) and *Lygus lineolaris* (Tarnished Plant Bug) in Open Field Cage Trials MON 88702 provides resistance to the *Lygus* species *Lygus hesperus* (Western tarnished plant bug) and *Lygus lineolaris* (Tarnished plant bug) as demonstrated in this Example. Open field caging experiments were conducted during consecutive growing seasons. Trials against *Lygus lineolaris* were conducted in Illinois in year 1 and repeated in Tennessee in year 2. Trials against *Lygus hesperus* were conducted in Arizona in year 1 and repeated in Arizona in year 2. Seeds from cotton event MON 88702 and the negative control DP393 treated with Acceleron® (which contains fungicides, the insecticide Imidacloprid, and the nematacide Thiodicarb) were sown in two (2) fifteen (15) foot row plots. At fifteen (15) to twenty (20) days after planting, plants were thinned to achieve uniform stand. At thirty five (35) to forty (40) days after planting, individual plants were carefully examined to remove any pests and predators present. Once all pests and predators were removed, the plants were enclosed in a cage (150×228 centimeters) made from white solid voile (JoAnne Fabrics, Item Number 8139875). The bottom voile sleeve was secured to the main plant stem just above the soil surface and the top sleeve was tied together using a Velcro® tie. Metal poles were placed at the end of each row and the top of each cage was attached to a string to keep the cages in an upright position.

*Lygus* nymphs were collected from alfalfa or canola fields and reared in the laboratory. On the day of eclosion, the adults were collected and moved to a new container to keep track of their developmental stage. At least one hundred (100) to one hundred fifty (150) adults at an approximately 1:1 sex ratio were placed in big plastic containers that provided uniform cohort for successful mating. On the day of infestation, all adults were at least six (6) days old with the cotton plants being forty five (45) to fifty (50) days after planting (i.e., the peak squaring stage). Two pairs of male and female adults were collected into fifteen milliliter plastic tubes and brought to the field.

Each cage was opened from the top and re-examined to remove any pests and predators which were overlooked in the previous inspection or which hatched after caging. The plants were then infested by releasing the *lygus* adults into the cage. Eight (8) plants were infested per treatment. Insects were allowed to reproduce and the resulting progeny allowed to feed on the caged cotton plant for thirty (30) days. Following this time period, the plants were harvested and the presence of *lygus* for each plant was collected and recorded as described in Example 1.

Table 4 and Table 5 show the average next generation insect counts for years 1 and 2 for *Lygus lineolaris* and *Lygus hesperus*, respectfully. The insect counts were divided into several groups based upon maturity of the *lygus*: small nymphs (defined as nymphs up to $3^{rd}$ instar), large nymphs (defined as being at the $4^{th}$ instar or the $5^{th}$ instar) and adults. Tables 4 and 5 show the average number of *lygus* for MON 88702 and the negative control DP393 for each trail, wherein "SEM" is the standard error of the mean.

TABLE 4

Average next generation insect counts for cotton event MON 88702 and the negative control DP393 infested with Lygus lineolaris.

| Year | Event | Number of Plants | Small Nymphs | Large Nymphs | Adults | Total Lygus | Total Lygus SEM |
|---|---|---|---|---|---|---|---|
| 1 | MON 88702 | 8 | 1.50 | 0.25 | 0.25 | 2.00 | 0.71 |
|   | DP393 | 8 | 12.00 | 2.50 | 0.38 | 14.88 | 1.95 |
| 2 | MON 88702 | 8 | 0.13 | 1.25 | 2.13 | 3.50 | 1.72 |
|   | DP393 | 16 | 4.19 | 4.13 | 3.38 | 11.69 | 2.06 |

TABLE 5

Average next generation insect counts for cotton event MON 88702 and the negative control DP393 infested with Lygus hesperus.

| Year | Event | Number of Plants | Small Nymphs | Large Nymphs | Adults | Total Lygus | Total Lygus SEM |
|---|---|---|---|---|---|---|---|
| 1 | MON 88702 | 8 | 0.00 | 0.50 | 1.75 | 2.25 | 1.32 |
|   | DP393 | 8 | 2.13 | 8.38 | 11.63 | 22.13 | 4.96 |
| 2 | MON 88702 | 8 | 0.88 | 1.38 | 2.75 | 5.00 | 1.88 |
|   | DP393 | 16 | 3.19 | 8.69 | 7.94 | 19.81 | 2.86 |

As demonstrated in Tables 4 and 5, cotton transgenic event MON 88702 provides protection against both *Lygus lineolaris* and *Lygus hesperus*. The average insect counts for small nymphs, large nymphs and adults were much lower in the MON 88702 caged plants than the control DP393 plants.

Example 3

Cotton Event MON 88702 Provides Resistance to *Lygus lineolaris* and *Lygus hesperus* in the Field Under Natural *Lygus* Pressure This Example demonstrates the ability of transgenic cotton event MON 88702 to provide resistance to the Hemipteran pest species *Lygus hesperus* (Western tarnished plant bug) and *Lygus lineolaris* (Tarnished plant bug).

Field trials were conducted over 3 years: year 1, year 2 and year 3 in various locations which experienced different levels of natural *Lygus* pressure as defined by an economic threshold determined through two (2) methods of survey. For fields in the Delta region of the United States (Arkansas (AR), Louisiana (LA), Mississippi (MS), and Tennessee (TN)), the drop cloth method was used to survey for the predominant *Lygus* species, *Lygus lineolaris* (Tarnished plant bug). The drop cloth method essentially consists of placing a drop cloth between two rows of cotton and vigorously shaking the plants from both rows over the drop cloth. The insects are separated by stage and counted. For fields in the Southwest region of the United States (Arizona (AZ) and California (CA)), the sweep net method was employed and used to survey the predominant *Lygus* species, *Lygus hesperus* (Western tarnished plant bug). The sweep net survey method essentially consists of sweeping a net through the top of the canopy for a specified number of sweeps and then counting the number of insects after separating for stages.

Eight (8) row plots of cotton were grown using 120 seeds treated with Acceleron® (which contained fungicides, the insecticide Imidacloprid, and the nematacide Thiodicarb) per thirty (30) foot long row for each event tested. Each plot was replicated four (4) times in the field. The untransformed cotton variety DP393 was used as a negative control and planted in four (4) replicates of eight (8) row plots just as the transgenic events. The *Lygus* nymphs sampled were divided into two groups, small nymphs (defined as nymphs up to $3^{rd}$ instar) and large nymphs (defined as being at the $4^{th}$ instar or the $5^{th}$ instar). The number of nymphs detected was expressed as the number of nymphs per five (5) feet of row (5 row feet).

Table 6 shows the number of nymphs detected per 5 row feet for transgenic cotton event MON 88702 and the negative control DP393, wherein "SEM" is the standard error of the mean and "N" is the number of plants caged and sampled. The *Lygus* pressure shown in Table 6 is determined relative to the economic threshold for applying insecticide on the cotton field. The economic threshold for applying insecticide on cotton for *Lygus* control is defined differently depending on the type of survey method used. The conventional economic threshold using the drop cloth method for *Lygus lineolaris* is three (3) total *Lygus* (any stage) per 5 row feet. The economic threshold for spraying insecticide on cotton for *Lygus hesperus* control using the sweep method is fifteen (15) total *Lygus* (including 4-8 nymphs) per one hundred sweeps. Because of natural variation in *Lygus* pressure in our trials, locations were categorized as low, medium, or high pressure sites. Low *Lygus* pressure is defined as being below the economic threshold throughout the season. Medium *Lygus* pressure is defined as being equal or greater than one times the economic threshold, or less than three times the economic threshold at any time in the season. High *Lygus* pressure is defined as being equal or greater than three times the economic threshold, at any time in the season.

For transgenic trait efficacy evaluation, total nymphs numbers as adults caught during sampling cannot be assumed to have developed on that particular plot. As can be seen in Table 6, the total number of nymphs detected in the transgenic event MON 88702 rows was consistently less than the total number of nymphs in the untransformed control rows. This observation was consistent regardless of the natural *Lygus* pressure in each field throughout the three (3) years. This demonstrates that transgenic cotton event MON 88702 provides superior resistance to both *Lygus lineolaris* and *Lygus hesperus* in cotton field experiments relative to the untransformed cotton.

TABLE 6

Season long average numbers of Lygus nymphs per 5 row feet for MON 88702 and DP393 in the field.

| Year | Location | Lygus species | Natural Lygus Pressure Rating | Event | N | Small Nymphs | Large Nymphs | Total Nymphs | Total Nymphs SEM |
|---|---|---|---|---|---|---|---|---|---|
| Year 1 | MS | Lygus lineolaris | High | MON 88702 | 20 | 6.40 | 0.40 | 6.80 | 1.44 |
|   |   |   |   | DP393 | 40 | 14.80 | 1.89 | 16.69 | 2.24 |
|   | AR | Lygus lineolaris | High | MON 88702 | 24 | 8.10 | 2.85 | 10.96 | 3.20 |
|   |   |   |   | DP393 | 48 | 10.21 | 2.68 | 12.89 | 1.71 |
|   | LA | Lygus lineolaris | Low | MON 88702 | 4 | 0.23 | 0.08 | 0.31 | 0.11 |
|   |   |   |   | DP393 | 8 | 0.20 | 0.14 | 0.33 | 0.06 |

TABLE 6-continued

Season long average numbers of *Lygus* nymphs per 5 row feet for MON 88702 and DP393 in the field.

| Year | Loca-tion | *Lygus* species | Natural *Lygus* Pressure Rating | Event | N | Small Nymphs | Large Nymphs | Total Nymphs | Total Nymphs SEM |
|---|---|---|---|---|---|---|---|---|---|
| Year 2 | MS | *Lygus lineolaris* | High | MON 88702 | 20 | 5.80 | 0.38 | 6.18 | 1.61 |
| | | | | DP393 | 40 | 10.83 | 1.36 | 12.19 | 1.49 |
| | AR | *Lygus lineolaris* | Medium | MON 88702 | 24 | 3.88 | 0.54 | 4.42 | 0.51 |
| | | | | DP393 | 48 | 4.46 | 0.85 | 5.31 | 0.46 |
| | LA | *Lygus lineolaris* | Low | MON 88702 | 28 | 1.64 | 1.05 | 2.70 | 0.63 |
| | | | | DP393 | 56 | 3.90 | 1.89 | 5.79 | 0.98 |
| | AZ | *Lygus hesperus* | Low | MON 88702 | 36 | 2.78 | 1.39 | 4.17 | 0.99 |
| | | | | DP393 | 72 | 2.01 | 2.92 | 4.93 | 0.67 |
| | CA | *Lygus hesperus* | Medium | MON 88702 | 24 | 1.88 | 5.21 | 7.08 | 2.87 |
| | | | | DP393 | 48 | 3.33 | 11.67 | 15.00 | 3.80 |
| Year 3 | MS | *Lygus lineolaris* | High | MON 88702 | 16 | 6.47 | 1.47 | 7.94 | 1.51 |
| | | | | DP393 | 16 | 11.31 | 6.28 | 17.59 | 1.25 |
| | AR | *Lygus lineolaris* | Medium | MON 88702 | 16 | 2.22 | 0.31 | 2.53 | 0.43 |
| | | | | DP393 | 16 | 3.31 | 0.31 | 3.63 | 0.74 |
| | LA | *Lygus lineolaris* | Medium | MON 88702 | 28 | 1.54 | 1.02 | 2.55 | 0.48 |
| | | | | DP393 | 28 | 2.07 | 1.82 | 3.89 | 0.71 |
| | AR | *Lygus lineolaris* | Low | MON 88702 | 16 | 0.33 | 0.18 | 0.50 | 0.18 |
| | | | | DP393 | 16 | 0.70 | 0.53 | 1.23 | 0.17 |

Example 4

Cotton Event MON 88702 Provides Superior Yield in the Field Under Low, Medium, and High Natural *Lygus* Pressure This Example demonstrates the ability for transgenic cotton event MON 88702 to provide superior yield in fields infested with the *Hemipteran* pest species *Lygus hesperus* (Western tarnished plant bug) and *Lygus lineolaris* (Tarnished plant bug) relative to untransformed cotton plants.

Field trials were conducted in three consecutive years in various locations which experienced different levels of natural *Lygus* pressure as described in Example 3. The two center rows of each eight row plot were harvested and the yield was measured and expressed in pounds of seed cotton per acre (lbs/acre).

Table 7 demonstrates the yield of seed cotton per acre for each of the field locations and is divided based upon the natural *Lygus* pressure experienced in each field. The column percent change vs. control shows the increased percentage of yield on the MON 88702 event relative to the untransformed DP393 negative control.

TABLE 7

Seed cotton yield for event MON 88702 and untransformed DP393 in fields under varying *Lygus* pressure.

| Natural *Lygus* Pressure Rating | Year | Loca-tion | *Lygus* species | MON 88702 (lbs/acre) | DP393 (lbs/acre) | Percent change vs. control |
|---|---|---|---|---|---|---|
| High | 3 | MS | *Lygus lineolaris* | 2646 | 1728 | 53% |
| | 2 | MS | *Lygus lineolaris* | 2101 | 816 | 157% |
| | 1 | MS | *Lygus lineolaris* | 2248 | 1377 | 63% |
| | | AR | *Lygus lineolaris* | 2206 | 1303 | 69% |
| Medium | 3 | LA | *Lygus lineolaris* | 3173 | 2384 | 33% |
| | | ,AR | *Lygus lineolaris* | 2075 | 1238 | 68% |
| | 2 | AR | *Lygus lineolaris* | 2787 | 1911 | 46% |
| | | CA | *Lygus hesperus* | 3886 | 2696 | 44% |
| Low | 3 | AR | *Lygus lineolaris* | 3109 | 2872 | 8% |
| | 2 | LA | *Lygus lineolaris* | 2509 | 2256 | 11% |
| | | AZ | *Lygus hesperus* | 3490 | 3128 | 12% |
| | 1 | LA | *Lygus lineolaris* | 2140 | 2257 | −5% |

As demonstrated in Table 7, cotton transgenic event MON 88702 consistently provided higher yields of cotton under different degrees of natural *Lygus* pressure with the exception of the low pressure year 1 LA trial. The following year, a yield enhancement of 11% was observed for this same location under low *Lygus* pressure. The yield enhancement seen with event MON 88702 was greater in fields experiencing medium and high *Lygus* pressure. Under medium *Lygus* pressure, event MON 88702 provided yield increases of thirty-three (33) to sixty-eight (68) percent, depending on the location grown. Under high *Lygus* pressure, event MON 88702 provided yield increases of fifty-three (53) to one hundred seven (157) percent, depending on the location grown.

Example 5

Cotton Event MON 88702 Provides Superior Yield in the Field Under Medium and High Natural *Lygus* Pressure with or without Insecticide Applications This Example illustrates the superior yield of transgenic cotton event MON 88702 under medium and high *Lygus* pressure with or without application of insecticides when compared to untransformed cotton of the same variety.

Cotton yield in insecticide spray assays was assessed at six locations in a single planting season. Eight (8) row plots of cotton were grown using one hundred twenty (120) seeds treated with Acceleron® (which contained fungicides, the insecticide Imidacloprid, and the nematacide Thiodicarb) per each thirty (30) foot long row for event MON 88702. The untransformed cotton variety DP393 was planted and used as a negative control. Each plot was replicated three (3) times in the field. Three (3) treatment blocks were designed to evaluate the yield of cotton under conditions when the plots were not treated with insecticide to control *Lygus* or were treated with insecticide to control *Lygus*. The treatment block where no insecticide to control *Lygus* was applied during the season is referred to as the "no spray block." Two treatment blocks in which insecticide to control *Lygus* was applied are referred to as "spray by entry" and "spray by block." For spray by entry, the individual entry containing MON 88702 or untransformed DP393 is sprayed with insecticide when the average of the three (3) reps of that particular entry is at conventional economic threshold for *Lygus lineolaris* or fifteen (15) *Lygus* per one hundred (100) sweeps for *Lygus hesperus*. For spray by block, the entire block which contains both event MON 88702 and untransformed DP393 is sprayed with insecticide when the average of the three (3) reps of the DP393 in that block is at economic threshold for *Lygus lineolaris* or fifteen (15) *Lygus* per one hundred sweeps for *Lygus hesperus*. Table 8 shows the yield expressed in lbs/acre for the three (3) blocks at each location tested, along with the natural *Lygus* pressure experienced at each location.

As demonstrated in Table 8, insecticide-untreated and insecticide-treated event MON 88702 provided greater yield relative to the corresponding untransformed control DP393. Without insecticide treatment, the percent increase in yield ranged from 21% to 188%, depending on the location. With spray by entry, the percent increase in yield ranged from 5% to 72%, depending on location. With spray by block, the percent increase in yield ranged from 8% to 47%, depending on location. In all locations, whether or not treated with insecticide, transgenic cotton event MON 88702 provided increased yield relative to the untransformed control.

scale of 0-5. A damage rating score of zero (0) equaled no damage and no *thrips* observed. A damage rating of one (1) corresponded to an indication of *thrips* being present. A damage rating of two (2) corresponded to minor injury to the terminal bud and leaves. A damage rating of three (3) corresponded to a moderate injury to the terminal bud and leaves. A damage rating of four (4) corresponded to severe injury to the terminal bud and leaves with some dead plants and aborted terminal buds. A damage rating of five (5) corresponded to plant death, severe stunting, stacked internodes, reduced leaf area and terminal bud abortion of most plants. Because of natural variation in *thrips* pressure in the trials, locations were categorized as low, medium, or high pressure sites. Low, medium, and high natural *thrips* pressure is defined by the highest damage rating score recorded for the untransformed variety at any rating time at that particular location. Low *thrips* pressure corresponds to a damage rating below two (2). Medium *thrips* pressure corresponds to a damage rating of equal to or great than two (2) and less than four (4). High *thrips* pressure corresponds to a damage rating of equal to or greater than four (4). Table 9 demonstrates the average *thrips* damage ratings for three locations grown in a single planting season.

TABLE 8

Seed cotton yield (lbs/acre) for event MON 88702 and untransformed DP393 untreated or treated with insecticides.

| | | No spray block | | | Spray by entry | | | Spray by block | | |
| --- | --- | --- | --- | --- | --- | --- | --- | --- | --- | --- |
| Location | *Lygus* species | Natural *Lygus* Pressure Rating | MON 88702 | DP393 | Percent change vs. DP393 | MON 88702 (# sprays) | DP393 Yield (# sprays) | Percent change vs. DP393 | MON 88702 (# sprays) | DP393 Yield (# sprays) | Percent change vs. DP393 |
| MS | *Lygus lineolaris* | High | 2993 | 1558 | 92% | 2848 (3) | 2435 (4) | 17% | 2986 (4) | 2341 (4) | 28% |
| TN | *Lygus lineolaris* | High | 2049 | 1447 | 42% | 2758 (4) | 2636 (5) | 5% | 2844 (4) | 2622 (4) | 8% |
| NC | *Lygus lineolaris* | High | 2693 | 1047 | 157% | 3888 (2) | 2259 (2) | 72% | 4460 (3) | 3252 (3) | 37% |
| AZ | *Lygus hesperus* | High | 4987 | 4065 | 23% | 5387 (1) | 4530 (1) | 18% | 5017 (1) | 4566 (1) | 9% |
| AR | *Lygus lineolaris* | Medium | 2430 | 843 | 188% | 2465 (2) | 1955 (2) | 26% | 3330 (2) | 2258 (2) | 47% |
| LA | *Lygus lineolaris* | Medium | 1402 | 1155 | 21% | 1997 (2) | 1613 (3) | 23% | 2273 (3) | 1816 (3) | 25% |

Example 6

Cotton Event MON 88702 Provides Resistance in the Field Under Medium and High Natural *Thrips* Pressure This Example illustrates the ability of transgenic cotton event MON 88702 to provide excellent resistance to *thrips* under medium and high natural *thrips* pressure when compared to untransformed cotton plants in the field during a single planting season at multiple field locations.

Eight (8) row plots of cotton were grown using one hundred twenty (120) seeds for event MON 88702 or the untransformed cotton variety DP393 per thirty (30) foot long row (four seeds per row foot) treated with Acceleron® (which contains fungicides, the insecticide Imidacloprid, and the nematacide Thiodicarb). Each plot was replicated four (4) times in the field.

Damage to the cotton plants caused by *thrips* was assessed during the 2-4 true leaf stage using a damage rating

TABLE 9

Average thrips damage ratings for MON 88702 and the negative control DP393 in 2014.

| Natural Thrips Pressure | Location | MON 88702 | DP393 |
| --- | --- | --- | --- |
| High | MS | 1.3 | 4 |
| Medium | TN | 0.9 | 3 |
| Medium | VA | 0.3 | 2.7 |

As demonstrated in Table 9, cotton event MON 88702 provides resistance against *thrips* (*Frankliniella* spp). The cotton transgenic event MON 88702 consistently had significantly lower damage rating scores relative to the negative control DP393, regardless of the natural *thrips* pressure.

Example 7

Cotton Event MON 88702 Provides *Thrips* Resistance in the Field with or without Insecticide Application, and with or without Seed Treatment This Example illustrates the ability of transgenic cotton event MON 88702 to provide superior *thrips* resistance to multiple *thrips* species, including *Frankliniella fusca* (Tobacco thrips), *Frankliniella tritici* (Flower thrips), *Frankliniella occidentalis* (Western flower thirps), and *Sericothrips variabilis* (soybean *thrips*), with or without insecticide application and with or without seed treatment when compared to the untransformed DP393 control in fields during a single growing season.

Four (4) row plots of cotton were grown using one hundred twenty (120) seeds of cotton transgenic event MON 88702 or the untransformed DP393 per thirty (30) foot long row (four seeds per row foot). Seeds were either treated with Acceleron® (which contains fungicides, the insecticide Imidacloprid, and the nematacide Thiodicarb), or only fungicides. In addition, the plots were either sprayed or not sprayed with insecticide. The experimental design is shown in Table 10. For those plots in which an insecticide was sprayed, a prophylactic foliar application of Orthene (acephate) was applied at the one (1) to two (2) true leaf stage. Damage to the cotton plants caused by *thrips* was assessed at two different time points (first at the one to two true leaf stage and second at the three to four true leaf stage) using a damage rating scale of 0-5 as described previously in Example 6. Two damage ratings were performed at each location, with the exception of the TN trials in which four damage ratings were performed for trial 1 and three damages ratings were performed for trial 2.

TABLE 10

Experimental design of thrips resistance field trial.

| Event | Seed Treatment | Insecticide application |
|---|---|---|
| DP393 | Fungicide Only | Unsprayed |
|  | Fungicide Only | Sprayed |
|  | Acceleron® | Unsprayed |
|  | Acceleron® | Sprayed |
| MON 88702 | Fungicide Only | Unsprayed |
|  | Fungicide Only | Sprayed |
|  | Acceleron® | Unsprayed |
|  | Acceleron® | Sprayed |

*Thrips* damage ratings were obtained from multiple sites: VA, MS site 1, MS site 2, GA, MS site 3, LA site 1, LA site 2, SC, and TN. Two trials were performed in VA, MS site 3, and TN. Tables 11 through 22 show the mean *thrips* damage ratings for cotton transgenic event MON 88702 and the untransformed control, DP393 for each field site trail, wherein "SEM" is the standard error of the mean.

TABLE 11

Mean thrips damage ratings from VA, trial 1.

| Event | Seed Treatment | Insecticide application | Rating Date | Rating | SEM |
|---|---|---|---|---|---|
| DP393 | Fungicide Only | Unsprayed | 26-May | 3.50 | 0.00 |
|  | Fungicide Only | Unsprayed | 1-Jun | 4.25 | 0.10 |
|  | Fungicide Only | Sprayed | 26-May | 3.50 | 0.00 |
|  | Fungicide Only | Sprayed | 1-Jun | 4.00 | 0.00 |
|  | Acceleron® | Unsprayed | 26-May | 2.00 | 0.00 |
|  | Acceleron® | Unsprayed | 1-Jun | 3.75 | 0.00 |
|  | Acceleron® | Sprayed | 26-May | 2.06 | 0.06 |
|  | Acceleron® | Sprayed | 1-Jun | 2.69 | 0.06 |
| MON 88702 | Fungicide Only | Unsprayed | 26-May | 0.50 | 0.00 |
|  | Fungicide Only | Unsprayed | 1-Jun | 0.19 | 0.06 |
|  | Fungicide Only | Sprayed | 26-May | 0.31 | 0.06 |
|  | Fungicide Only | Sprayed | 1-Jun | 0.25 | 0.00 |
|  | Acceleron® | Unsprayed | 26-May | 0.00 | 0.00 |
|  | Acceleron® | Unsprayed | 1-Jun | 0.00 | 0.00 |
|  | Acceleron® | Sprayed | 26-May | 0.00 | 0.00 |
|  | Acceleron® | Sprayed | 1-Jun | 0.00 | 0.00 |

TABLE 12

Mean thrips damage ratings from VA, trial 2.

| Event | Seed Treatment | Insecticide application | Rating Date | Rating | SEM |
|---|---|---|---|---|---|
| DP393 | Fungicide Only | Unsprayed | 1-Jun | 4.44 | 0.06 |
|  | Fungicide Only | Unsprayed | 11-Jun | 4.19 | 0.12 |
|  | Fungicide Only | Sprayed | 1-Jun | 4.44 | 0.06 |
|  | Fungicide Only | Sprayed | 11-Jun | 4.25 | 0.10 |
|  | Acceleron® | Unsprayed | 1-Jun | 3.75 | 0.00 |
|  | Acceleron® | Unsprayed | 11-Jun | 4.19 | 0.06 |
|  | Acceleron® | Sprayed | 1-Jun | 3.75 | 0.14 |
|  | Acceleron® | Sprayed | 11-Jun | 4.13 | 0.07 |
| MON 88702 | Fungicide Only | Unsprayed | 1-Jun | 0.25 | 0.10 |
|  | Fungicide Only | Unsprayed | 11-Jun | 0.19 | 0.06 |
|  | Fungicide Only | Sprayed | 1-Jun | 0.31 | 0.06 |
|  | Fungicide Only | Sprayed | 11-Jun | 0.13 | 0.07 |
|  | Acceleron® | Unsprayed | 1-Jun | 0.06 | 0.06 |
|  | Acceleron® | Unsprayed | 11-Jun | 0.06 | 0.06 |
|  | Acceleron® | Sprayed | 1-Jun | 0.06 | 0.06 |
|  | Acceleron® | Sprayed | 11-Jun | 0.13 | 0.07 |

TABLE 13

Mean thrips damage ratings from MS site 1.

| Event | Seed Treatment | Insecticide application | Rating Date | Rating | SEM |
|---|---|---|---|---|---|
| DP393 | Fungicide Only | Unsprayed | 27-May | 3.00 | 0.20 |
|  | Fungicide Only | Unsprayed | 4-Jun | 3.75 | 0.14 |
|  | Fungicide Only | Sprayed | 27-May | 2.88 | 0.24 |
|  | Fungicide Only | Sprayed | 4-Jun | 3.50 | 0.00 |
|  | Acceleron® | Unsprayed | 27-May- | 2.00 | 0.41 |
|  | Acceleron® | Unsprayed | 4-Jun | 2.38 | 0.24 |
|  | Acceleron® | Sprayed | 27-May | 1.75 | 0.25 |
|  | Acceleron® | Sprayed | 4-Jun | 2.25 | 0.14 |
| MON 88702 | Fungicide Only | Unsprayed | 27-May | 0.88 | 0.31 |
|  | Fungicide Only | Unsprayed | 4-Jun | 1.13 | 0.13 |
|  | Fungicide Only | Sprayed | 27-May | 1.25 | 0.14 |
|  | Fungicide Only | Sprayed | 4-Jun | 1.38 | 0.13 |
|  | Acceleron® | Unsprayed | 27-May | 0.50 | 0.29 |
|  | Acceleron® | Unsprayed | 4-Jun- | 0.75 | 0.25 |
|  | Acceleron® | Sprayed | 27-May | 0.50 | 0.29 |
|  | Acceleron® | Sprayed | 4-Jun | 0.50 | 0.29 |

TABLE 14

Mean thrips damage ratings from MS site 2.

| Event | Seed Treatment | Insecticide application | Rating Date | Rating | SEM |
|---|---|---|---|---|---|
| DP393 | Fungicide Only | Unsprayed | 11-Jun | 2.38 | 0.13 |
|  | Fungicide Only | Unsprayed | 17-Jun | 3.56 | 0.06 |
|  | Fungicide Only | Sprayed | 11-Jun | 2.25 | 0.14 |
|  | Fungicide Only | Sprayed | 17-Jun | 3.38 | 0.16 |
|  | Acceleron ® | Unsprayed | 11-Jun | 2.13 | 0.13 |
|  | Acceleron ® | Unsprayed | 17-Jun | 3.06 | 0.06 |
|  | Acceleron ® | Sprayed | 11-Jun- | 2.00 | 0.00 |
|  | Acceleron ® | Sprayed | 17-Jun- | 2.25 | 0.31 |
| MON 88702 | Fungicide Only | Unsprayed | 11-Jun | 1.50 | 0.00 |
|  | Fungicide Only | Unsprayed | 17-Jun | 0.06 | 0.06 |
|  | Fungicide Only | Sprayed | 11-Jun | 1.38 | 0.13 |
|  | Fungicide Only | Sprayed | 17-Jun | 0.00 | 0.00 |
|  | Acceleron ® | Unsprayed | 11-Jun | 1.25 | 0.14 |
|  | Acceleron ® | Unsprayed | 17-Jun | 0.00 | 0.00 |
|  | Acceleron ® | Sprayed | 11-Jun | 1.13 | 0.13 |
|  | Acceleron ® | Sprayed | 17-Jun | 0.00 | 0.00 |

TABLE 15

Mean thrips damage ratings from GA.

| Event | Seed Treatment | Insecticide application | Rating Date | Rating | SEM |
|---|---|---|---|---|---|
| DP393 | Fungicide Only | Unsprayed | 28-May | 3.00 | 0.00 |
|  | Fungicide Only | Unsprayed | 4-Jun | 3.75 | 0.25 |
|  | Fungicide Only | Sprayed | 28-May | 3.00 | 0.00 |
|  | Fungicide Only | Sprayed | 4-Jun | 3.00 | 0.00 |
|  | Acceleron ® | Unsprayed | 28-May | 2.25 | 0.25 |
|  | Acceleron ® | Unsprayed | 4-Jun | 3.00 | 0.00 |
|  | Acceleron ® | Sprayed | 28-May | 2.25 | 0.25 |
|  | Acceleron ® | Sprayed | 4-Jun- | 3.00 | 0.00 |
| MON 88702 | Fungicide Only | Unsprayed | 28-May | 1.50 | 0.29 |
|  | Fungicide Only | Unsprayed | 4-Jun | 2.00 | 0.00 |
|  | Fungicide Only | Sprayed | 28-May | 1.75 | 0.25 |
|  | Fungicide Only | Sprayed | 4-Jun | 1.50 | 0.29 |
|  | Acceleron ® | Unsprayed | 28-May | 1.50 | 0.29 |
|  | Acceleron ® | Unsprayed | 4-Jun | 1.25 | 0.25 |
|  | Acceleron ® | Sprayed | 28-May | 1.00 | 0.00 |
|  | Acceleron ® | Sprayed | 4-Jun | 1.25 | 0.25 |

TABLE 16

Mean thrips damage ratings from MS site 3, trial 1.

| Event | Seed Treatment | Insecticide application | Rating Date | Rating | SEM |
|---|---|---|---|---|---|
| DP393 | Fungicide Only | Unsprayed | 28-May | 0.75 | 0.25 |
|  | Fungicide Only | Unsprayed | 8-Jun | 3.00 | 0.00 |
|  | Fungicide Only | Sprayed | 28-May | 0.50 | 0.29 |
|  | Fungicide Only | Sprayed | 8-Jun | 2.25 | 0.48 |
|  | Acceleron ® | Unsprayed | 28-May | 0.50 | 0.29 |
|  | Acceleron ® | Unsprayed | 8-Jun | 2.25 | 0.25 |
|  | Acceleron ® | Sprayed | 28-May | 1.25 | 0.25 |
|  | Acceleron ® | Sprayed | 8-Jun | 2.25 | 0.25 |
| MON 88702 | Fungicide Only | Unsprayed | 28-May | 0.50 | 0.29 |
|  | Fungicide Only | Unsprayed | 8-Jun | 1.50 | 0.29 |
|  | Fungicide Only | Sprayed | 28-May | 0.50 | 0.29 |
|  | Fungicide Only | Sprayed | 8-Jun | 1.50 | 0.29 |
|  | Acceleron ® | Unsprayed | 28-May | 0.50 | 0.29 |
|  | Acceleron ® | Unsprayed | 8-Jun | 1.75 | 0.25 |
|  | Acceleron ® | Sprayed | 28-May | 0.50 | 0.29 |
|  | Acceleron ® | Sprayed | 8-Jun | 1.50 | 0.29 |

TABLE 17

Mean thrips damage ratings from MS site 3, trial 2.

| Event | Seed Treatment | Insecticide application | Rating Date | Rating | SEM |
|---|---|---|---|---|---|
| DP393 | Fungicide Only | Unsprayed | 19-Jun | 2.00 | 0.00 |
|  | Fungicide Only | Unsprayed | 24-Jun | 3.00 | 0.00 |
|  | Fungicide Only | Sprayed | 19-Jun | 1.50 | 0.29 |
|  | Fungicide Only | Sprayed | 24-Jun | 2.00 | 0.41 |
|  | Acceleron ® | Unsprayed | 19-Jun | 1.75 | 0.25 |
|  | Acceleron ® | Unsprayed | 24-Jun | 2.00 | 0.00 |
|  | Acceleron ® | Sprayed | 19-Jun | 1.75 | 0.25 |
|  | Acceleron ® | Sprayed | 24-Jun | 2.00 | 0.00 |
| MON 88702 | Fungicide Only | Unsprayed | 19-Jun- | 1.25 | 0.25 |
|  | Fungicide Only | Unsprayed | 24-Jun- | 1.50 | 0.29 |
|  | Fungicide Only | Sprayed | 19-Jun | 1.00 | 0.00 |
|  | Fungicide Only | Sprayed | 24-Jun | 1.50 | 0.29 |
|  | Acceleron ® | Unsprayed | 19-Jun | 1.50 | 0.29 |
|  | Acceleron ® | Unsprayed | 24-Jun | 1.75 | 0.25 |
|  | Acceleron ® | Sprayed | 19-Jun | 1.25 | 0.25 |
|  | Acceleron ® | Sprayed | 24-Jun | 2.00 | 0.00 |

TABLE 18

Mean thrips damage ratings from LA site 1.

| Event | Seed Treatment | Insecticide application | Rating Date | Rating | SEM |
|---|---|---|---|---|---|
| DP393 | Fungicide Only | Unsprayed | 19-May | 3.00 | 0.00 |
|  | Fungicide Only | Unsprayed | 27-May | 4.00 | 0.00 |
|  | Fungicide Only | Sprayed | 19-May | 2.75 | 0.25 |
|  | Fungicide Only | Sprayed | 27-May | 3.75 | 0.25 |
|  | Acceleron ® | Unsprayed | 19-May | 2.00 | 0.00 |
|  | Acceleron ® | Unsprayed | 27-May | 3.25 | 0.25 |
|  | Acceleron ® | Sprayed | 19-May | 2.25 | 0.25 |
|  | Acceleron ® | Sprayed | 27-May | 3.00 | 0.00 |
| MON 88702 | Fungicide Only | Unsprayed | 19-May | 1.75 | 0.25 |
|  | Fungicide Only | Unsprayed | 27-May | 2.25 | 0.25 |
|  | Fungicide Only | Sprayed | 19-May | 1.75 | 0.25 |
|  | Fungicide Only | Sprayed | 27-May | 2.25 | 0.25 |
|  | Acceleron ® | Unsprayed | 19-May | 1.00 | 0.00 |
|  | Acceleron ® | Unsprayed | 27-May | 2.00 | 0.00 |
|  | Acceleron ® | Sprayed | 19-May | 1.25 | 0.25 |
|  | Acceleron ® | Sprayed | 27-May | 2.00 | 0.00 |

TABLE 19

Mean thrips damage ratings from LA (site 2).

| Event | Seed Treatment | Insecticide application | Rating Date | Rating | SEM |
|---|---|---|---|---|---|
| DP393 | Fungicide Only | Unsprayed | 19-May | 2.00 | 0.00 |
|  | Fungicide Only | Unsprayed | 28-May | 3.00 | 0.00 |
|  | Fungicide Only | Sprayed | 19-May | 1.75 | 0.25 |
|  | Fungicide Only | Sprayed | 28-May | 2.25 | 0.25 |
|  | Acceleron ® | Unsprayed | 19-May | 1.25 | 0.25 |
|  | Acceleron ® | Unsprayed | 28-May | 2.00 | 0.00 |
|  | Acceleron ® | Sprayed | 19-May | 1.67 | 0.33 |
|  | Acceleron ® | Sprayed | 28-May | 1.33 | 0.33 |

TABLE 19-continued

Mean thrips damage ratings from LA (site 2).

| Event | Seed Treatment | Insecticide application | Rating Date | Rating | SEM |
|---|---|---|---|---|---|
| MON 88702 | Fungicide Only | Unsprayed | 19-May | 1.00 | 0.00 |
|  | Fungicide Only | Unsprayed | 28-May | 1.25 | 0.25 |
|  | Fungicide Only | Sprayed | 19-May | 1.50 | 0.29 |
|  | Fungicide Only | Sprayed | 28-May | 1.25 | 0.25 |
|  | Acceleron ® | Unsprayed | 19-May | 1.00 | 0.00 |
|  | Acceleron ® | Unsprayed | 28-May | 1.50 | 0.29 |
|  | Acceleron ® | Sprayed | 19-May | 1.25 | 0.25 |
|  | Acceleron ® | Sprayed | 28-May | 1.25 | 0.25 |

TABLE 20

Mean thrips damage ratings from SC.

| Event | Seed Treatment | Insecticide application | Rating Date | Rating | SEM |
|---|---|---|---|---|---|
| DP393 | Fungicide Only | Unsprayed | 21-May | 2.25 | 0.25 |
|  | Fungicide Only | Unsprayed | 28-May- | 2.00 | 0.00 |
|  | Fungicide Only | Sprayed | 21-May | 2.00 | 0.00 |
|  | Fungicide Only | Sprayed | 28-May | 2.00 | 0.00 |
|  | Acceleron ® | Unsprayed | 21-May | 2.00 | 0.00 |
|  | Acceleron ® | Unsprayed | 28-May | 1.75 | 0.25 |
|  | Acceleron ® | Sprayed | 21-May | 2.25 | 0.25 |
|  | Acceleron ® | Sprayed | 28-May | 2.00 | 0.00 |
| MON 88702 | Fungicide Only | Unsprayed | 21-May | 1.00 | 0.00 |
|  | Fungicide Only | Unsprayed | 28-May | 1.50 | 0.29 |
|  | Fungicide Only | Sprayed | 21-May | 1.75 | 0.25 |
|  | Fungicide Only | Sprayed | 28-May | 1.25 | 0.25 |
|  | Acceleron ® | Unsprayed | 21-May- | 1.00 | 0.00 |
|  | Acceleron ® | Unsprayed | 28-May | 1.25 | 0.25 |
|  | Acceleron ® | Sprayed | 21-May | 1.00 | 0.00 |
|  | Acceleron ® | Sprayed | 28-May | 1.50 | 0.29 |

TABLE 21

Mean thrips damage ratings from TN, trial 1.

| Event | Seed Treatment | Insecticide application | Rating Date | Rating | SEM |
|---|---|---|---|---|---|
| DP393 | Fungicide Only | Unsprayed | 25-May | 3.50 |  |
|  | Fungicide Only | Unsprayed | 28-May | 3.60 | 0.06 |
|  | Fungicide Only | Unsprayed | 5-Jun | 4.03 | 0.03 |
|  | Fungicide Only | Unsprayed | 12-Jun | 4.03 | 0.12 |
|  | Fungicide Only | Sprayed | 25-May | 2.97 | 0.03 |
|  | Fungicide Only | Sprayed | 28-May | 2.55 | 0.09 |
|  | Fungicide Only | Sprayed | 5-Jun | 3.18 | 0.28 |
|  | Fungicide Only | Sprayed | 12-Jun | 2.68 | 0.17 |
|  | Acceleron ® | Unsprayed | 25-May | 2.05 | 0.15 |
|  | Acceleron ® | Unsprayed | 28-May | 2.33 | 0.03 |
|  | Acceleron ® | Unsprayed | 5-Jun | 2.90 | 0.07 |
|  | Acceleron ® | Unsprayed | 12-Jun | 3.05 | 0.03 |
|  | Acceleron ® | Sprayed | 25-May | 2.03 | 0.12 |
|  | Acceleron ® | Sprayed | 28-May | 1.80 | 0.04 |
|  | Acceleron ® | Sprayed | 5-Jun | 2.20 | 0.07 |
|  | Acceleron ® | Sprayed | 12-Jun | 2.33 | 0.17 |
| MON 88702 | Fungicide Only | Unsprayed | 25-May | 1.70 | 0.10 |
|  | Fungicide Only | Unsprayed | 28-May | 1.50 | 0.10 |
|  | Fungicide Only | Unsprayed | 5-Jun | 0.70 | 0.10 |
|  | Fungicide Only | Unsprayed | 12-Jun | 1.77 | 0.27 |
|  | Fungicide Only | Sprayed | 25-May | 1.83 | 0.13 |
|  | Fungicide Only | Sprayed | 28-May | 1.55 | 0.10 |
|  | Fungicide Only | Sprayed | 5-Jun | 0.53 | 0.08 |
|  | Fungicide Only | Sprayed | 12-Jun | 0.83 | 0.09 |
|  | Acceleron ® | Unsprayed | 25-May | 1.65 | 0.15 |
|  | Acceleron ® | Unsprayed | 28-May | 1.50 | 0.10 |
|  | Acceleron ® | Unsprayed | 5-Jun- | 0.45 | 0.15 |
|  | Acceleron ® | Unsprayed | 12-Jun | 0.75 | 0.35 |
|  | Acceleron ® | Sprayed | 25-May | 1.68 | 0.06 |
|  | Acceleron ® | Sprayed | 28-May | 1.33 | 0.11 |
|  | Acceleron ® | Sprayed | 5-Jun | 0.33 | 0.03 |
|  | Acceleron ® | Sprayed | 12-Jun | 0.40 | 0.04 |

TABLE 22

Mean thrips damage ratings from TN, trial 2.

| Event | Seed Treatment | Insecticide application | Rating Date | Rating | SEM |
|---|---|---|---|---|---|
| DP393 | Fungicide Only | Unsprayed | 8-Jun | 3.03 | 0.03 |
|  | Fungicide Only | Unsprayed | 11-Jun | 3.48 | 0.23 |
|  | Fungicide Only | Unsprayed | 15-Jun | 3.50 | 0.04 |
|  | Fungicide Only | Sprayed | 8-Jun | 3.00 | 0.04 |
|  | Fungicide Only | Sprayed | 11-Jun | 3.33 | 0.18 |
|  | Fungicide Only | Sprayed | 15-Jun | 2.85 | 0.10 |
|  | Acceleron ® | Unsprayed | 8-Jun | 2.23 | 0.11 |
|  | Acceleron ® | Unsprayed | 11-Jun | 2.28 | 0.11 |
|  | Acceleron ® | Unsprayed | 15-Jun | 2.40 | 0.15 |
|  | Acceleron ® | Sprayed | 8-Jun | 2.18 | 0.08 |
|  | Acceleron ® | Sprayed | 11-Jun | 2.18 | 0.13 |
|  | Acceleron ® | Sprayed | 15-Jun | 1.98 | 0.17 |
| MON 88702 | Fungicide Only | Unsprayed | 8-Jun | 1.20 | 0.11 |
|  | Fungicide Only | Unsprayed | 11-Jun | 0.78 | 0.09 |
|  | Fungicide Only | Unsprayed | 15-Jun | 0.68 | 0.09 |
|  | Fungicide Only | Sprayed | 8-Jun | 1.10 | 0.13 |
|  | Fungicide Only | Sprayed | 11-Jun | 0.80 | 0.07 |
|  | Fungicide Only | Sprayed | 15-Jun | 0.50 | 0.00 |
|  | Acceleron ® | Unsprayed | 8-Jun | 0.73 | 0.11 |
|  | Acceleron ® | Unsprayed | 11-Jun | 0.58 | 0.05 |
|  | Acceleron ® | Unsprayed | 15-Jun | 0.55 | 0.06 |
|  | Acceleron ® | Sprayed | 8-Jun | 0.70 | 0.04 |
|  | Acceleron ® | Sprayed | 11-Jun | 0.53 | 0.05 |
|  | Acceleron ® | Sprayed | 15-Jun | 0.35 | 0.03 |

As demonstrated in Tables 11 through 22, transgenic cotton event MON 88702 provides resistance to *thrips* under field conditions relative to the same untransformed variety. Transgenic event MON 88702 provided resistance to *thrips* at each field location when compared to the untransformed DP393. Resistance to *thrips* was observed in transgenic event MON 88702 without insecticidal seed treatment as well as without prophylactic foliar insecticide application. The *thrips* damage ratings for unsprayed MON 88702 plants grown from seed only treated with fungicide was lower than that of the untransformed DP393 that was both grown from seed treated with insecticide and sprayed with foliar insecticide. This is particularly salient in the two trials performed in VA (Tables 10 and 11). In many locations such as VA, MS site 2, and GA, the damage ratings for MON 88702 declined from the first data time point to the next, while the opposite trend was observed for the untransformed DP393, regardless of seed treatment and prophylactic spray. *Thrips* adults were collected and identified to assess species composition at each location. The observed species composition is shown in Table 23

TABLE 23

Thrips composition across different locations thrips trials.

| Field Location | Date of collection | Frankliniella fusca (Tobacco Thrips) | Frankliniella tritici (Flower Thrips) | Frankliniella occidentalis (Western Flower Thrips) | Sericothrips variabilis (Soybean Thrips) | other Thrips |
|---|---|---|---|---|---|---|
| MS site 3 | 28-May | 100 | 0 | 0 | 0 | 0 |
| MS site 3 | 8-Jun | 100 | 0 | 0 | 0 | 0 |
| MS site 1 | 28-May | 100 | 0 | 0 | 0 | 0 |
| MS site 1 | 4-Jun | 78 | 0 | 0 | 22 | 0 |
| MS site 2 | 11-Jun | 96 | 0 | 0 | 4 | 0 |
| MS site 2 | 17-Jun | 94 | 0 | 0 | 3 | 3 |
| LA site 1 | 27-May | 100 | 0 | 0 | 0 | 0 |
| LA site 2 | 19-May | 20 | 20 | 60 | 0 | 0 |
| LA site 2 | 28-May | 67 | 0 | 33 | 0 | 0 |
| TN | 28-May | 91 | 8 | 2 | 0 | 0 |
| TN | 5-Jun | 88 | 5 | 6 | 1 | 0 |
| TN | 11-Jun | 88 | 7 | 1 | 5 | 0 |
| TN | 15-Jun | 92 | 4 | 0 | 3 | 1 |
| GA | 21-May | 64 | 25 | 11 | 0 | 0 |
| GA | 28-May | 46 | 26 | 26 | 0 | 1 |
| GA | 4-Jun | 64 | 21 | 14 | 0 | 1 |
| SC | 28-May | 19 | 48 | 22 | 11 | 0 |
| SC | 3-Jun | 30 | 35 | 17 | 18 | 0 |
| VA | 21-May | 48 | 32 | 1 | 18 | 1 |
| VA | 1-Jun | 80 | 13 | 3 | 4 | 1 |
| VA | 1-Jun | 83 | 9 | 6 | 1 | 0 |
| VA | 8-Jun | 74 | 17 | 9 | 0 | 0 |

Example 8

Cotton Event MON 88702 Provides Resistance to Cotton Fleahopper (*Pseudatomoscelis seriatus*) as Demonstrated in Cage and Open Field Trials in Two Consecutive Years This example illustrates that transgenic cotton event MON 88702 provides resistance against the *Hemipteran* insect pest, *Pseudatomoscelis seriatus* (cotton fleahopper, CFH) when compared to the untransformed negative control, DP393.

Cage trials were performed in the field in TX during the year 1 cotton growing season and assayed for resistance against cotton fleahopper. Two (2) row plots of cotton were grown using one hundred twenty (120) seeds of cotton transgenic event MON 88702 or the untransformed DP393 negative control per thirty (30) foot long row (four seeds per row foot). Seeds were treated with Acceleron® which contains fungicides, the insecticide Imidacloprid, and the nematacide Thiodicarb.

At the second week of squaring, which occurs around thirty five (35) to forty (40) days after planting, ten (10) randomly selected plants (five (5) from each row) were enclosed in a cage (150×228 centimeters) made from white solid voile (JoAnne Fabrics, Item Number 8139875). The bottom voile sleeve was secured to the main plant stem just above the soil surface and the top sleeve was tied together using a Velcro® tie. Metal poles were placed at the end of each row and the top of each cage was attached to a string to keep the cages in an upright position.

Each plant was infested with two pairs of cotton fleahopper male and female adults. The adults were released into each individual cage and then the cage was securely closed ensuring the insects would not escape. The insects were allowed to mate and the plants were kept in the cage for thirty (30) days. After thirty days, the plants were then cut below the cages and moved to a laboratory where the insects were collected for each plant and counted. Before opening the cage, the plants were vigorously shaken to ensure all of the insects fell off from their feeding sites to the base of the cage. Then the cage base was opened. The plant was then thoroughly inspected to recover any remaining insects. The numbers of insects and their developmental stage were recorded for each plant. The mean numbers of next generation small nymphs (prior to $3^{rd}$ instar), large nymphs ($4^{th}$ and $5^{th}$ instars) and adults is presented in Table 24, wherein "SEM" is the standard error of the mean and "N" is the number of plants caged and sampled.

TABLE 24

Average next generation insect counts for cotton event MON 88702 and the negative control DP393 infested with CFH in TX, year 1 field caging trial.

| Event | N | Small Nymphs | Large Nymphs | Total Nymphs | Adults | Total CFH | Total CFH SEM |
|---|---|---|---|---|---|---|---|
| MON 88702 | 8 | 4.5 | 2.5 | 7 | 3.5 | 10.5 | 5.59 |
| DP393 | 7 | 6.43 | 1.43 | 7.86 | 13 | 20.86 | 5.23 |

As can be seen in Table 24, the total number of cotton fleahopper insects recovered from the cages for cotton event MON 88702 was approximately half the number found in the untransformed DP393 control. Of particular importance is the number of next generation adults recorded. The untransformed DP393 had approximately 4-fold more adults compared to event MON 88702, suggesting that over the course of development, fewer nymphs reach adulthood due to the expressed insect toxin, TIC834_16 in MON 88702. Cotton fleahoppers overwinter in the egg stage in various weed hosts including croton, evening primrose, silverleaf nightshade and lanceleaf sage. Eggs hatch in the spring with Cotton fleahoppers infesting available weed hosts. Once cotton begins to square, adult Cotton fleahoppers can and often do move into these fields. It usually takes a generation in the earlier cotton fields to produce economically damaging numbers. Reducing the number of adult Cotton fleahoppers in this earlier generation can potentially reduce the yield and economic impact caused by the next generation of Cotton fleahopper.

In year 2, the cotton fleahopper trials were conducted in a greenhouse. Twelve (12) plants of transgenic cotton event MON 88702 and the untransformed DP393 were grown in the greenhouse and were caged in a similar manner as described above. Infestation of cotton fleahopper and counts of small nymphs, large nymphs, and adults were also performed as previously described except that three pairs of adults were released in each cage. Table 25 shows the mean numbers of next generation small nymphs, large nymphs, and adults found for MON 88702 and DP393, wherein "SEM" is the standard error of the mean and "N" is the number of plants caged and sampled.

TABLE 25

Average next generation insect counts for cotton event MON 88702 and the negative control DP393 infested with CFH in TX, year 2 greenhouse caging trial.

| Event | N | Small Nymphs | Large Nymphs | Adults | Total CFH | Total CFH SEM |
|---|---|---|---|---|---|---|
| MON 88702 | 12 | 17.33 | 7.50 | 14.67 | 39.50 | 9.33 |
| DP393 | 10 | 18.10 | 6.60 | 42.10 | 66.80 | 7.96 |

As demonstrated in Table 25, the total number of cotton fleahoppers present on MON 88702 was less than that of the negative control, DP393. Consistent with the previous year's field cage trials, the number of adult cotton fleahopper associated with the negative control was much higher (approximately 3-fold) than that of MON 88702.

In the year 2 growing season, field trials were also conducted against cotton fleahopper in AZ and TX. Eight (8) row plots of cotton were grown using one hundred twenty (120) seeds of cotton transgenic event MON 88702 or the untransformed DP393 per thirty (30) foot long row (four seeds per row foot). Seeds were treated with Acceleron® (which contains fungicides, the insecticide Imidacloprid, and the nematacide Thiodicarb). There were four (4) reps of each entry at both locations.

Cotton fleahoppers were collected using the sweep net at the AZ location and the beat bucket at the TX location. The sweep net method essentially consists of sweeping through the top of the canopy for a specified number of sweeps and then counting the number of insects after separating for stages. A total of twenty (20) sweeps were conducted for each plot. The sweeps were conducted in two (2) runs of ten (10) sweeps each. The first run was performed between rows two and three. The second run was performed between rows six and seven. Insects trapped in the nets were put in pre-labeled bags and brought back to the lab for counting. The mean number of cotton fleahopper nymphs for MON 88702 and the untransformed control DP393 was determined for each site. In the beat bucket method, plants were shaken into a 5-gallon bucket ensuring all nymphs come off of the plant and all bucket contents were put in prelabeled zip lock bags. Three (3) runs of ten (10) plants sampling each with a total of thirty (30) plants sampled per plot per time.

In addition to cotton fleahopper counts, each plot was assessed for yield. Bolls were harvested from rows four (4) and five (5) and the average seed cotton yield was determined and expressed as seed cotton yield/acre. Table 26 shows the mean number of cotton fleahopper nymphs and the mean yield for MON 88702 and the untransformed control DP393 for each site wherein "SEM" is the standard error of the mean and "N" is the number of plants caged and sampled.

TABLE 26

Mean number of CFH nymphs and mean seed cotton yield in year 2 open field trials.

| | | CFH Nymphs | | | Yield/acre | | |
|---|---|---|---|---|---|---|---|
| Location | Event | N | Mean | SEM | N | Mean | SEM |
| Maricopa, AZ | MON 88702 | 28 | 8.29 | 1.73 | 4 | 5044.88 | 90.97 |
| | DP393 | 28 | 9.29 | 1.68 | 4 | 4525.13 | 115.97 |
| Corpus Christi, TX | MON 88702 | 32 | 3.47 | 1.07 | 4 | 2727.75 | 35.69 |
| | DP393 | 32 | 7.59 | 0.69 | 4 | 2621.25 | 163.47 |

Table 26 shows that the mean number of cotton fleahopper nymphs was lower for MON 88702 than in untransformed DP393. In addition, the mean cotton yield was higher in MON 88702 than in the untransformed DP393.

As demonstrated in Tables 24-26, cotton event MON 88702 provides resistance to cotton fleahopper in both cage trials and in the field and provides an increase in cotton yield.

Example 9

Cotton Event MON 88702 Provides Resistance to Verde Plant Bug (*Creontiades signatus*) as Demonstrated in Cage Trials This Example illustrates that transgenic cotton event MON 88702 provides resistance against the *hemipteran* insect pest *Creontiades signatus* Distant (Verde plant bug) in cage trials performed in TX when compared to the untransformed negative control DP393.

Verde plant bug nymphs were collected from plants in the field and brought back to the laboratory for rearing. Once the adults reached reproductive maturity (approximately ten (10) days after emergence), they were used to infest cotton event MON 88702 or the untransformed control DP393 in caged cotton plants.

Eight (8) row plots of cotton were grown using one hundred twenty (120) seeds of cotton transgenic event MON 88702 or the untransformed DP393 per thirty (30) foot long row (four (4) seeds per row foot). Seeds were treated with Acceleron® (which contains fungicides, the insecticide Imidacloprid, and the nematacide Thiodicarb). Four (4) replicate plots were grown per event. Twelve (12) plants for each event were randomly selected for caging. Any insects on the selected plants were removed prior to caging. Plants were caged at least a week before peak blooming as previously described in Example 2. Each plant was infested with two pairs of male and female Verde plant bug. The insects were allowed to oviposit and develop on each plant for four (4) weeks after infestation. Eight (8) to ten (10) bolls were harvested from each plant and examined for damage to the locules, as well as interior and exterior punctures made by the Verde plant bugs.

Table 27 shows the mean damaged locules from the harvested bolls, wherein "SEM" is the standard error of the mean and "N" is the number of plants caged and sampled.

As can be seen in Table 27, there were less damaged locules in MON 88702 event plants than in the untransformed control DP393.

TABLE 27

Mean damaged locules per boll per plant from plants infested with Verde plant bug.

| Event | N | Mean Damaged Locules | SEM |
|---|---|---|---|
| MON 88702 | 11 | 0.42 | 0.09 |
| DP393 | 11 | 0.89 | 0.16 |

Table 28 shows the mean exterior and interior punctures wherein "SEM" is the standard error of the mean and "N" is the number of plants caged and sampled. As can be seen in Table 28, the mean number of exterior and interior punctures in the bolls was lower for event MON 88702 than in the untransformed control DP393.

TABLE 28

Mean exterior and interior puncture per boll from plants infested with Verde plant bug.

| Event | N | Exterior Punctures | SEM | Interior Punctures | SEM |
|---|---|---|---|---|---|
| MON 88702 | 11 | 21.53 | 1.74 | 2.47 | 0.38 |
| DP393 | 11 | 29.22 | 3.46 | 6.55 | 1.53 |

As demonstrated in Tables 27 and 28, cotton event MON 88702 demonstrates resistance against Verde plant bug as evidenced in the lower amount of locule damage as well as fewer exterior and interior punctures when compared to the untransformed negative control DP393.

Example 10

Cotton Event MON 88702 Provides Consistent Yield, Similar Agronomics, and Similar Fiber Quality in the Field when Compared to Untransformed DP393

This Example demonstrates that transgenic cotton event MON 88702 provides consistent yields in the field.

Cotton event MON 88702 was compared to the untransformed DP393 in the field over two years of assessment in two consecutive years to assess any difference in yield under conditions in which insect infestation was controlled using insecticidal sprays against both non-*Lygus* and *Lygus* pests. Two (2) row plots of cotton were grown using one hundred sixty (160) seeds of cotton transgenic event MON 88702 or the untransformed DP393 negative control per forty (40) foot long row (four (4) seeds per row foot). Seeds were treated with Acceleron® which contains fungicides, the insecticide Imidacloprid, and the nematacide Thiodicarb. Each plot was replicated four (4) times. Insecticidal sprays were applied as needed to control both *Lygus* and non-*Lygus* insect pests to minimize any potential damage to the plots.

At the end of the season, the growth was terminated by using commercially available defoliants and boll openers. Defoliants used in this manner are often referred to as "harvest aids." Removing the leaves prior to harvest provides several advantages. For example, removing the leaves before harvest increases the air movement through the crop canopy which facilitates quicker drying and prevents boll rot. This process also allows the picker to begin earlier in the day and provides for a faster and more efficient picker operation. By reducing moisture more effectively, the storage of the bolls in modules is greatly improved. Removing the leaves also eliminates a main source of stain and trash which provides a better lint grade. Boll openers facilitate the opening of mature bolls which permits harvesting operations to start several days earlier, increasing the percentage of the crop harvested during the first picking, and makes picking an once-over operation in many fields. Defoliants and boll openers were applied when sixty (60) percent of the bolls were open in the field.

To assess yield, both rows of each two (2) row plot were harvested and the yield recorded as "seed cotton in pounds per acre". The yield results are presented in Table 29.

TABLE 29

Yield of seed cotton in pounds per acre from year 1 and year 2 field harvests.

| Event | Yield year 1 | Yield year 2 |
|---|---|---|
| MON 88702 | 3600.1 | 3855.4 |
| DP393 | 3585.1 | 3854.0 |

As demonstrated in Table 29 above, both MON 88702 and untransformed DP393 provided similar yields of cotton in the field. This demonstrates that cotton event MON 88702 in expressing the insect toxin TIC834_16 does not experience a yield drag due to expression of the transgene. In fact, as shown in Examples 4 and 5, cotton event MON 88702 provides a significant yield advantage with or without insecticide application under conditions of *Lygus* pressure.

The plants were also assessed for any phenotypic differences in both year 1 and year 2. Examples of phenotypic differences include early vigor score (EVS), number of nodes, plant height, and maturity (number of weeks). Early vigor score is determined at approximately ten (10) to fourteen (14) days after the plants have emerged. The score is a visual rating used to determine if the plot has full yield potential based upon the emergence of the plants in the plot. The plots are rated using a scale of one to five. A rating of four or five indicates low vigor, while a rating of one corresponds to high vigor. Table 30 shows the phenotypic values between MON 88702 and the negative control DP393 for early vigor, node number, plant height and plant maturity. Each of the values are expressed as an average. Comparisons were performed for each growing season. Those values indicated by "*" represent a significant difference (p=0.05) compared to the control within the growing season.

TABLE 30

Phenotypic characteristics of MON 88702 and untransformed DP393 grown in the field in year 1 and year 2.

| Year | Event | EVS | Node # | Plant Height | Maturity |
|---|---|---|---|---|---|
| 1 | MON 88702 | 2.6 | 15.8 | 32.5* | 13.7 |
|   | DP393 | 2.7 | 15.4 | 34.3 | 14.5 |
| 2 | MON 88702 | 1.9 | 14.8 | 32.2 | 13.6 |
|   | DP393 | 2.0 | 15.1 | 32.5 | 13.9 |

As can be seen in Table 30, cotton transgenic event MON 88702 demonstrated similar phenotypic characteristics as the untransformed DP393. A small difference was observed with respect to plant height in 2013, however the following year both MON 88702 and DP393 were around the same average height. With respect to early vigor stand, number of nodes and maturity, both MON 88702 and DP393 were not significantly different across growing seasons.

Twenty five (25) bolls per plot were collected prior to harvest for assessment of fiber quality and other characteristics. Bolls were collected from a representative spot in the planting row. All bolls were harvested from the selected plants to prevent the introduction of any bias in the collection due to size or other characteristics. Fiber quality characteristics such as fiber strength, fiber length, length uniformity and micronaire were determined from the harvested bolls. Fiber length was measured in inches.

Fiber strength measurement is made by clamping and breaking a bundle of fibers with a ⅛-inch spacing between the clamp jaws. Results are reported in terms of grams per tex to the nearest tenth. A tex unit is equal to the weight in grams of one thousand meters of fiber. Therefore, the strength reported is the force in grams required to break a bundle of fibers one tex unit in size. Table 31 shows a general description and corresponding strength measurements in grams per tex.

TABLE 31

Fiber strength description and corresponding strength measure.

| Description | Strength (grams per tex) |
| --- | --- |
| Weak | ≤23.0 |
| Intermediate | 24.0-25.0 |
| Average | 26.0-28.0 |
| Strong | 29.0-30.0 |
| Very Strong | ≥31.0 |

Length uniformity is a three-digit number that is a measure of the degree of uniformity of the fibers in a sample to the nearest tenth. Table 32 shows the length uniformity description and corresponding length uniformity score.

TABLE 32

Length uniformity description and score.

| Description | Length Uniformity |
| --- | --- |
| Very Low | ≤76.5 |
| Low | 76.5-79.4 |
| Average | 79.5-82.4 |
| High | 82.5-85.4 |
| Very High | ≥85.4 |

Micronaire is a measure of fiber fineness and maturity. An airflow instrument is used to measure the air permeability of a constant mass of cotton fibers compressed to a fixed volume. The volume of airflow through a specimen of cotton fibers is expressed as a micronaire. Cottons with micronaire measurements between 3.7 and 4.2 are considered in the premium range of micronaire. Cottons within the micronaire ranges of 3.5-3.6 or 4.3-4.9 are considered base quality, while cottons above 4.9 or below 3.5 are in the discount ranges. Micronaire measurements can be influenced during the growing period by environmental conditions such as moisture, temperature, sunlight, plant nutrients, and extremes in plant or boll population. Favorable growing conditions result in fully mature fibers with premium range micronaire readings. Unfavorable conditions, such as lack of moisture, early freeze, or any other conditions that interrupt plant processes, will result in immature fibers and low micronaire measurements. High micronaire cotton is caused by such things as abnormally warm temperatures during boll maturation, or poor boll set leading to excessive availability of carbohydrates and over-maturing of fibers. Fiber fineness affects processing performance and the quality of the end-product in several ways. In the opening, cleaning, and carding processes, low micronaire or fine-fiber cottons require slower processing speeds to prevent damage to the fibers. Yarns made from finer fiber result in more fibers per cross section, which in turn produces stronger yarns. High micronaire or coarse fibers are not suitable for fine yarns since the result would be fewer fibers per cross section, which would reduce the yarn strength. Micronaire and maturity are highly correlated within a cotton variety. Dye absorbency and retention varies with the maturity of the fibers. Low maturity fibers have poor dye absorbency and retention while higher micronaire fibers have good absorbency and retention.

Table 33 shows the fiber quality measures determined for both MON 88702 and the untransformed negative control DP393 for two consecutive growing seasons, year 1 and year 2. Those values indicated by "*" represent a significant difference (p=0.05) compared to the control within the growing season.

TABLE 33

Fiber quality of MON 88702 and DP393.

| Year | Event | Length | Strength | Uniformity | Micronaire |
| --- | --- | --- | --- | --- | --- |
| 1 | MON 88702 | 1.19 | 32.9 | 85.6 | 4.5 |
|   | DP393 | 1.19 | 33.6 | 85.5 | 4.8 |
| 2 | MON 88702 | 1.15 | 32.1* | 84.6 | 4.83 |
|   | DP393 | 1.13 | 34.7 | 84.4 | 5.04 |

As can be seen in Table 33, both event MON 88702 and the untransformed DP393 produced fiber of very similar qualities in both the 2013 and 2014 growing season. Event MON 88702 produced fiber with a similar length as the negative control. Both MON 88702 and DP393 produce very strong fiber with high to very high uniformity. The micronaire measures were not significantly different between MON 88702 and DP393. These result demonstrate that fiber quality is not adversely affected by the expression of the transgene cassette in MON 88702.

Example 11

Cotton Event MON 88702 Event Specific Endpoint TAQMAN® and Zygosity Assays

The following Example describes methods useful in identifying the presence of event MON 88702 in a cotton sample. A pair of PCR primers and a probe were designed for the purpose of identifying the unique junction formed between the cotton genomic DNA and the inserted DNA of event MON 88702 in an event specific endpoint TAQMAN® PCR. Examples of conditions utilized for identifying the presence of MON 88702 in a cotton sample in an event specific endpoint TAQMAN® PCR are described in Table 34 and Table 35.

The sequence of the oligonucleotide forward primer SQ21940 (SEQ ID NO:11) is identical to the nucleotide sequence corresponding to positions 4720 to 4744 of SEQ ID NO:10. The sequence of the oligonucleotide reverse primer SQ-50210 (SEQ ID NO:12) is identical to the reverse compliment of the nucleotide sequence corresponding to positions 4803 to 4826 of SEQ ID NO:10. The sequence of the oligonucleotide probe PB10344 (SEQ ID NO:13) is identical to the nucleotide sequence corresponding to positions 4745 to 4766 of SEQ ID NO: 10. The primers SQ21940 (SEQ ID NO:11) and SQ-50210 (SEQ ID NO:12) with probe PB10344 (SEQ ID NO:13), which may be fluorescently labeled (e.g., a 6FAM™ fluorescent label), can be used in an endpoint TAQMAN® PCR assay to identify the presence of DNA derived from event MON 88702 in a sample.

In addition to SQ21940 (SEQ ID NO:11), SQ-50210 (SEQ ID NO:12) and PB10344 (SEQ ID NO:13), it should be apparent to persons skilled in the art that other primers and/or probes can be designed to either amplify and/or hybridize to sequences within SEQ ID NO:10 which are unique to, and useful for, detecting the presence of DNA derived from event MON 88702 in a sample.

Following standard molecular biology laboratory practices, PCR assays for event identification were developed for detection of event MON 88702 in a sample. Parameters of either a standard PCR assay or a TAQMAN® PCR assay were optimized with each set of primer pairs and probes (e.g., probes labeled with a fluorescent tag such as 6FAM™) used to detect the presence of DNA derived from event MON 88702 in a sample. A control for the PCR reaction includes internal control primers and an internal control probe (e.g., VIC®-labeled) specific to a *Gossypium hirsutum* fiber-specific acyl carrier protein (ACP1) gene (GenBank Accession U48777), and are primers SQ22496 (SEQ ID NO:14), SQ22497 (SEQ ID NO:15), and VIC® labeled probe PB13032 (SEQ ID NO:17).

Generally, the parameters which were optimized for detection of event MON 88702 in a sample included primer and probe concentration, amount of templated DNA, and PCR amplification cycling parameters. The controls for this analysis include a positive control from cotton containing event MON 88702 DNA, a negative control from non-transgenic cotton, and a negative control that contains no template DNA.

TABLE 34

Cotton event MON 88702 event specific endpoint TAQMAN® PCR reaction components.

| Step | Reagent | Stock Concentration (µM) | Volume (µl) | Final Concentration (µM) | Comments |
|---|---|---|---|---|---|
|  | Reaction volume |  | 5 |  |  |
| 1 | 18 megohm water |  | 0.28 |  | Adjust for final volume |
| 2 | 2X Master Mix |  | 2.5 |  | 1X final concentration |
| 3 | Event Specific Primer SQ-50210 | 100 | 0.05 | 1 |  |
| 4 | Event Specific Primer SQ21940 | 100 | 0.05 | 1 |  |
| 5 | Event Specific 6FAM™ probe PB10344 | 100 | 0.01 | 0.2 | Probe is light sensitive |
| 6 | Internal Control Primer SQ22497 | 100 | 0.05 | 1 |  |
| 7 | Internal Control Primer SQ22496 | 100 | 0.05 | 1 |  |
| 8 | Internal Control VIC® probe PB13032 | 100 | 0.01 | 0.2 | Probe is light sensitive |
| 9 | Extracted DNA (template): Leaf Samples to be analyzed Negative control (non-transgenic DNA) Negative water control (No template control) Positive Qualitative control(s) MON 88702 DNA |  | 2 |  |  |

TABLE 35

Endpoint TAQMAN® thermocycler conditions

| Step No. | Cycle No. | Settings |
|---|---|---|
| 1 | 1 | 95° C. 20 seconds |
| 2 | 10 | 95° C. 3 seconds |
| 2 | 10 | 64° C.-1° C./Cycle 20 seconds |
| 3 | 30 | 95° C. 3 seconds |
| 3 | 30 | 54° C. 20 seconds |
| 4 | 1 | 10° C. 20 Forever |

A zygosity assay is useful for determining if a plant comprising an event is homozygous for the event DNA (i.e., comprising the exogenous DNA in the same location on each chromosome of a chromosomal pair), heterozygous for the event DNA (i.e., comprising the exogenous DNA on only one chromosome of a chromosomal pair), or wild-type (i.e., null for the event DNA). An endpoint TAQMAN® thermal amplification method was used to develop a zygosity assay for event MON 88702. Examples of conditions that may be used in an event specific zygosity TAQMAN® PCR are provide in Tables 36 and 37. For this assay, three primers and two probes were mixed together with the sample. The DNA primers used in the zygosity assay were primers SQ50844 (SEQ ID NO:17), SQ50843 (SEQ ID NO:19), and SQ50842 (SEQ ID NO:20). The probes used in the zygosity assay were 6FAM™-labeled probe PB50279 (SEQ ID NO:18) and VIC®-labeled probe PB50278 (SEQ ID NO:21). Primers SQ50844 (SEQ ID NO:17) and SQ50843 (SEQ ID NO:19) and the probe PB50279 (SEQ ID NO:18) (6FAM™-labeled) are diagnostic for event MON 88702 DNA. Primers SQ50842 (SEQ ID NO:20) and SQ50843 (SEQ ID NO:19) and the VIC®-labeled probe PB50278 (SEQ ID NO:21) are diagnostic when there is no copy of MON 88702; i.e., the wild type allele.

When the three primers and two probes are mixed together in a PCR reaction with DNA extracted from a plant heterozygous for event MON 88702, there is a fluorescent signal from both the 6FAM™-labeled probe PB50279 (SEQ ID NO:18) and the VIC®-labeled probe PB50278 (SEQ ID NO:21) which is indicative of and diagnostic for a plant heterozygous for event MON 88702. When the three primers and the two probes are mixed together in a PCR reaction with DNA extracted from a plant which is null for event MON 88702 (i.e., the wild-type), there is a fluorescent signal from only the VIC®-labeled probe PB50278 (SEQ ID NO:21) which is indicative of and diagnostic for a plant null for event MON 88702. The template DNA samples and controls for this analysis were a positive control from cotton containing event MON 88702 DNA (from both a known homozygous and a known heterozygous sample), a negative control from non-transgenic cotton and a negative control that contains no template DNA.

TABLE 36

Cotton event MON 88702 zygosity TAQMAN® PCR

| Step | Reagent | Stock Concentration (μM) | Volume (μl) | Final Concentration (μM) | Comments |
|---|---|---|---|---|---|
|  | Reaction Volume |  | 5 |  |  |
| 1 | 18 megohm water |  | 0.33 |  | adjust for final volume |
| 2 | 2X Master Mix |  | 2.5 |  | 1X final concentration of buffer |
| 3 | SQ50842 | 100 | 0.05 | 1 |  |
| 4 | SQ50843 | 100 | 0.05 | 1 |  |
| 5 | PB50278 | 100 | 0.01 | 0.2 |  |
| 6 | SQ50844 | 100 | 0.05 | 1 |  |
| 7 | PB50279 | 100 | 0.01 | 0.2 |  |
| 8 | Extracted DNA (template): Leaf Samples to be analyzed Negative control (non-transgenic DNA) Negative water control (No template control) Positive Qualitative control(s) MON 88702 DNA |  | 2 |  |  |

TABLE 37

Zygosity TAQMAN® thermocycler conditions

| Step No. | Cycle No. | Settings |
|---|---|---|
| 1 | 1 | 95° C. 20 seconds |
| 2 | 40 | 95° C. 3 seconds |

TABLE 37-continued

Zygosity TAQMAN® thermocycler conditions

| Step No. | Cycle No. | Settings |
|---|---|---|
| 2 | 40 | 60° C. 20 seconds |
| 4 | 1 | 10° C. 20 Forever |

Example 12

Identification of Cotton Event MON 88702 in Any MON 88702 Breeding Event

The following Example describes how one may identify the MON 88702 event within progeny of any breeding activity using cotton event MON 88702.

DNA primer pairs are used to produce an amplicon diagnostic for cotton event MON 88702. An amplicon diagnostic for MON 88702 comprises at least one junction sequence, SEQ ID NO:1, SEQ ID NO:2, SEQ ID NO:3, SEQ ID NO:4, SEQ ID NO:5, or SEQ ID NO:6 ([1], [2], [3], [4], [5], and [6], respectively in FIG. 1a). SEQ ID NO:1 is a twenty (20) nucleotide sequence representing the 5' junction regions of cotton genomic DNA and the integrated transgenic expression cassette. SEQ ID NO:1 is positioned in SEQ ID NO:10 at nucleotide position 1642-1661. SEQ ID NO:2 is a twenty (20) nucleotide sequence representing the 3' junction regions of cotton genomic DNA and the integrated transgenic expression cassette. SEQ ID NO:2 is positioned in SEQ ID NO:10 at nucleotide position 4785-4804. SEQ ID NO:3 is a sixty (60) nucleotide sequence representing the 5' junction regions of cotton genomic DNA and the integrated transgenic expression cassette. SEQ ID NO:3 is positioned in SEQ ID NO:10 at nucleotide position 1622-1681. SEQ ID NO:4 is a sixty (60) nucleotide sequence representing the 3' junction regions of cotton genomic DNA and the integrated transgenic expression cassette. SEQ ID NO:4 is positioned in SEQ ID NO:10 at nucleotide position 4765-4824. SEQ ID NO:5 is a one hundred nucleotide sequence representing the 5' junction regions of cotton genomic DNA and the integrated transgenic expression cassette. SEQ ID NO:5 is positioned in SEQ ID NO:10 at nucleotide position 1602-1701. SEQ ID NO:6 is a one hundred nucleotide sequence representing the 3' junction regions of cotton genomic DNA and the integrated transgenic expression cassette. SEQ ID NO:6 is positioned in SEQ ID NO:10 at nucleotide position 1602-1701.

Primer pairs that will produce an amplicon diagnostic for event MON 88702 include primer pairs based upon the flanking sequences and the inserted TIC834_16 expression cassette. To acquire a diagnostic amplicon in which at least eleven nucleotides of SEQ ID NO:1 is found, one would design a forward primer based upon SEQ ID NO:7 from bases 1 through 1651 and a reverse primer based upon SEQ ID NO:9. To acquire a diagnostic amplicon in which at least eleven nucleotides of SEQ ID NO:2 is found, one would design a forward primer based upon SEQ ID NO:9 and a reverse primer based upon SEQ ID NO:8 from bases 1 through 2010. To acquire a diagnostic amplicon in which at least thirty one nucleotides of SEQ ID NO:3 is found, one would design a forward primer based upon SEQ ID NO:7 from bases 1 through 1651 and a reverse primer based upon SEQ ID NO:9. To acquire a diagnostic amplicon in which at least thirty one nucleotides of SEQ ID NO:4 is found, one would design a forward primer based upon SEQ ID NO:9 and a reverse primer based upon SEQ ID NO:8 from bases 1 through 2010. To acquire a diagnostic amplicon in which at least fifty one nucleotides of SEQ ID NO:5 is found, one would design a forward primer based upon SEQ ID NO:7 from bases 1 through 1651 and a reverse primer based upon SEQ ID NO:9. To acquire a diagnostic amplicon in which at least fifty one nucleotides of SEQ ID NO:6 is found, one would design a forward primer based upon SEQ ID NO:9 and a reverse primer based upon SEQ ID NO:8 from bases 1 through 2010.

For practical purposes, one should design primers which produce amplicons of a limited size range, preferably between 200 to 1000 bases. Smaller sized amplicons in general are more reliably produced in PCR reactions, allow for shorter cycle times, and can be easily separated and visualized on agarose gels or adapted for use in endpoint TAQMAN®-like assays. In addition, amplicons produced using said primer pairs can be cloned into vectors, propagated, isolated and sequenced, or can be sequenced directly with methods well established in the art. Any primer pair derived from the combination of SEQ ID NO:7 and SEQ ID NO:9, or the combination of SEQ ID NO:8 and SEQ ID NO:9 that are useful in a DNA amplification method to produce an amplicon diagnostic for MON 88702 or progeny thereof is an aspect of the present invention. Any single isolated DNA polynucleotide primer molecule comprising at least eleven contiguous nucleotides of SEQ ID NO:7, or its complement that is useful in a DNA amplification method to produce an amplicon diagnostic for MON 88702 or progeny thereof is an aspect of the present invention. Any single isolated DNA polynucleotide primer molecule comprising at least eleven contiguous nucleotides of SEQ ID NO:8, or its complement that is useful in a DNA amplification method to produce an amplicon diagnostic for MON 88702 or progeny thereof is an aspect of the present invention. Any single isolated DNA polynucleotide primer molecule comprising at least eleven contiguous nucleotides of SEQ ID NO:9, or its complement that is useful in a DNA amplification method to produce an amplicon diagnostic for MON 88702 or progeny thereof is an aspect of the present invention.

An example of the amplification conditions for this analysis is illustrated in Tables 34 and 35 of the previous Example. However, any modification of these methods or the use of DNA primers homologous or complementary to SEQ ID NO:6 or SEQ ID NO:7, or DNA sequences of the genetic elements contained in the transgene insert (SEQ ID NO:9) of MON 88702 that produce an amplicon diagnostic for MON 88702, is within the art. A diagnostic amplicon comprises a DNA molecule homologous or complementary to at least one transgene/genomic junction DNA (SEQ ID NO:1, SEQ ID NO:2, SEQ ID NO:3, SEQ ID NO:4, SEQ ID NO:5, or SEQ ID NO:6), or a substantial portion thereof.

An analysis for event MON 88702 plant tissue sample should include a positive tissue control from event MON 88702, a negative control from a cotton plant that is not event MON 88702 (for example, but not limited to DP393) and a negative control that contains no cotton genomic DNA. A primer pair will amplify an endogenous cotton DNA molecule and will serve as an internal control for the DNA amplification conditions. Additional primer sequences can be selected from SEQ ID NO: 7, SEQ ID NO: 8, or SEQ ID NO: 9 by those skilled in the art of DNA amplification methods, and conditions selected for the production of an amplicon by the methods shown in Table 34 and Table 35 may differ, but result in an amplicon diagnostic for event MON 88702 DNA. The use of these DNA primer sequences with modifications to the methods of Table 34 and Table 35 are within the scope of the invention. The amplicon produced by at least one DNA primer sequence derived from SEQ ID NO:7, SEQ ID NO:8, or SEQ ID NO:9 that is diagnostic for MON 88702 is an aspect of the invention.

DNA detection kits that contain at least one DNA primer of sufficient length of contiguous nucleotides derived from SEQ ID NO:7, SEQ ID NO:8, or SEQ ID NO:9, that when used in a DNA amplification method, produces a diagnostic amplicon for MON 88702 or its progeny is an aspect of the invention. A cotton plant or seed, wherein its genome will produce an amplicon diagnostic for MON 88702 when tested in a DNA amplification method is an aspect of the invention. The assay for the MON 88702 amplicon can be performed by using an Applied Biosystems GeneAmp PCR System 9700, Stratagene Robocycler, MJ Engine, Perkin-Elmer 9700, Eppendorf Mastercycler Gradient thermocycler or any other amplification system that can be used to produce an amplicon diagnostic of MON 87702 as shown in Table 35.

Example 13

Crossing of Plants Containing Event MON 87702

To produce cotton plants or plant parts thereof which comprise enhanced agronomic, insecticidal, or herbicidal properties, cotton plants containing MON 87702 are crossed with cotton plants containing potentially any other cotton event or combination thereof and phenotypes are evaluated to determine the resulting properties of the progeny plants. Properties conferred to progeny plants resulting from such plant breeding can extend beyond the *Hemipteran* and *Thysanopteran* resistance of MON 87702, including, but not limited to above-ground pest control, herbicide tolerance, nematicidal properties, drought resistance, virus resistance, anti-fungal control, bacteria resistance, male sterility, cold tolerance, salt tolerance, and increased yield. Examples of transgenic events with improved agronomic traits are well known in the art. The following is a non-limiting list of possible transgenic cotton lines which can be used in breeding with MON 87702 to confer enhanced properties in cotton plants, plant parts, seed or commodity product: 19-51A (DD-04951A-7), BXN, MON 1445 (MON-01445-2), MON 88701 (MON-88701-3), MON 88913 (MON-88913-8), GHB614 (BCS-GH002-5), DAS-81910-7 (DAS-81910-7), GHB119 (BCS-GH005-8), LLCotton25 (ACS-GH0013), EE-GH1, EE-GH3, pDAB4468.18.07.1, pDAB4468.19.10.3, 281-24-236 (DAS-24236-5), 3006-210-23 (DAS-21023-5), COT102 (SYN-IR102-7), COT67B (SYN-IR67B-1), Event-1, MON 531 (MON-00531-6), MON15985 (MON-15985-7), EE-GHS, EE-GH6, COT202, COT203, A26-5, 31807, 31808, T303-3 (BCS-GH003-6), and T304-40 (BCS-GH004-7).

All publications and published patent documents cited in this specification, and which are material to the invention, are incorporated herein by reference to the same extent as if each individual publication or patent application was specifically and individually indicated to be incorporated by reference.

Having illustrated and described the principles of the present invention, it should be apparent to persons skilled in the art that the invention can be modified in arrangement and detail without departing from such principles. We claim all modifications that are within the spirit and scope of the appended claims.

What is claimed is:

1. A method for protecting a cotton plant from insect infestation, wherein said method comprises providing in the diet of a Hemipteran insect pest or Thysanopteran insect pest an insecticidally effective amount of cells or tissue of a cotton plant comprising event MON 88702, wherein a representative sample of seed comprising event MON 88702 has been deposited as ATCC accession No. PTA-122520.

2. The method of claim 1, wherein said Hemipteran insect pest is selected from the group consisting of *Lygus hesperus, Lygus lineolaris,* and *Pseudatomoscelis seriatus*.

3. The method of claim 1, wherein said Thysanopteran insect pest is selected from the group consisting of *Frankliniella* spp and *Sericothrips variabilis*.

4. A method of producing an insect resistant cotton plant comprising:
   a) sexually crossing two different cotton plants with at least one of the two different cotton plants comprising transgenic cotton event MON 88702 DNA, wherein a representative sample of seed comprising event MON 88702 has been deposited as ATCC accession No. PTA-122520;
   b) sampling seed or tissue from progeny of the crossing;
   c) detecting a sequence diagnostic for cotton event MON 88702 in said sample from step (b) to identify progeny comprising cotton event MON 88702 DNA; and
   d) selecting said progeny comprising cotton event MON 88702 DNA, wherein the progeny is an insect resistant cotton plant comprising transgenic cotton event MON 88702 DNA.

5. A cotton plant, cotton plant part, or cotton seed thereof comprising event MON 88702 DNA, wherein a representative sample of seed comprising event MON 88702 has been deposited as ATCC accession No. PTA-122520.

6. A method of determining the zygosity of a cotton plant or cotton seed comprising event MON 88702 comprising:
   a) contacting a sample comprising cotton DNA comprising event MON 88702 with a primer set capable of producing a first amplicon diagnostic for event MON 88702 and a second amplicon diagnostic for native cotton genomic DNA not comprising event MON 88702, wherein a representative sample of seed comprising event MON 88702 has been deposited as ATCC accession No. PTA-122520;
   i) performing a nucleic acid amplification reaction with the sample and the primer set; and
   ii) detecting in the nucleic acid amplification reaction the first amplicon diagnostic for event MON 88702, or the second amplicon diagnostic for native cotton genomic DNA not comprising event MON 88702, wherein the presence of only the first amplicon is diagnostic of a cotton plant homozygous for event MON 88702 DNA in the sample, and the presence of both the first amplicon and the second amplicon is diagnostic of a cotton plant heterozygous for event MON 88702 allele; or
   b) contacting a sample comprising cotton DNA with a probe set which contains at least a first probe that specifically hybridizes to event MON 88702 DNA and at least a second probe that specifically hybridizes to cotton genomic DNA that was disrupted by insertion of the heterologous DNA of event MON 88702 and does not hybridize to event MON 88702 DNA,
   i) hybridizing the probe set with the sample under stringent hybridization conditions, and
   ii) detecting hybridization of the first probe or the second probe, wherein detecting hybridization of only the first probe under the hybridization conditions is diagnostic for a homozygous allele of event MON 88702 DNA in the sample, and wherein detecting hybridization of both the first probe and the second probe under the hybridization conditions is diagnostic for a heterozygous allele of event MON 88702 in a DNA sample.

7. The method of claim 6, wherein the primer set comprises SEQ ID NO:17, SEQ ID NO:19 and SEQ ID NO:20.

8. The method of claim 6, wherein the probe set comprises SEQ ID NO:18 and SEQ ID NO:21.

* * * * *